(12) United States Patent
Ogawa et al.

(10) Patent No.: US 8,952,176 B2
(45) Date of Patent: *Feb. 10, 2015

(54) HETEROCYCLIC COMPOUND HAVING TYPE I 11 β HYDROXYSTEROID DEHYDROGENASE INHIBITORY ACTIVITY

(75) Inventors: Tomoyuki Ogawa, Osaka (JP); Noriyuki Kurose, Osaka (JP); Satoru Tanaka, Osaka (JP); Koichi Nishi, Amagasaki (JP)

(73) Assignee: Shionogi & Co., Ltd., Osaka (JP)

( * ) Notice: Subject to any disclaimer, the term of this patent is extended or adjusted under 35 U.S.C. 154(b) by 1713 days.

This patent is subject to a terminal disclaimer.

(21) Appl. No.: 11/916,173

(22) PCT Filed: Jun. 6, 2006

(86) PCT No.: PCT/JP2006/311257
§ 371 (c)(1),
(2), (4) Date: Nov. 30, 2007

(87) PCT Pub. No.: WO2006/132197
PCT Pub. Date: Dec. 14, 2006

(65) Prior Publication Data
US 2010/0197662 A1    Aug. 5, 2010

(30) Foreign Application Priority Data

Jun. 7, 2005  (JP) ................. 2005-166556
Oct. 28, 2005  (JP) ................. 2005-313998

(51) Int. Cl.
| | | |
|---|---|---|
| C07D 261/12 | (2006.01) | |
| C07D 261/18 | (2006.01) | |
| C07D 413/12 | (2006.01) | |
| C07D 261/10 | (2006.01) | |
| C07D 413/06 | (2006.01) | |
| C07D 413/14 | (2006.01) | |
| C07D 417/12 | (2006.01) | |
| C07D 471/10 | (2006.01) | |
| C07D 487/08 | (2006.01) | |

(52) U.S. Cl.
CPC ............ *C07D 261/10* (2013.01); *C07D 261/18* (2013.01); *C07D 413/06* (2013.01); *C07D 413/12* (2013.01); *C07D 413/14* (2013.01); *C07D 417/12* (2013.01); *C07D 471/10* (2013.01); *C07D 487/08* (2013.01)
USPC ........... 548/243; 514/372; 544/140; 544/371; 546/209; 546/272.1

(58) Field of Classification Search
CPC ... C07D 261/12; C07D 261/18; C07D 413/12
See application file for complete search history.

(56) References Cited

U.S. PATENT DOCUMENTS

| 4,562,187 A | 12/1985 | Tegeler et al. |
| 5,001,124 A | 3/1991 | Patterson et al. |
| 2003/0225106 A1* | 12/2003 | Askew et al. ............ 514/256 |

(Continued)

FOREIGN PATENT DOCUMENTS

| EP | 0 067 436 | 12/1982 |
| EP | 1 460 071 | 9/2004 |

(Continued)

OTHER PUBLICATIONS

Vippagunta et al.; "Crystalline solids"; 2001; Advanced Drug Delivery Reviews; 48: 3-26.*
Montori et al.; "Waking up for the Dream of preventing diabetes with drugs"; 2007; BMJ; 334: 882-884.*
Dal Piaz ; "4,5-Disubstituted-3-carboethoxyisoxazoles. II. Hydrolysis and derivatives"; 1968; Gazzetta Chimica Italiana; 98(5): 667-80; CAPLUS abstract; Accession No. 1968:486874.*
Aβmann, L. et al., "3-Methyl-4,6-diphenylfuro [3,4-d]isoxazol-Ein neues heterocyclisches system", Chemische Berichte, 1991, vol. 124, No. 11, pp. 2481 to 2488, particularly, compound 5.

(Continued)

*Primary Examiner* — Timothy Thomas
(74) *Attorney, Agent, or Firm* — Hamre, Schumann, Mueller & Larson, P.C.

(57) ABSTRACT

Disclosed is a compound useful as a type I 11βhydroxysteroid dehydrogenase inhibitor. A compound represented by the formula:

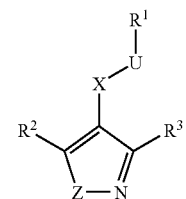

a pharmaceutically acceptable salt or solvate thereof, wherein
$R^1$ is optionally substituted cycloalkyl, optionally substituted cycloalkenyl or the like,
One of $R^2$ and $R^3$ is a group of the formula: —C(=O)—Y—$R^4$,
wherein Y is —$NR^9$— or the like,
$R^4$ is optionally substituted cycloalkyl or the like,
$R^9$ is hydrogen or optionally substituted alkyl,
W is optionally substituted alkylene,
The other is a group of the formula: —V—$R^5$,
wherein V is a bond, —O— or the like,
$R^6$ is hydrogen or optionally substituted alkyl,
$R^5$ is hydrogen, optionally substituted alkyl or the like,
X is a bond, —S—, —SO— or the like,
U is a bond or optionally substituted alkylene,
$R^7$ is hydrogen or optionally substituted alkyl,
Z is —S—, —O— or —$NR^8$—,
$R^8$ is hydrogen, optionally substituted alkyl or the like.

14 Claims, No Drawings

(56) References Cited

U.S. PATENT DOCUMENTS

| | | |
|---|---|---|
| 2005/0245532 A1 | 11/2005 | Hoff et al. |
| 2005/0245533 A1 | 11/2005 | Hoff et al. |
| 2005/0261302 A1 | 11/2005 | Hoff et al. |
| 2006/0148871 A1 | 7/2006 | Rohde et al. |

FOREIGN PATENT DOCUMENTS

| | | |
|---|---|---|
| EP | 1 894 919 | 3/2008 |
| EP | 1 953 145 | 8/2008 |
| JP | 59-128306 | 7/1984 |
| JP | 59-128326 | 7/1984 |
| JP | 2002-069061 | 3/2002 |
| WO | 03/006454 | 1/2003 |
| WO | 03/013517 | 2/2003 |
| WO | 03/043999 | 5/2003 |
| WO | 2004/056744 | 7/2004 |
| WO | 2004/056745 | 7/2004 |
| WO | 2004/058255 | 7/2004 |
| WO | 2004/058741 | 7/2004 |
| WO | 2004/065351 | 8/2004 |
| WO | 2004/089470 | 10/2004 |
| WO | 2005/016877 | 2/2005 |
| WO | WO 2005/097764 A1 | 10/2005 |
| WO | WO 2005/108359 A1 | 11/2005 |
| WO | WO 2005/108361 A1 | 11/2005 |
| WO | WO 2005/108368 A1 | 11/2005 |
| WO | 2006/002361 | 1/2006 |
| WO | 2006/012227 | 2/2006 |
| WO | WO 2006/024627 A2 | 3/2006 |
| WO | WO 2006/024628 A1 | 3/2006 |
| WO | WO 2006/048750 A2 | 5/2006 |
| WO | WO 2006/074244 A2 | 7/2006 |
| WO | WO 2006/074330 A2 | 7/2006 |
| WO | WO 2006/100502 A1 | 9/2006 |

OTHER PUBLICATIONS

"11β-Hydroxysteroid dehydrogenase: implications for clinical medicine", Paul M. Stewart, Clinical Molecular Endocrinology, 44, 1996 Blackwell Science Ltd., pp. 493-499.

"Carbonoxolone Increases Hepatic Insulin Sensitivity in Man: A Novel Role for 11-Oxosteroid Reductase in Enhancing Glucocorticoid Receptor Activation", Walker et al., Journal of Clinical Endocrinology and Metabolism, vol. 80, No. 11, 1995, pp. 3155-3159.

"Does central obesity reflect "Cushing's disease of the omentum"?", Bujalska et al., The Lancet, vol. 349, Apr. 26, 1997, pp. 1210-1213.

"11β-Hydroxysteroid dehydrogenase type 1 knockout mice show attenuated glucocorticoid-inducible responses and resist hyperglycemia on obesity or stress", Proc. Natl. Acad. Sci., vol. 94. pp. 14924-14929, Dec. 1997 Physiology, pp. 14924-14929.

Klötzer et al. "Reaktionen des 4-Methoxy-3, 5-dicarbomethoxy-isoxazols (v. Pechmann-Ester)." Monatschefte fuer Chemie, vol. 95(1), 1964, pp. 102-115.

Morissette et al., "High-throughput crystallization: polymorphs, salts, co-crystals and solvates of pharmaceutical solids," Advanced Drug Delivery Reviews, 2005, vol. 56, pp. 275-300.

\* cited by examiner

HETEROCYCLIC COMPOUND HAVING TYPE I 11 β HYDROXYSTEROID DEHYDROGENASE INHIBITORY ACTIVITY

FIELD OF THE INVENTION

This invention relates to a compound with inhibitory activity to 11βhydroxysteroid dehydrogenase type I (hereinafter referred to as 11β-HSD-1) and a pharmaceutical composition comprising it.

BACKGROUND ART

11β-HSD-1 is an enzyme that converts inactive steroids, 11β-dehydrosteroid into its active steroids and is considered to be important in the basal metabolic rate in the living body (Non-patent Document 1). Moreover, 11β-HSD-1 knockout mice have the resistance to hyperglycemia induced by obesity and stress (Non-patent Document 2). In addition, a similar phenomenon was observed in human on administration of 11β-HSD-1 inhibitor, carbenoxolone (Non-patent Document 3). These facts suggest that the 11β-HSD-1 inhibitors could be useful as drugs for the treatment of insulin independent diabetes and obesity (Non-patent Document 4).

Patent Document 1 describes that hetero ring derivatives are useful as kinase inhibitors for the treatment of cancer, Alzheimer's disease, viral infections and autoimmune disease, but does not describe the inhibitory activity to the type 11β hydroxysteroid dehydrogenase.

The compounds having an isoxazole group have been described in Patent Document 2 as a useful compound for the treatment of hypertension as well as inflammation and the structure of them are limited to that without substituent at 4-position on an isoxazole group, and no compounds having the substituent on an isoxazole group such as the present compound have not been described.

Patent Document 3 to 6 disclose various compounds that have the inhibitory activity to 11β hydroxysteroid dehydrogenase type 1.

Patent Document 3 and 4 mainly disclose the compounds having a phenyl group, and does not disclose the compounds having an isoxazole group described in the present invention.

Patent Document 5 does not disclose the compounds having an isoxazole group described in the present invention.

Patent Document 6 describes the compounds having a pyrazole group. The substituent at 4 position on the pyrazole group is hydrogen, halogen or optionally substituted alkyl (the substituent is hydroxyl or fluorine). The above document does not disclose the compounds having a cyclohexyl group described in the present invention.

[Patent Document 1] WO03/013517
[Patent Document 2] U.S. Pat. No. 4,562,187
[Patent Document 3] WO04/056744
[Patent Document 4] WO04/056745
[Patent Document 5] WO04/065351
[Patent Document 6] WO05/016877
[Non-patent Document 1] Clin. Endocrinol, 1996, 44, 493
[Non-patent Document 2] Proc. Nat. Acad. Sci. USA, 1997, 94, 14924
[Non-patent Document 3] J. Clin. Endocrinol. Metab., 1995, 80, 3155
[Non-patent Document 4] Lancet, 1997, 349, 1210

DISCLOSURE OF INVENTION

Problems to be Solved by the Invention

The present invention provides compounds having high inhibitory activity to 11βhydroxysteroid dehydrogenase type 1.

Means for Solving the Problem

The present invention provides;
(1) A compound represented by the formula (I):

[Formula 1]

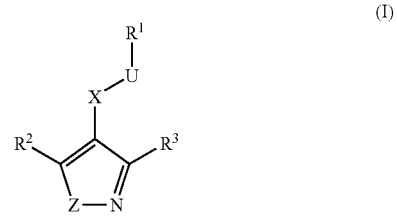

a pharmaceutically acceptable salt or a solvate thereof,
wherein
$R^1$ is optionally substituted cycloalkyl, optionally substituted cycloalkenyl, optionally substituted aryl, optionally substituted heteroaryl or optionally substituted heterocycle,
one of $R^2$ and $R^3$ is a group of the formula: —C(=O)—Y—$R^4$,
wherein Y is —$NR^9$—, —C(=O)—, —$CH_2$—, a bond or —$NR^9$—W—,
$R^4$ is optionally substituted cycloalkyl, optionally substituted cycloalkenyl, optionally substituted aryl, optionally substituted heteroaryl or optionally substituted heterocycle,
$R^9$ is hydrogen or optionally substituted alkyl, and
W is optionally substituted alkylene,
the other of $R^2$ and $R^3$ is a group of the formula: —V—$R^5$, halogen or hydroxy,
V is a bond, —O—, —C(=O)—, —$SO_2$— or —$NR^6$—,
$R^6$ is hydrogen or optionally substituted alkyl,
$R^5$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle,
X is a bond, —S—, —SO—, —$SO_2$—, —O—, —C≡C—, —C(=O)—, —$NR^7$—, —C(=O)—$NR^7$—, —$NR^7$—C(=O)—, —$SO_2$—$NR^7$—, —CH=CH— or —$NR^7$—$SO_2$—,
U is a bond or optionally substituted alkylene,
$R^7$ is hydrogen or optionally substituted alkyl,
Z is —S—, —O— or —$NR^8$—,
$R^8$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle; or $R^8$ and $R^2$ taken together may form an optionally substituted ring,
(2) The compound according to the above (1), a pharmaceutically acceptable salt or a solvate thereof, wherein $R^2$ is a group of the formula: —C(=O)—Y—$R^4$ wherein Y and $R^4$ have the same meanings as defined in the above (1).

(3) The compound according to the above (2), a pharmaceutically acceptable salt or a solvate thereof, wherein Y is —$NR^9$— or a bond, and $R^9$ has the same meaning as defined in the above (1).

(4) The compound according to the above (3), a pharmaceutically acceptable salt or a solvate thereof, wherein $R^9$ is hydrogen.

(5) The compound according to any one of the above (2) to (4), a pharmaceutically acceptable salt or a solvate thereof, wherein $R^3$ is a group of the formula: —V—$R^5$ wherein V is a bond and $R^5$ has the same meaning as defined in the above (1).

(6) The compound according to any one of the above (2) to (4), a pharmaceutically acceptable salt or a solvate thereof, wherein $R^3$ is a group of the formula: —V—$R^5$ wherein V is —O— and $R^5$ has the same meaning as defined in the above (1).

(7) The compound according to the above (5) or (6), a pharmaceutically acceptable salt or a solvate thereof, wherein $R^5$ is optionally substituted alkyl.

(8) The compound according to the above (6), a pharmaceutically acceptable salt or a solvate thereof, wherein $R^5$ is a group of the formula: —$CH_2$—$C(R^{10}R^{11})$—$C(=O)$—$NR^{12}R^{13}$
wherein $R^{10}$ and $R^{11}$ are each independently hydrogen, optionally substituted alkyl or halogen;
or $R^{10}$ and $R^{11}$ taken together with the carbon atom to which they are attached may form an optionally substituted ring, $R^{12}$ and $R^{13}$ are each independently hydrogen, optionally substituted amino, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle; or $R^{12}$ and $R^{13}$ taken together with the nitrogen atom to which they are attached may form an optionally substituted ring.

(9) The compound according to the above (5), a pharmaceutically acceptable salt or solvate thereof, wherein $R^5$ is methyl.

(10) The compound according to the above (1), a pharmaceutically acceptable salt or a solvate thereof, wherein R' is optionally substituted cycloalkyl or optionally substituted aryl.

(11) The compound according to the above (10), a pharmaceutically acceptable salt or a solvate thereof, wherein R' is cyclohexyl or phenyl.

(12) The compound according to the above (1), a pharmaceutically acceptable salt or a solvate thereof, wherein U is a bond.

(13) The compound according to the above (1), a pharmaceutically acceptable salt or a solvate thereof, wherein X is —S—.

(14) The compound according to the above (1), a pharmaceutically acceptable salt or a solvate thereof, wherein Z is —O—.

(15) The compound according to the above (1), a pharmaceutically acceptable salt or a solvate thereof, wherein $R^4$ is optionally substituted cycloalkyl.

(16) The compound according to the above (1), a pharmaceutically acceptable salt or a solvate thereof, wherein $R^4$ is optionally substituted phenyl or optionally substituted adamantyl.

(17) A pharmaceutical composition which comprises the compound according to any one of the above (1) to (16), a pharmaceutically acceptable salt or solvate thereof as an active ingredient.

(18) The pharmaceutical composition according to (17) for treating and/or preventing diabetes.

Moreover, the present invention provides;
(19) A method for treating and/or preventing diabetes, which comprises administering the compound of the formula (I),
(20) A use of the compound of the formula (I) in the manufacture of a pharmaceutical composition for treating and/or preventing diabetes.

The present invention is characterized in the followings.
1) Possess a 5-membered N-containing heteroring having two hetero atoms,
2) Possess a substituent (—$XUR^1$) at 4-position of the above heteroring,
3) $R^1$ is optionally substituted ring group selected from optionally substituted cycloalkyl, optionally substituted cycloalkenyl, optionally substituted aryl, optionally substituted heteroaryl or optionally substituted heterocycle,
4) One of $R^2$ and $R^3$ is a group of the formula: —$C(=O)$—Y—$R^4$,
5) $R^4$ is optionally substituted ring group selected from optionally substituted cycloalkyl, optionally substituted cycloalkenyl, optionally substituted aryl, optionally substituted heteroaryl or optionally substituted heterocycle.

Effect of the Invention

The compounds of the present invention possess an inhibitory activity to 11βhydroxysteroid dehydrogenase type 1 and the pharmaceutical compositions comprising them are very useful for a medicament, especially a medicament for treating and/or preventing hyperlipidemia, diabetes, obesity, arteriosclerosis, atherosclerosis, hyperglycemia and/or syndrome X. Moreover, the compounds of the present invention selectively inhibit 11βhydroxysteroid dehydrogenase type 1 and have a high metabolic stability, a weak drug metabolizing enzyme induction, a weak drug metabolizing enzyme inhibition or a high oral absorption, and they are especially useful for a medicament. In addition, they have a low clearance and a long half-life period for exhibiting the drug activity.

BEST MODE FOR CARRYING OUT THE INVENTION

Terms used in the description specification are explained below. Each term has the following meanings alone or together with other terms.

"Alkyl" means a $C_1$ to $C_{10}$ straight or branched alkyl group, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl, n-decyl or the like. Preferred is a C1 to C6 alkyl or a C1 to C4 alkyl, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl.

"Alkylene" means a di-valent group derived from the above "alkyl", which includes a C1 to C10 straight or branched alkylene. Preferred is methylene, ethylene, propylene, trimethylene, tetramethylene, ethylethylene, pentamethylene, hexamethylene or the like.

"Alkenyl" means a C2 to C8 straight or branched alkenyl group, which includes the above "alkyl" with one or more double bond(s). Exemplified is vinyl, 1-propenyl, 2-propenyl, 1-butenyl, 2-butenyl, 3-butenyl, 1,3-butadienyl, 3-methyl-2-butenyl or the like.

"Alkynyl" means a C2 to C8 straight or branched alkynyl group, which includes the above "alkyl" with one or more triple bond(s). Exemplified is ethynyl or the like.

"Cycloalkyl" means a C3 to C15 saturated cyclic hydrocarbon group (bridged cyclic hydrocarbon group is also included). Exemplified is cyclopropyl, cyclobutyl, cyclopentyl, cyclohexyl, cycloheptyl, cyclooctyl or bridged cyclic hydrocarbon (exemplified as follows).

[Formula 2]

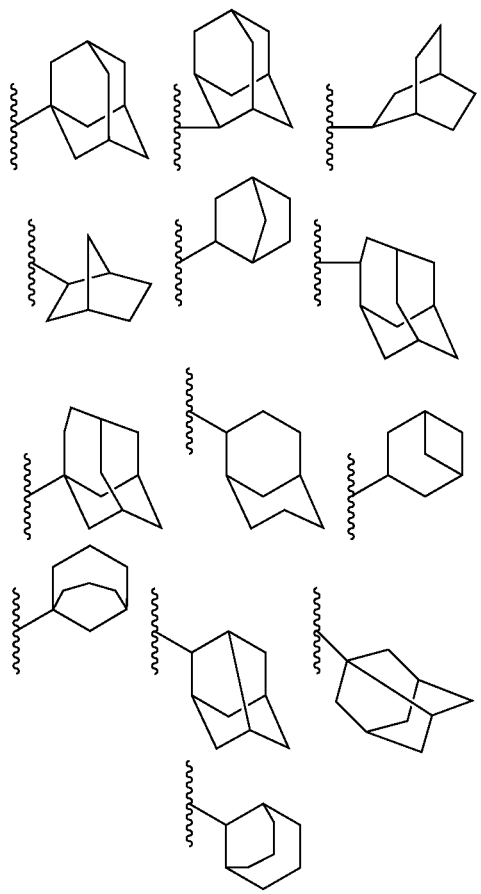

"Cycloalkenyl" means a C3 to C7 unsaturated aliphatic cyclic hydrocarbon group. Exemplified is cyclopropenyl, cyclobutenyl, cyclopentenyl, cyclohexenyl or cycloheptenyl. Preferred is cyclopropenyl, cyclobutenyl, cyclopentenyl or cyclohexenyl.

"Aryl" means a monocyclic aromatic hydrocarbon group (e.g., phenyl) or a polycyclic aromatic hydrocarbon group (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl etc.). Preferred is phenyl or naphthyl (1-naphthyl, 2-naphthyl) or the like.

"Heteroaryl" means a monocyclic aromatic heterocyclic group or fused aromatic heterocyclic is group.

The monocyclic aromatic heterocyclic group means a group derived from 5 to 8-membered aromatic heterocycle containing 1 to 4 oxygen, sulfur and/or nitrogen atom(s) in the ring. The binding bond can be at any substitutable position.

The fused aromatic heterocyclic group means a group derived from 5 to 8-membered aromatic heterocycle containing 1 to 4 oxygen, sulfur and/or nitrogen atom(s) in the ring fused with one to four of 5 to 8-membered aromatic carbocycle(s) or other 5 to 8-membered aromatic heterocycle(s). The binding bond can be at any substitutable position.

For example, it is furyl (e.g., furan-2-yl or furan-3-yl), thienyl (e.g., thiophene-2-yl or thiophene-3-yl), pyrrolyl (e.g., pyrrole-1-yl, pyrrole-2-yl or pyrrole-3-yl), imidazolyl (e.g., imidazole-1-yl, imidazole-2-yl or imidazole-4-yl), pyrazolyl (e.g., pyrazole-1-yl, pyrazole-3-yl or pyrazole-4-yl), triazolyl (e.g., 1,2,4-triazole-1-yl, 1,2,4-triazole-3-yl or 1,2,4-triazole-4-yl), tetrazolyl (e.g., tetrazole-1-yl, tetrazole-2-yl or tetrazole-5-yl), oxazolyl (e.g., oxazole-2-yl, oxazole-4-yl or oxazole-5-yl), isoxazolyl (e.g., isoxazole-3-yl, isoxazole-4-yl or isoxazole-5-yl), thiazolyl thiazole-2-yl, thiazole-4-yl or thiazole-5-yl), thiadiazolyl, isothiazolyl (e.g., isothiazole-3-yl, isothiazole-4-yl or isothiazole-5-yl), pyridyl (e.g., pyridine-2-yl, pyridine-3-yl or pyridine-4-yl), pyridazinyl (e.g., pyridazine-3-yl or pyridazine-4-yl), pyrimidinyl (e.g., pyrimidine-2-yl, pyrimidine-4-yl or pyrimidine-5-yl), furazanyl (e.g., furazan-3-yl), pyrazinyl (e.g., pyrazine-2-yl), oxadiazolyl (e.g., 1,3,4-oxadiazole-2-yl), benzofuryl (e.g., benzo[b]furan-2-yl, benzo[b]furan-3-yl, benzo[b]furan-4-yl, benzo[b]furan-5-yl, benzo[b]furan-6-yl or benzo[b]furan-7-yl), benzothienyl (e.g., benzo[b]thiophene-2-yl, benzo[b]thiophene-3-yl, benzo[b]thiophene-4-yl, benzo[b]thiophene-5-yl, benzo[b]thiophene-6-yl or benzo[b]thiophene-7-yl), benzimidazolyl (e.g., benzimidazole-1-yl, benzimidazole-2-yl, benzimidazole-4-yl or benzimidazole-5-yl), dibenzofuryl, benzoxazolyl, quinoxalyl (e.g., quinoxaline-2-yl, quinoxaline-5-yl or quinoxaline-6-yl), cinnolyl (e.g., cinnoline-3-yl, cinnoline-4-yl, cinnoline-5-yl, cinnoline-6-yl, cinnoline-7-yl or cinnoline-8-yl), quinazolyl (e.g., quinazoline-2-yl, quinazoline-4-yl, quinazoline-5-yl, quinazoline-6-yl, quinazoline-7-yl or quinazoline-8-yl), quinolyl (e.g., quinoline-2-yl, quinoline-3-yl, quinoline-4-yl, quinoline-5-yl, quinoline-6-yl, quinoline-7-yl or quinoline-8-yl), phthalazinyl (e.g., phthalazine-1-yl, phthalazine-5-yl or phthalazine-6-yl), isoquinolyl (e.g., isoquinoline-1-yl, isoquinoline-3-yl, isoquinoline-4-yl, isoquinoline-5-yl, isoquinoline-6-yl, isoquinoline-7-yl or isoquinoline-8-yl), puryl, pteridinyl (e.g., pteridine-2-yl, pteridine-4-yl, pteridine-6-yl or pteridine-7-yl), carbazolyl, phenanthridinyl, acridinyl (e.g., acridine-1-yl, acridine-2-yl, acridine-3-yl, acridine-4-yl or acridine-9-yl), indolyl (e.g., indole-1-yl, indole-2-yl, indole-3-yl, indole-4-yl, indole-5-yl, indole-6-yl or indole-7-yl), isoindolyl, phenazinyl (e.g., phenazine-1-yl or phenazine-2-yl), phenothiazinyl (e.g., phenothiazine-1-yl, phenothiazine-2-yl, phenothiazine-3-yl or phenothiazine-4-yl) or the like.

"Heterocycle" means a nonaromatic heterocycle group containing 1 to 4 oxygen, sulfur and/or nitrogen atom(s) in the ring. The binding bond can be at any substitutable position. Moreover, the nonaromatic heterocycle group can be bridged with a C1 to C4 alkylene chain and/or be fused with a cycloalkane (preferred is 5 to 6-membered ring) or a benzene ring. Heterocycle can be saturated or unsaturated, as long as it is nonaromatic. Preferred is 5 to 8-membered ring. Exemplified is 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperazinyl, 2-piperazinyl, 2-morpholinyl, 3-morpholinyl, morpholino, tetrahydropyranyl, or the following groups.

[Formula 3]

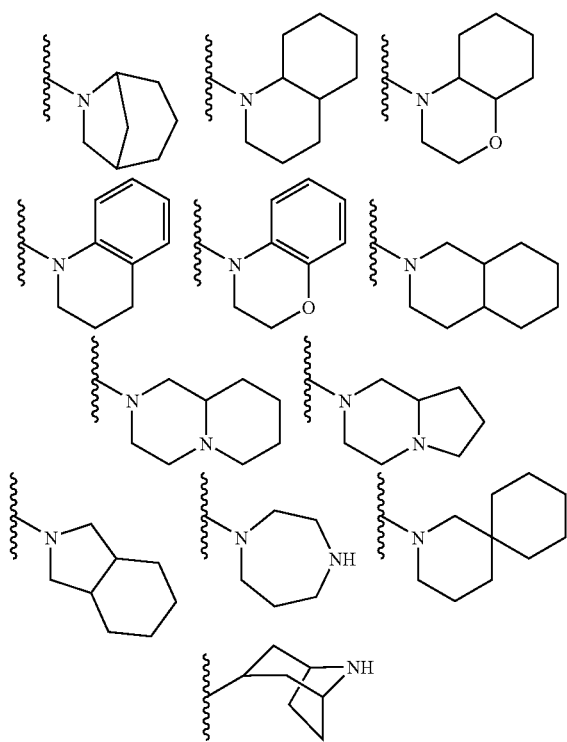

"Optionally substituted cycloalkyl", "optionally substituted cycloalkenyl", "optionally substituted aryl", "optionally substituted heteroaryl", "optionally substituted heterocycle", "optionally substituted alkyl", "optionally substituted alkylene", "optionally substituted alkenyl", "optionally substituted alkynyl", "a ring formed by taking together $R^{10}$ and $R^{11}$ with the carbon atom to which they are attached", "a ring formed by taking together $R^{12}$ and $R^{13}$ with the nitrogen atom to which they are attached" or "optionally substituted alkylthio" may be substituted with 1 to 4 substituent(s), for example, hydroxy, carboxy, halogen (e.g., F, Cl, Br, I), alkyl halide (e.g., $CF_3$, $CH_2CF_3$, $CH_2CCl_3$), alkyl (e.g., methyl, ethyl, isopropyl, tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy, butoxy), alkenyloxy (e.g., vinyloxy, allyloxy), alkoxycarbonyl (e.g., methoxycarbonyl, ethoxycarbonyl, tert-butoxycarbonyl), nitro, nitroso, optionally substituted amino (e.g., alkylamino (eg., methylamino, ethylamino, diethylamino), acylamino (e.g., acetylamino, benzoylamino), aralkylamino (e.g., benzylamino, tritylamino), hydroxyamino, alkyloxycarbonylamino, alkylsulfonylamino, optionally substituted carbamoylamino, heterocyclecarbonylamino, arylsulfonylamino, azide, aryl (e.g., phenyl), aralkyl (e.g., benzyl), cyano, isocyanate, thiocyanate, isothiocyanate, mercapto, optionally substituted alkylthio methylthio, carboxymethylthio), alkylsulfonyl (e.g., methansulfonyl, ethansulfonyl), optionally substituted carbamoyl (e.g., alkylcarbamoyl (e.g., methylcarbamoyl, ethylcarbamoyl, dimethylcarbamoyl), alkylsulfonylcarbamoyl), sulfamoyl, acyl (e.g., formyl, acetyl), formyloxy, haloformyl, oxalo, thioformyl, thiocarboxy, dithiocarboxy, thiocarbamoyl, sulfino, sulfo, sulfoamino, hydrazino, azide, ureido, amidino, guanidino, phthalimide, oxo, optionally substituted heteroaryl, optionally substituted heterocycle, alkylene, alkylenedioxy ($-O-CH_2-O-$, $-O-CH_2-CH_2-O-$, $-O-CH_2-CH_2-CH_2-O-$, or the like), optionally substituted heterocyclecarbonyl or the like.

The alkyl part of "alkoxy" and "alkylthio" is the same as the above "alkyl".

A substituent of "optionally substituted amino" and "optionally substituted carbamoyl" includes "optionally substituted alkyl", "optionally substituted alkenyl", "optionally substituted aryl", optionally substituted heteroalkyl", acyl, hydroxy or the like.

"Acyl" means formyl, optionally substituted alkylcarbonyl, optionally substituted alkenylcarbonyl, optionally substituted arylcarbonyl or optionally substituted heteroalkylcarbonyl.

"Aralkyl" means the above alkyl substituted with 1 to 3 of the above aryl.

When $R^{12}$ or $R^{13}$ is optionally substituted alkyl, optionally substituted heteroaryl, optionally substituted aryl, optionally substituted cycloalkenyl or optionally substituted heterocycle, the preferred substituent is carboxy, optionally substituted alkylthio (e.g., carboxymethylthio), optionally substituted amino, optionally substituted alkyl (e.g., carboxymethyl, piperidinylmethyl) or heterocycle.

$R^1$ is optionally substituted cycloalkyl, optionally substituted cycloalkenyl, optionally substituted aryl, optionally substituted heteroaryl or optionally substituted heterocycle. Preferably, $R^1$ is optionally substituted cycloalkyl or optionally substituted aryl, more preferably cyclohexyl or phenyl.

One of $R^2$ and $R^3$ is a group of the formula: $-C(=O)-Y-R^4$ wherein Y is $-NR^9-$, $-C(=O)-$, $-CH_2-$, a bond or $-NR^9-W-$, $R^4$ is optionally substituted cycloalkyl, optionally substituted cycloalkenyl, optionally substituted aryl, optionally substituted heteroaryl or optionally substituted heterocycle, $R^9$ is hydrogen or optionally substituted alkyl, and W is optionally substituted alkylene. Preferably, $R^2$ is a group of the formula: $-C(=O)-Y-R^4$. When $R^2$ is a group of the formula: $-C(=O)-Y-R^4$, preferably Y is $-NR^9-$ or a bond and $R^9$ is hydrogen or optionally substituted alkyl, more preferably, $-NR^9-$ wherein $R^9$ is hydrogen. As to $R^4$, optionally substituted cycloalkyl is preferable. Especially, phenyl or adamantly is more preferable as $R^4$.

The other of $R^2$ and $R^3$ is a group of the formula: $-V-R^5$, halogen or hydroxyl, wherein V is a bond, $-O-$, $-C(=O)-$, $-SO_2-$ or $-NR^6-$, $R^6$ is hydrogen or optionally substituted alkyl and $R^5$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle. Preferably, $R^3$ is a group of the formula: $-V-R^5$ wherein V is a bond or $-O-$. When V is a bond, preferably, $R^5$ is optionally substituted alkyl, more preferably methyl. When V is $-O-$, preferably $R^5$ is optionally substituted alkyl. "Optionally substituted alkyl" includes a group of the formula: $-CH_2-C(R^{10}R^{11})-C(=O)-NR^{12}R^{13}$ wherein $R^{10}$ and $R^{11}$ are each independently hydrogen, optionally substituted alkyl or halogen, or $R^{10}$ and $R^{11}$ taken together with the carbon atom to which they are attached may form an optionally substituted ring, $R^{12}$ and $R^{13}$ are each independently hydrogen, optionally substituted amino, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle, or $R^{12}$ and $R^{13}$ taken together with the nitrogen atom to which they are attached may form an optionally substituted ring.

X is a bond, —S—, —SO—, —SO$_2$—, —O—, —C≡C—, —C(=O)—, —NR$^7$—, —C(=O)—NR$^7$—, —NR$^7$—C(=O)—, —SO$_2$NR$^7$—, —CH=CH— or —NR$^7$—SO$_2$—, wherein $R^7$ is hydrogen or optionally substituted alkyl. Preferred is —S—.

U is a bond or optionally substituted alkylene, preferably a bond.

Z is —S—, —O— or —NR$^8$—, wherein $R^8$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle, or $R^8$ and $R^2$ taken together may form an optionally substituted ring. Preferred is —O—.

Among compounds of the present invention, the following embodiments are preferable.

A compound represented by the formula:

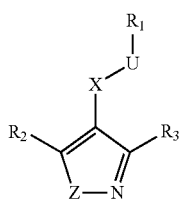

[Formula 4]

wherein $R^1$ is phenyl or cyclohexyl, $R^2$ is one selected from a group consisting of the substituent of the following formula:

[Formula 5]

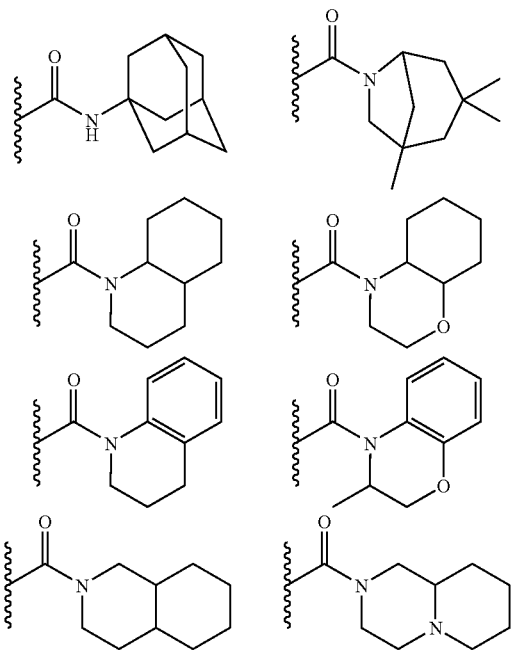

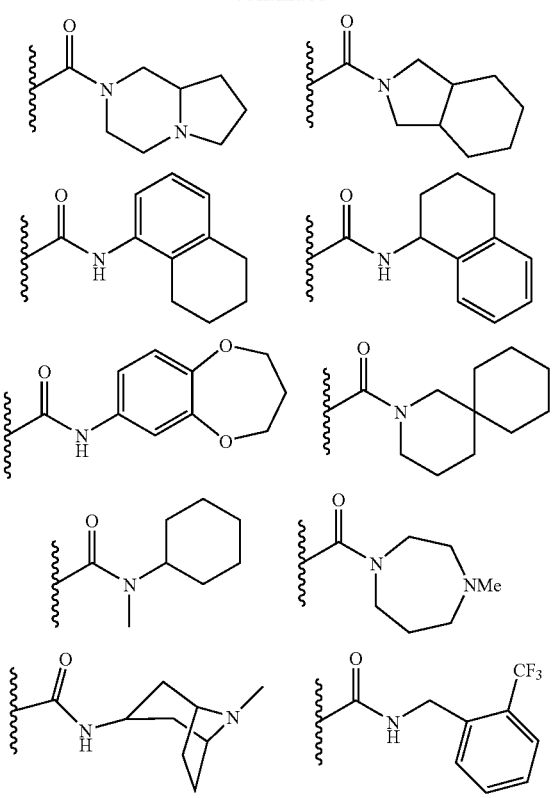

$R^3$ is Me, —OMe, —OEt, —OBn, —OCH$_2$CH$_2$OMe, —OCH$_2$CH$_2$NMe$_2$, —OCH$_2$CH$_2$NHMMe, —OCH$_2$CH$_2$NH$_2$, —NH$_2$, —NHSO$_2$Me or —NHCOMe,

X is —S—, —SO—, —SO$_2$—, —C≡C— or a bond,

U is a bond,

Z is —S—, —O—, —N(-Me)-, —NH—, —N(-Ph)- or —N(—CH$_2$CH$_2$OH)—).

In addition, among compounds of the present invention, the following embodiments are preferable as well as the above.

A compound represented by formula:

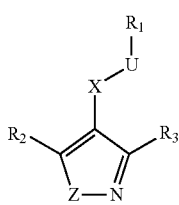

[Formula 6]

wherein $R^1$ is phenyl, $R^2$ is Me, —OMe, —OEt, —OBn, —OCH$_2$CH$_2$OMe, —OCH$_2$CH$_2$NMe$_2$, —OCH$_2$CH$_2$NHMe or —OCH$_2$CH$_2$NH$_2$, $R^3$ is one selected from a group consisting of the substituent of the following formula:

[Formula 7]

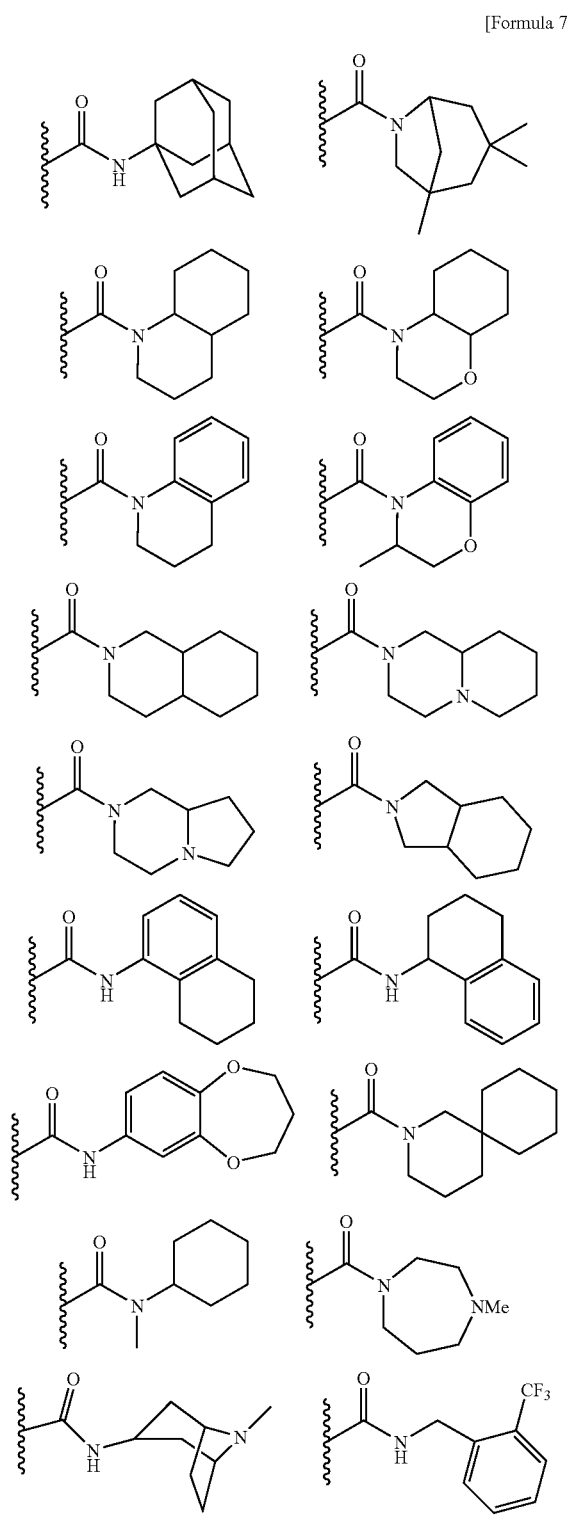

[Formula 8]

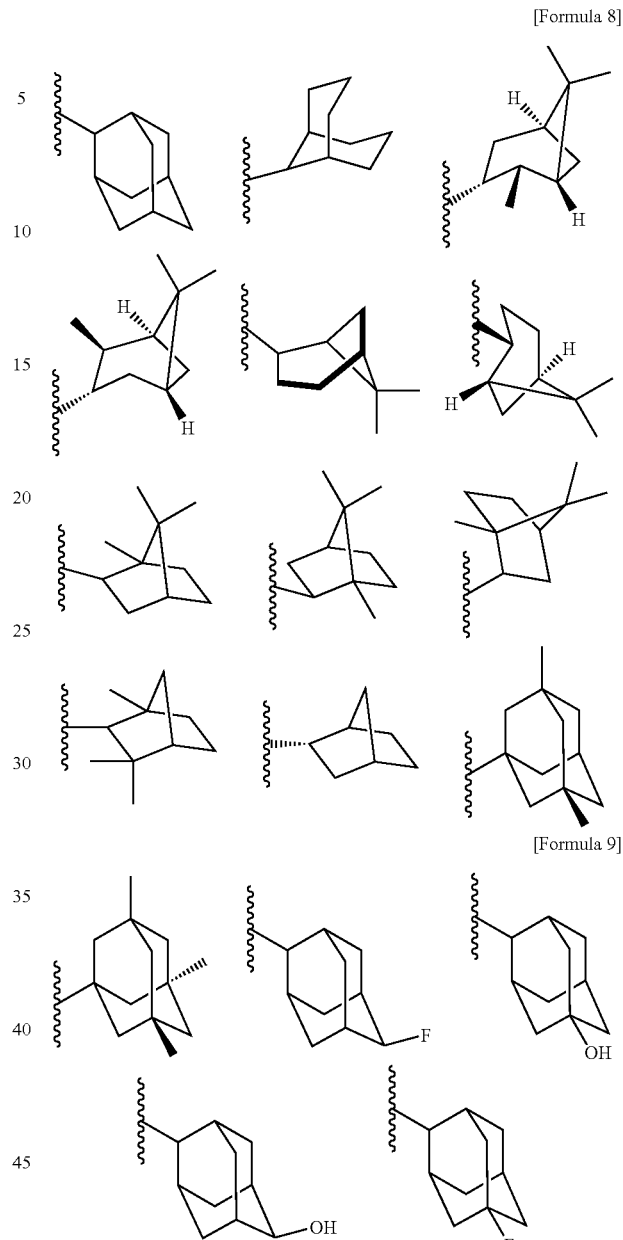

X is —S—, —SO—, —SO$_2$—, —O— or a bond,
U is a bond,
Z is —N(-Me)-, —NH—, —N(-Ph)- or —N(—CH$_2$CH$_2$OH)—).

As to optionally substituted cycloalkyl of R$^4$, for example, the following groups are preferable.

[Formula 9]

As to the substituent of optionally substituted alkyl of R$^5$, the followings are preferable. A) optionally substituted amino (the substituent is alkyl, alkyloxycarbonyl, alkylsulfonyl, optionally substituted carbamoyl (the substituent is alkyl), heterocyclecarbonyl (e.g., piperidinocarbonyl, morphorinocarbonyl), arylsulfonyl), B) optionally substituted heterocycle (e.g., 4-piperidyl, 2-pyrrolidinyl, 2-morpholinyl, piperidino, 3,5-dimethylmorpholino, piperadinyl, N-tert-butoxycarbonyl-3-piperidinyl, 1-pyrrolidinyl, tetrahydropyranyl), C) azide, D) optionally substituted carbamoyl (the substituent is alkyl, alkylsulfonyl), E) optionally substituted heterocyclecarbonyl (e.g., morpholinocarbonyl, piperidinocarbonyl, 3,5-dimethylmorphorinocarbonyl), F) carboxy, G) heteroaryl (e.g., pyridyl, imidazolyl), H) alkoxycarbonyl, I) cyano The ring formed by taking together R$^{10}$ and R$^{11}$ with the carbon atom to which they are attached means 3 to 15-membered saturated or unsaturated hydrocarbon ring or saturated or unsaturated hetero ring containing 1 to 4 oxygen, sulfur and/or nitrogen atom(s) in the hydrocarbon ring. Non aromatic ring is preferred. Exemplified is cyclopropane, cyclobutane, cyclopentane, cyclohexane, cycloheptane, cyclooctane, cyclopropane, cyclobutene, cyclopentene, cyclohexene, cycloheptene or saturated or unsaturated hetero ring containing 1 to 4 oxygen, sulfur and/or nitrogen atom(s) in the hydrocarbon ring.

As to a groups of the formula: —C($R^{10}R^{11}$)— wherein $R^{10}$ and $R^{11}$ taken together with the carbon atom to which they are attached may form a ring, the followings are exemplified.

[Formula 10]

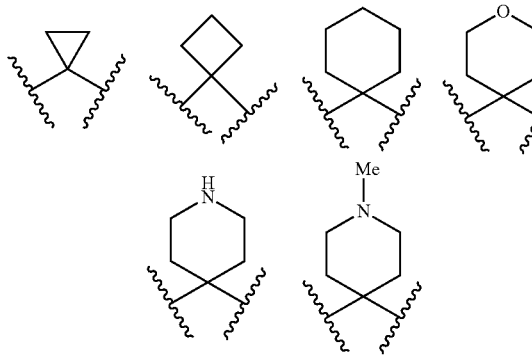

The ring formed by taking together $R^{12}$ and $R^{13}$ with the nitrogen atom to which they are attached means 3 to 15-membered saturated or unsaturated hetero ring containing 1 to 4 oxygen, sulfur and/or nitrogen atom(s) in the ring. Non aromatic ring is preferred. Exemplified is pyrrole, pyrorine, pyroridine, imidazorine, imidazoridine, pyrazoline, pyrazoridine, piperidine, piperazine or morpholine. The ring can be fused with 5-8-membered ring. For example, the ring can contain a Spiro structure.

Pharmaceutically acceptable salts of the compounds of the present invention are exemplified as follows. Basic salts, for example, are salts of alkali metal such as sodium or potassium; salts of alkaline-earth metal such as calcium or magnesium; salts of ammonium; salts of aliphatic amine such as trimethylamine, triethylamine, dicyclohexylamine, ethanolamine, diethanolamine, triethanolamine, procaine, meglumine, diethanol amine or ethylenediamine; salts of aralkyl amine such as N,N-dibenzylethylenediamine or benetamine; salts of hetero aromatic amine such as pyridine, picoline, quinoline or isoquinoline; salts of quaternary ammonium such as tetramethylammonium, tetraethylammonium, benzyltrimethylammonium, benzyltriethylammonium, benzyltributylammonium, methyltrioctylammonium or tetrabutylammonium; salts of basic amino acid such as arginine or lysine.

Acidic salts, for example, are salts of inorganic acid such as hydrochloric acid, sulfuric acid, nitric acid, phosphoric acid, carbonic acid, hythogencarbonic acid or perchloric acid; salts of organic acid such as acetic acid, propionic acid, lactic acid, maleic acid, fumaric acid, tartaric acid, malic acid, citric acid or ascorbic acid; salts of sulfonic acid such as methansulfonic acid, isethionic acid, benzenesulfonic acid or p-toluenesulfonic acid; salts of acidic amino acid such as aspartic acid or glutamic acid.

Solvate means a solvate of a compound of the present invention or a pharmaceutically acceptable salt thereof, for example, alcohol (e.g., ethanol) solvate, hydrate or the like. As to hydrate, monohydrate, dehydrates or the like are exemplified.

A method for producing a compound of the present invention is explained below. Each symbol is the same as the above (1). In addition, the treatment of the conventional organic synthesis such as extraction, purification and the like can be used for the synthesis of a compound of the present invention.

[Formula 11]

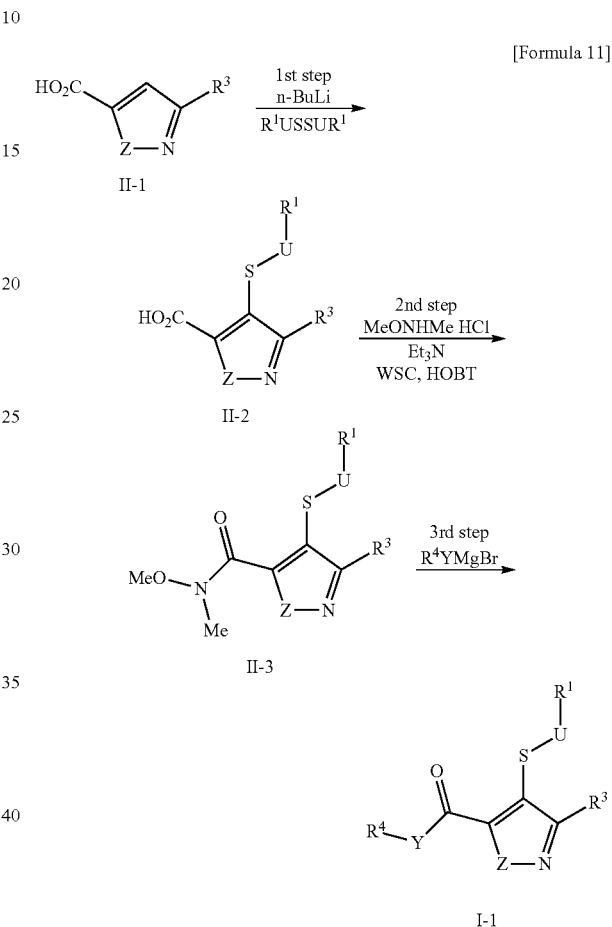

[Each symbol in the above scheme is the same as the above (1).]

$1^{st}$ Step $1^{st}$ Step is a process for manufacturing a compound of the formula (II-2) which comprises reacting a compound of formula (II-1) with disulfide ($R^1$USSU$R^1$) in the presence of a base.

Tetrahydrofuran, dioxane, diethylether or the like can be used as a solvent. The preferable reaction temperature is under 0° C., for example, at −78° C. n-Butyllithium, lithium-diisopropylamide can be used as a base.

$2^{nd}$ Step $2^{nd}$ Step is a process of manufacturing a compound of formula (II-3) which comprises reacting a compound of the formula (II-2) with N,O-dimethylhydroxylamine hydrochloride.

Chloroform, dichloromethane, N,N-dimethylformamide or the like can be used as a solvent. Triethylamine, pyridine, dimethylaminopyridine, N-methylmorphorine or the like can be used as a base. This reaction is preferably performed in the presence of 1-hydroxybenzotriazole, 1-ethyl-3-(3-dimethylaminopropyl)carbodiimide hydrochloride. The reaction temperature is under 0° C.~50° C., for example, at room temperature.

3rd Step

3rd Step is a process of manufacturing a compound of formula (I-1) which comprises reacting a compound of the formula (II-3) with R⁴YMgBr (e.g., substituted phenylmagnesiumbromide).

Tetrahydrofuran, diethylether or the like can be used as a solvent. This reaction can be preferably performed under room temperature, for example, under 0° C.

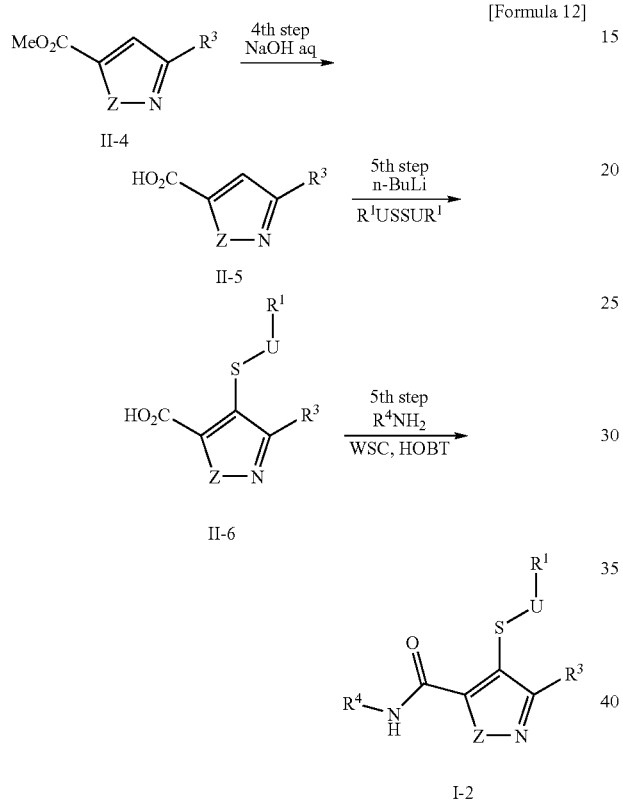

[Formula 12]

[Each symbol in the above scheme is the same as the above (1).]

4th Step

4th Step is a process of manufacturing a compound of formula (II-5) which comprises hydrolysis reaction a compound of the formula (II-4).

H₂O, hydrous alcohol (e.g., methanol solution), tetrahydrofuran or the like can be used as a solvent. Sodium hydroxide, potassium carbonate, lithium hydroxide or the like can be used as a base.

A process of manufacturing a compound of the formula (II-6) by reacting a compound of the formula (II-5) with R¹USSUR¹ in the presence of a base. Tetrahydrofuran, diethylether or the like can be used as a solvent. This reaction can be performed under 0° C., for example, −78° C. n-Butyllithium, lithiumdiisopropylamide or the like can be used as a base.

6th Step

6th Step is a process of manufacturing a compound of the formula (I-2) which comprises reacting a compound of the formula (II-6) with R⁴NH₂. Dimethylformamide, dichloromethane or the like can be used as a solvent. This reaction can be performed in the presence of 1-hydroxybenzotriazole, 1-ethyl-3-(3-dimethylaminopropyl)carbodiimide hydrochloride. This reaction can be performed at room temperature.

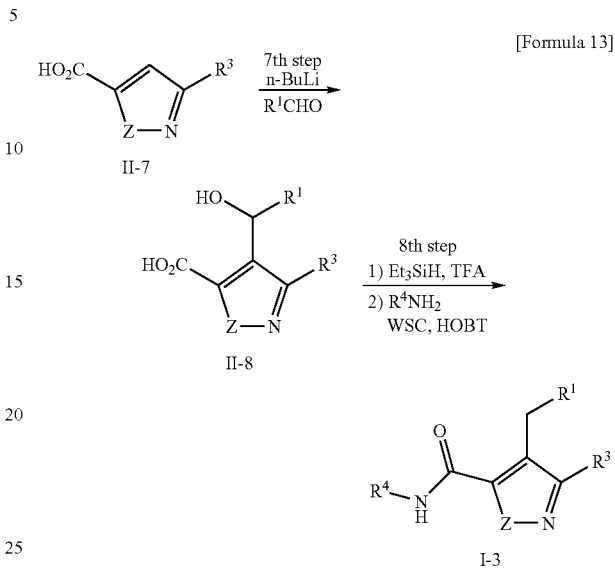

[Formula 13]

[Each symbol in the above scheme is the same as the above (1).]

7th Step

7th Step is a process of manufacturing a compound of the formula (II-8) which comprises reacting a compound of the formula (II-7) with R¹CHO in the presence of a base.

Tetrahydrofuran, diethylether, dioxane or the like can be used as a solvent. The preferable reaction temperature is under 0° C., for example, −78° C. n-Butyllithium, lithiumdiisopropylamide or the like can be used as a base.

8th Step

8th Step is a process of manufacturing a compound of the formula (I-3) which comprises reacting a compound of the formula (II-8) with triethylsilane to leave hydroxy group, followed by reacting with R⁴NH₂. Acetic acid, trifluoroacetic acid or the like can be used as a solvent for the dehydroxy process. The preferable reaction temperature of this dehydroxy process is under 0° C. In addition, the next reaction using R⁴NH can be performed at room temperature. This condensation reaction can be performed in the presence of 1-hydroxybenzotriazole, 1-ethyl-3-(3-dimethylaminopropyl)carbodiimide hydrochloride.

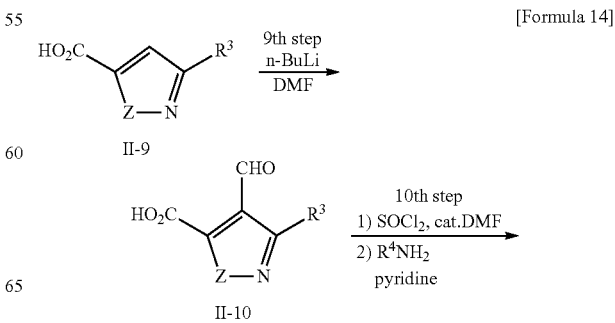

[Formula 14]

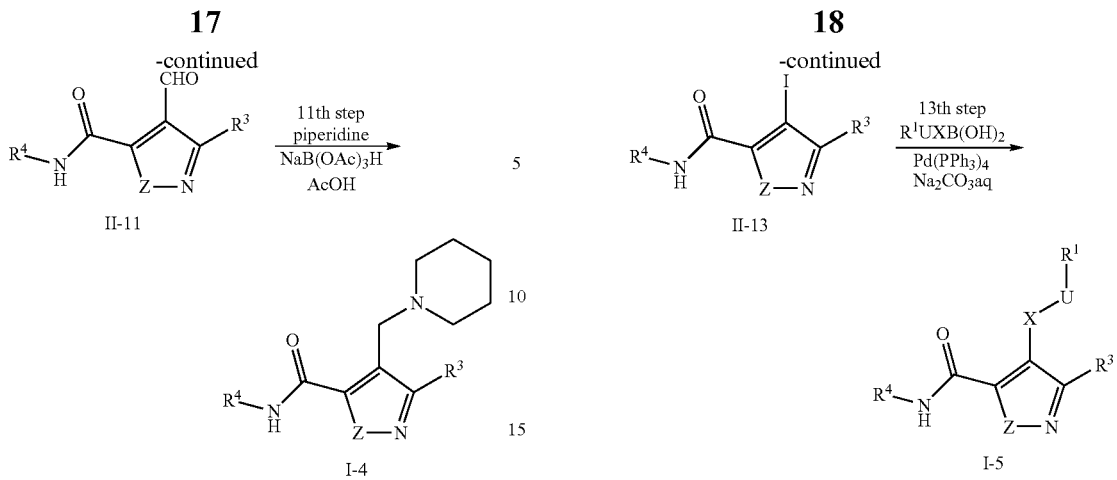

[Each symbol in the above scheme is the same as the above (1).]

9$^{th}$ Step

9$^{th}$ Step is a process of manufacturing a compound of the formula (II-10) by reacting a compound of the formula (II-9) with dimethylformamide in the presence of a base.

Tetrahydrofuran, diethylether or the like can be used as a solvent. n-Butyllithium, lithiumdiisopropylamide or the like can be used as a base. The preferable reaction temperature is under 0° C., for example, −78° C.

10$^{th}$ Step

10$^{th}$ Step is a process of manufacturing a compound of the formula (II-11) which reacting a compound of the formula (II-10) with thionyl chloride, followed by reacting with R$^4$NH$_2$.

Toluene, xylene, tetrahydrofuran, dichloromethane or the like can be used as a solvent. The reaction with thionyl chloride can be preferably performed in the presence of catalytic amount of dimethylformamide. This reaction can be performed above room temperature. For example, this reaction can be performed at 70° C. After production of acid chloride, the reaction mixture is cooled, then reacting with R$^4$NH$_2$. This reaction can be preferably performed in the presence of a base. Pyridine, dimethylaminopyridine, triethylamine, N-methylmorphorine or the like can be used as a base.

11$^{th}$ Step

11$^{th}$ Step is a process of manufacturing a compound of the formula (I-4) which reacting a compound of the formula (II-11) with piperidine to form Schiff base, then reducing it by a reducing agent.

Chloroform, dichloromethane or the like can be used as a solvent. This reaction can be preferably performed in the presence of catalytic amount of acid (e.g., acetic acid). Sodium triacetoxy borohydride, sodium cyanoborohydride or the like can be used as a reducing agent. This reaction can be performed at room temperature. In addition, a compound having amino group can be used instead of piperidine for manufacturing a compound of the present invention other than a compound of the formula (I-4).

[Formula 15]

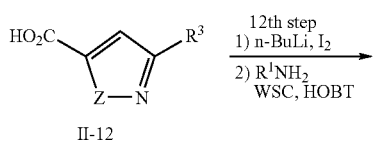

[Each symbol in the above scheme is the same as the above (1).]

12$^{th}$ Step

12$^{th}$ Step is a process of manufacturing a compound of the formula (II-13) which comprises reacting a compound of the formula (II-12) with iodine, then reacting with R$^4$NH$_2$. This reaction can be preferably performed in the presence of a base. n-Butyllithium, lithiumdiisopropylamide or the like can be used as a base. Tetrahydrofuran, diethylether or the like can be used as a solvent. The preferable reaction temperature is under 0° C., for example, −78° C.

The condensation process of reacting with R$^4$NH$_2$ can be performed under the same condition described in the above.

13$^{th}$ Step

13$^{th}$ Step is a process of manufacturing a compound of the formula (I-5) which comprises putting a compound of formula (II-13) in Suzuki-coupling. Dioxane (hydrous dioxane), dimethylformamide, tetrahydrofuran, dimethoxyethane or the like can be used as a solvent.

This reaction can be performed in the presence of tetrakis (triphenylphosphine)palladium and a base (e.g., sodium carbonate, cesium carbonate, potassium phosphate, tribasic or the like) by reacting with R$^1$UXB(OH)$_2$ (e.g., substituted phenyl boric acid). This reaction can be performed at room temperature or under refluxing.

[Formula 16]

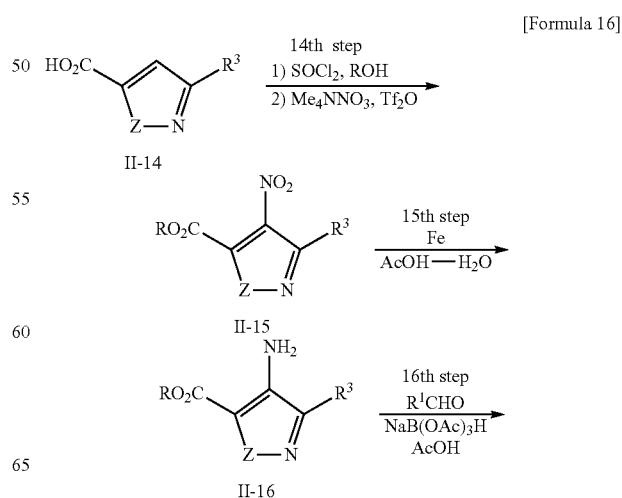

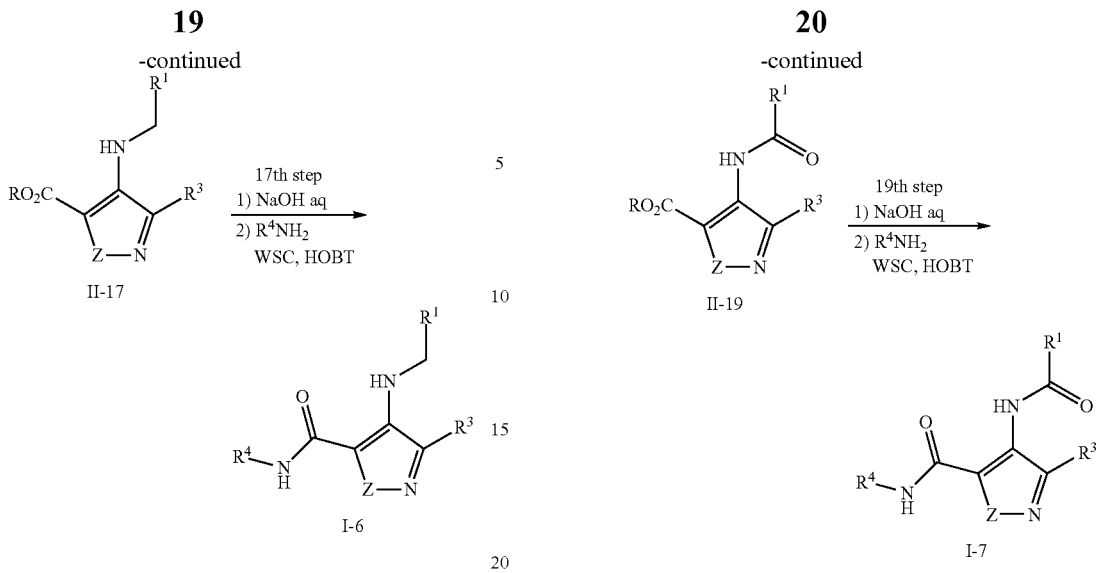

[Each symbol in the above scheme is the same as the above (1).]

14th Step

14th Step is a process of manufacturing a compound of the formula (II-15) which reacting a compound of the formula (II-14) with thionyl chloride in an alcohol to produce ester, then reacting with tetramethylammonium nitrate in the presence of trifluoromethanesulfonic acid anhydride. Methanol, ethanol or the like can be used as an alcohol. A process of manufacturing of ester can be performed above room temperature, for example at 50° C.

Dichloromethane, chloroform or the like can be used as a solvent for the reaction of introduction of nitro group. This reaction can be performed under refluxing.

15th Step

15th Step is a process of manufacturing a compound of the formula (II-16) which reducing a compound of the formula (II-15). This reaction can be performed by using iron powder, zinc or stannum in the presence of hydrous acetic acid. This reaction can be performed under refluxing.

16th Step

16th Step is a process of manufacturing a compound of the formula (II-17) which comprises reacting a compound of the formula (II-16) with $R^1CHO$ to form Schiff base, then reducing it by a reducing agent.

Chloroform, dichloromethane or the like can be used as a solvent. This reaction can be preferably performed in the presence of catalytic amount of acid (e.g., acetic acid). Sodium triacetoxy borohydride, sodium cyanoborohydride or the like can be used as a reducing agent.

17th Step

17th Step is a process of manufacturing a compound of the formula (I-6) which comprises hydrolyzing a compound of the formula (II-17), then condensing the obtained compound with $R^4NH_2$. The condition of each step is the same described in the above.

[Formula 17]

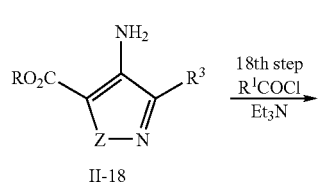

[Each symbol in the above scheme is the same as the above (1).]

18th Step

18th Step is a process of manufacturing a compound of the formula (II-19) which comprises reacting a compound of the formula (II-18) with $R^1COCl$ in the presence of a base.

Toluene, dichloromethane or the like can be used as a solvent. Triethylamine, pyridine, N-methylmorphorine or the like can be used as a base. This reaction can be performed at room temperature.

19th Step

19th Step is a process of manufacturing a compound of the formula (I-7) which hydrolyzing an ester part a compound of the formula (II-19) in the presence of a base, then reacting the obtained compound with $R^4NH_2$. This reaction can be performed by conventional hydrolysis or condensation condition.

[Formula 18]

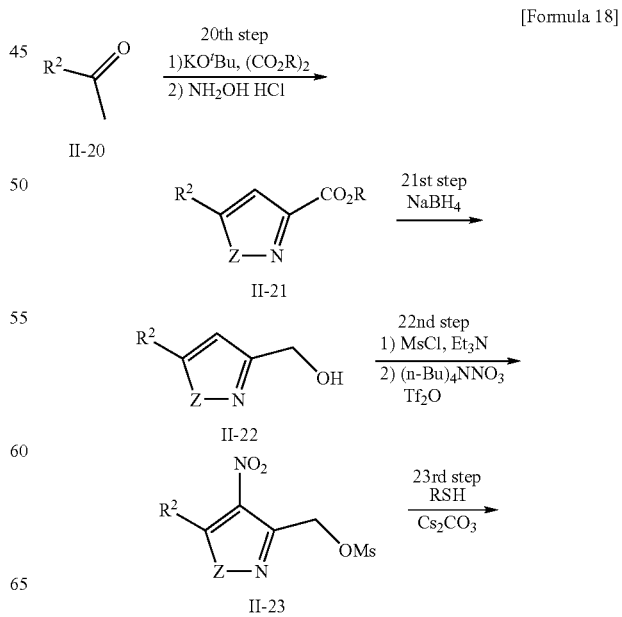

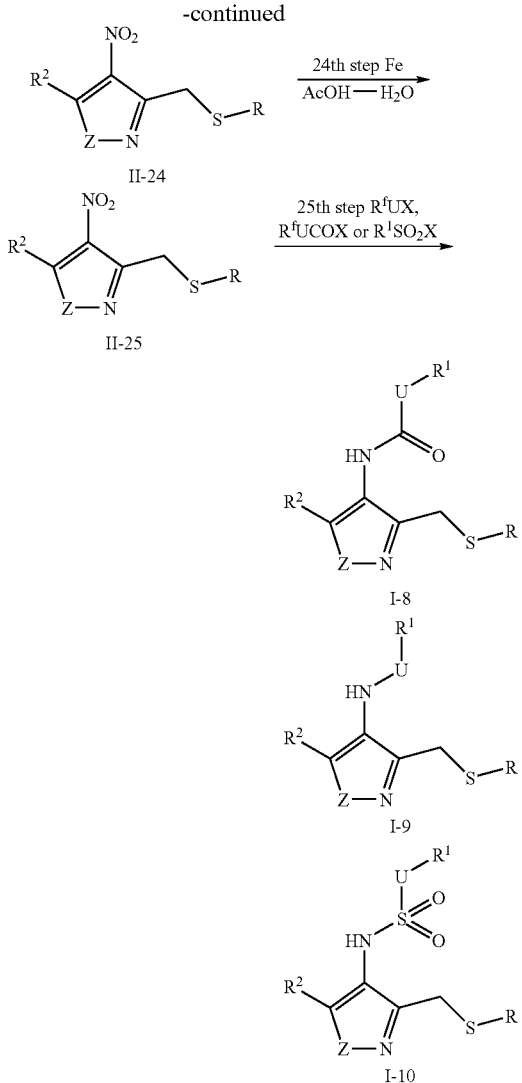

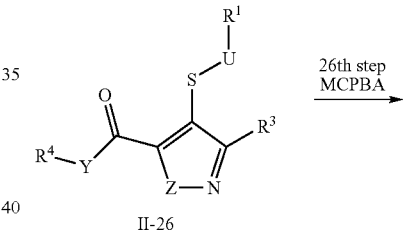

[Each symbol in the above scheme is the same as the above (1).]

20th Step

20th Step is a process of manufacturing a compound of the formula (II-21) which comprises reacting a compound of the formula (II-20) with diethyl oxalate in the presence of a base, then reacting the obtained compound with hydroxylamine hydrochloride.

Potassium t-butoxide or the like can be used as a base. This reaction can be performed at 0° C. Tetrahydrofuran can be used as a solvent.

The reaction with hydroxylamine can be performed at room temperature or under refluxing.

21st Step

21st Step is a process of manufacturing a compound of the formula (II-22) which reducing a compound of the formula (II-21).

Sodium borohydride, lithium aluminum hydride or the like can be used as a reducing agent. A mixture of ethanol and tetrahydrofuran, tetrahydrofuran can be used as a solvent.

22nd Step

22nd Step is a process of manufacturing a compound of the formula (II-23) which comprises mesylating a compound of the formula (II-22), then nitrating the obtained compound.

Mesylation can be performed at room temperature or at 0° C. Toluene, xylene, dimethylformamide, tetrahydrofuran, dichloromethane or the like can be used as a solvent. Methanesulfonyl chloride or the like can be used as a mesylation agent.

Nitration can be performed under the same condition described in the above.

23rd Step

23rd Step is a process of manufacturing a compound of the formula (II-24) which comprises reacting a compound of the formula (II-23) with RSH.

Acetonitrile or the like can be used as a solvent. This reaction can be preferably performed in the presence of cesium carbonate. This reaction can be performed at room temperature.

24rd Step

24th Step is a process of manufacturing a compound of the formula (II-25) which comprises reducing a compound of the formula (II-24). The reduction condition of nitro group is the same described in the above.

A compound of the formula (II-25) obtained by following the above scheme has a free amino group and is useful as an intermediate for manufacturing a compound of the present invention. Various compounds of the present invention can be manufactured by modifying of an amino group. A compound of the formula (I-8), a compound of the formula (I-9), a compound of the formula (I-10) or the like can be manufactured as the amide derivatives. In addition, sulfonamide derivatives or the like can be manufactured.

[Formula 19]

[Each symbol in the above scheme is the same as the above (1).]

26th Step

26th Step is a process of manufacturing a compound of the formula (I-11) which comprises oxidizing a compound of the formula (II-26). Tetrahydrofuran, dichloromethane or the like can be used as a solvent. m-chloroperbenzoic acid can be used as a oxidant. This reaction can be performed at room temperature or above room temperature, for example at 50° C.

Various substituent of a compound of the present invention can be introduced referring to (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS, or the like.

A compound of the present invention has the high inhibitory activity to 11βhydroxysteroid dehydrogenase type 1. Therefore, a compound of the present invention can be used for a disease concerning 11βhydroxysteroid dehydrogenase type 1, especially, used for treating and/or preventing hyperlipidemia, diabetes, obesity, arteriosclerosis, atherosclerosis, hyperglycemia and/or syndrome X. Especially, a compound of the present invention is useful for treating and/or preventing diabetes.

A compound of the present invention can be administrated via oral or parenteral. In case of oral administration, a compound of the present invention can be used for in any form of the conventional pharmaceutical formulations, for example, solid formulations such as tablets, powders, granules, capsules or the like; aqueous formulations; oleaginous suspensions; or solution formulations such as syrup or elixir. In case of parenteral administration, a compound of the present invention can be used as an aqueous or oleaginous suspensions injection, or nose droops. In the preparation of such formulations, the conventional pharmaceutical excipients, binding agents, lubricants, aqueous solvents, oleaginous solvents, emulsifying agents, suspending agents, preservatives, stabilizers, and the like can be optionally used. Especially, a compound of the present invention is preferably used as oral agents.

A formulation according to the present invention can be manufactured by combining (e.g., admixing) a curatively effective amount of a compound of the present invention with a pharmaceutically acceptable carrier or diluent. The formulation can be manufactured by using of well-known and easily available ingredients in accordance with a known method.

A dosage of a compound of the present invention depends on the administration route, age, body weight, conditions of the patient, and kind of disease, but in case of oral administration, the daily dosage for an adult can be between approximately 0.05 mg~3000 mg, preferably approximately 0.1 mg~1000 mg. The daily dosage can be administered in divisions. In case of parenteral administration, the daily dosage for an adult can be between approximately 0.01 mg~1000 mg, preferably approximately 0.05 mg~500 mg. Moreover, a compound of the present invention can be administered with other curative agents.

This invention is further explained by the following Examples, which are not intended to limit the scope of the present invention.

Example 1

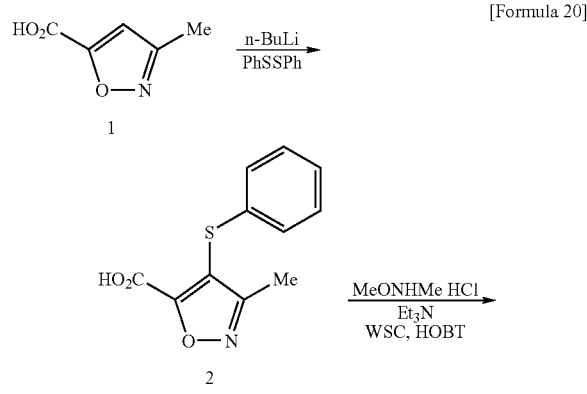

[Formula 20]

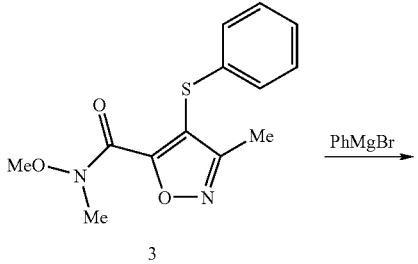

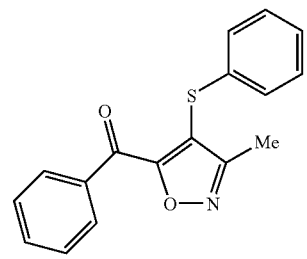

To a solution of 1 (5 g) in THF (100 mL) was added n-Butyllithium (3.19 mL, 2.71M hexane solution) at −78° C. under $N_2$ atmosphere, then the reaction solution was allowed warm up to −30° C. After cooling again to −78° C., diphenylsulfide (10.31 g) in THF (40 mL) was added to the reaction solution. After termination of this reaction, dilute hydrochloric acid was added to the solution. The solution was partitioned between water and $Et_2O$, extracted with $Et_2O$ and washed with brine. The extraction was back extracted with sat.$NaHCO_3$ soln. and the back extraction was washed with $Et_2O$. It was neutralized with conc.HCl and the resulting precipitates were collected by filtration and washed with water to give 2 (6.41 g).

To a solution of 2 (1.5 g) in $CHCl_3$ (15 mL) were added N,O-dimethylhydroxylamine hydrochloride (808 mg), triethylamine (1.33 mL), 1-hydroxy-benzotriazole (1.03 g) and 1-Ethyl-3-(3-dimethylaminopropyl)-carbodiimide hydrochloride (1.47 g) under NT, atmosphere and the resulting solution was stirred at room temp. After termination of this reaction, the reaction solution was diluted with $CHCl_3$ and washed with water, sat.$NaHCO_3$ soln., 2N—HCl soln., sat.$NaHCO_3$ soln. and brine, successively. After dryness by $MgSO_4$, the organic phase was concentrated in vacuo and the residue was purified by silicagel columnchromatography to give 3 (1.06 g).

To a solution of 3 (200 mg) in THF (3 mL) was added phenylmagnesiumbromide (1.08 mL, 1M THF solution) at 0° C. under $N_2$ atmosphere. After termination of this reaction, dilute hydrochloric acid was added to the solution. The solution was partitioned between water and EtOAc, extracted with EtOAc. The extraction was washed with sat.$NaHCO_3$ soln. and brine, then dried with $MgSO_4$ and concentrated in vacuo. The residue was purified by silicagel columnchromatography to give 4 (A-9)(188 mg).

Example 2

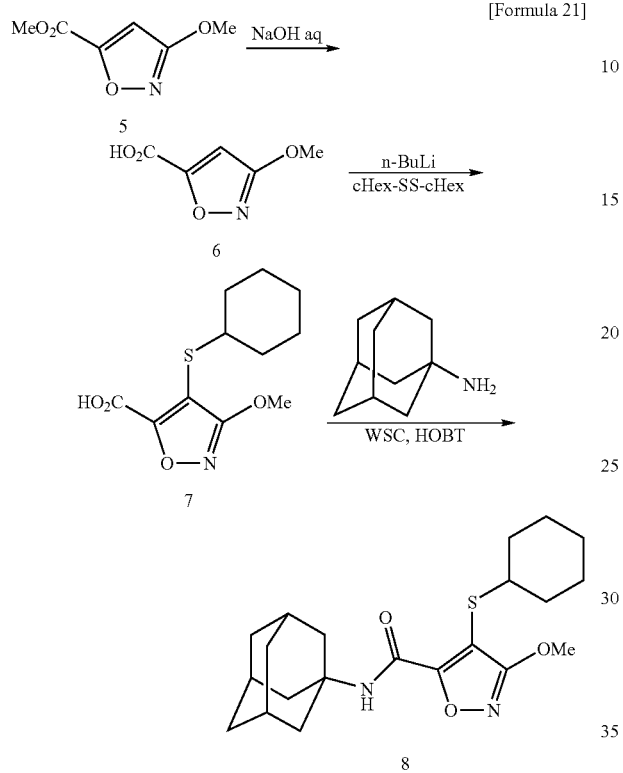

[Formula 21]

To a solution of 5 (890 mg) in MeOH (20 mL) was added 2N NaOH soln. (3.12 mL) at 0° C. After termination of this reaction, the reaction solution was neutralized with 2N HCl soln. and MeOH was removed under reduced pressure. The residue was diluted with CHCl₃ and partitioned between water and CHCl₃ and extracted with CHCl₃. The extraction was washed with brine, dried with MgSO₄ and concentrated in vacuo to give 6 (643 mL).

To a solution of 6 (400 mg) in THF (15 mL) was added n-Butyllithium (3.89 mL, 1.58M hexane solution) at −78° C. under N₂ atmosphere, then the reaction solution was allowed warm up to −30° C. After cooling again to −78° C., dicyclohexyldisulfide (773 mg) in THF (4 mL) was added to the reaction solution. After termination of this reaction, dilute hydrochloric acid was added to the solution. The solution was partitioned between water and Et₂O, extracted with Et₂O and washed with brine. The extraction was back extracted with sat.NaHCO₃ soln. and the back extraction was washed with Et₂O. It was neutralized with conc.HCl, extracted with Et₂O, washed with brine, dried with MgSO₄ and concentrated in vacuo to give 7 (309 mg).

To a solution of 7 (100 mg) in DMF (3 mL) were added 1-adamantanamine (88.2 mg), 1-hydroxybenzotriazole (78.8 mg) and 1-Ethyl-3-(3-dimethyl-aminopropyl)-carbodiimide hydrochloride (112 mg) under N₂ atmosphere, and the resulting solution was stirred at room temp. After termination of this reaction, the reaction solution was partitioned between 2N HCl soln. and EtOAc and extracted with EtOAc. The extraction was washed with 2N HCl soln., sat.NaHCO₃ soln., brine successively, then dried with MgSO₄ and concentrated in vacuo. The residue was purified by silicagel columnchromatography to give 8 (A-19)(65 mg).

Example 3

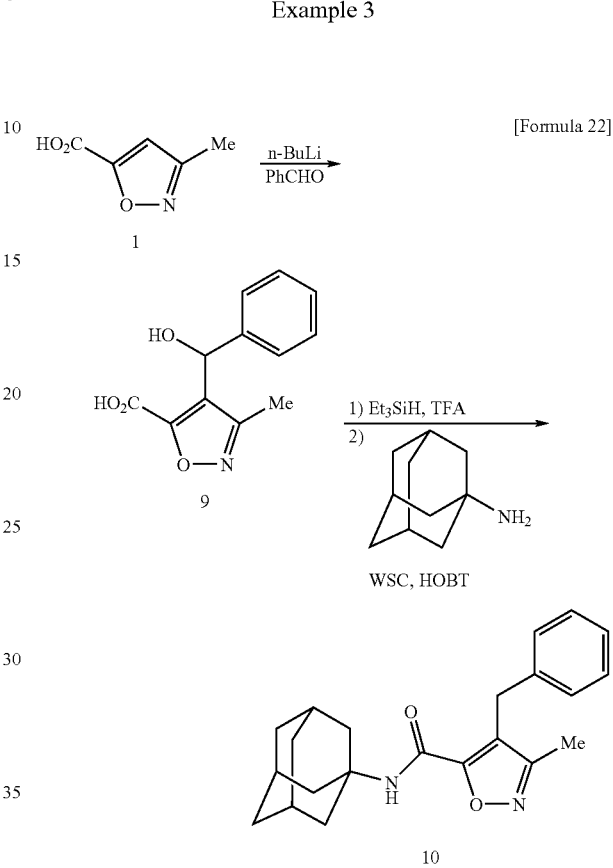

[Formula 22]

To a solution of 1 (2 g) in THF (40 mL) was added n-Butyllithium (12.8 mL, 2.71M hexane solution) at −78° C. under N₂ atmosphere, then the reaction solution was allowed warm up to −30° C. After cooling again to −78° C., benzaldehyde (1.76 mL) in THF (10 mL) was added to the reaction solution. After termination of this reaction, dilute hydrochloric acid was added to the solution. The solution was partitioned between water and Et₂O, extracted with Et₂O and washed with brine. The extraction was back extracted with sat-.NaHCO₃ soln. and the back extraction was washed with Et₂O. It was neutralized with conc.HCl, extracted with Et₂O, washed with brine, dried with MgSO₄ and concentrated in vacuo to give 9 (2.81 g).

To a solution of 9 (100 mg) in trifluoroacetic acid solution (2 mL) was added triethylsilane (137 μL) at 0° C. under N₂ atmosphere and the resulting solution was stirred at room temp. After termination of this reaction, trifluoroacetic acid was removed under reduced pressure. The residue was dissolved in DMF (2 mL). 1-adamantanamine (97.3 mg), 1-hydroxybenzotriazole (86.9 mg) and 1-Ethyl-3-(3-dimethylaminopropyl)-carbodiimide hydrochloride (123 mg) were added to the solution and the mixture was stirred at room temp. After termination of this reaction, the mixture was partitioned between 2N HCl soln. and EtOAc, and extracted with EtOAc. The extraction was washed with 2N HCl soln., sat.NaHCO₃ soln., brine successively then dried with MgSO₄

Example 4

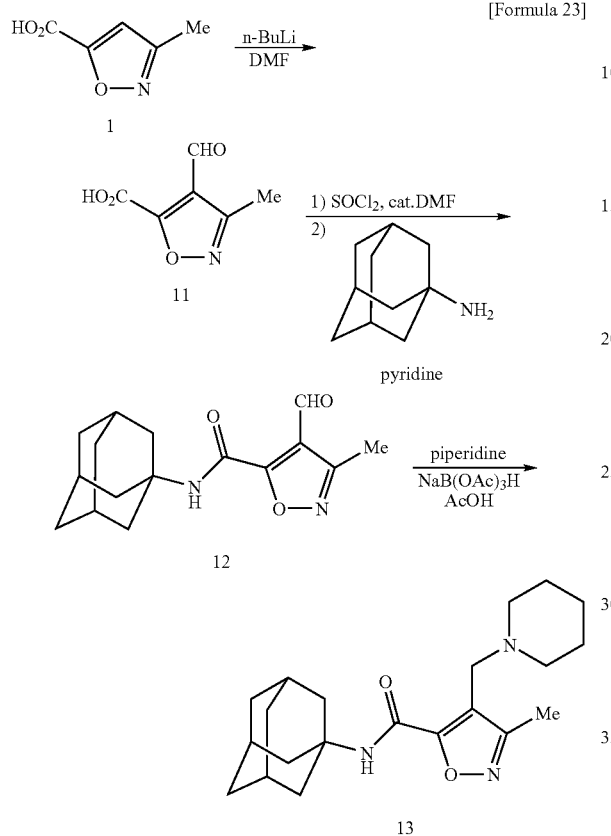

To a solution of 1 (3 g) in THF (60 mL) was added n-Butyllithium (32.9 mL, 1.58M hexane solution) at –78° C. under N₂ atmosphere, then the reaction solution was allowed warm up to –30° C. After cooling again to –78° C., dimethylformamide (3.66 mL) in THF (10 mL) was added to the reaction solution and allowed warm up to 0° C. After termination of this reaction, dilute hydrochloric acid was added to the solution. The solution was partitioned between water and Et₂O, extracted with Et₂O and washed with brine. The extraction was back extracted with sat.NaHCO₃ soln. and the back extraction was washed with Et₂O. It was neutralized with conc.HCl, extracted with Et₂O, washed with brine, dried with MgSO₄ and concentrated in vacuo to give 11 (2.32 g).

To a solution of 11 (500 mg) in toluene (10 mL) were added thionyl chloride (0.47 mL) and dimethylformamide (100 μL), and the resulting solution was stirred at 70° C. After removal of toluene under reduced pressure, the residue was dissolved in pyridine (10 mL). 1-adamantanamine (97.3 mg) was added to the solution under N₂ atmosphere, and the resulting solution was stirred at room temp. After termination of this reaction, pyridine was removed under reduced pressure and the residue was diluted with EtOAc. The solution was partitioned between 2N HCl soln. and EtOAc and extracted with EtOAc. The extraction was washed with sat.NaHCO₃ soln., brine successively, then dried with MgSO₄ and concentrated in vacuo. The residue was purified by silicagel columnchromatography to give 12 (341 mg).

To a solution of 12 (100 mg) in CHCl₃ (2 mL) were added piperidine (68.7 μL), acetic acid (6 μL) and sodium triacetoxy borohydride (110 mg) under N₂ atmosphere, and the resulting mixture was stirred at room temp. After termination of this reaction, sat.NaHCO₃ soln. was added to the mixture. The solution was partitioned between water and EtOAc and extracted with EtOAc. The extraction was washed with brine, dried with MgSO₄ and concentrated in vacuo. The residue was purified by silicagel columnchromatography to give 13 (A-23)(95 mg).

Example 5

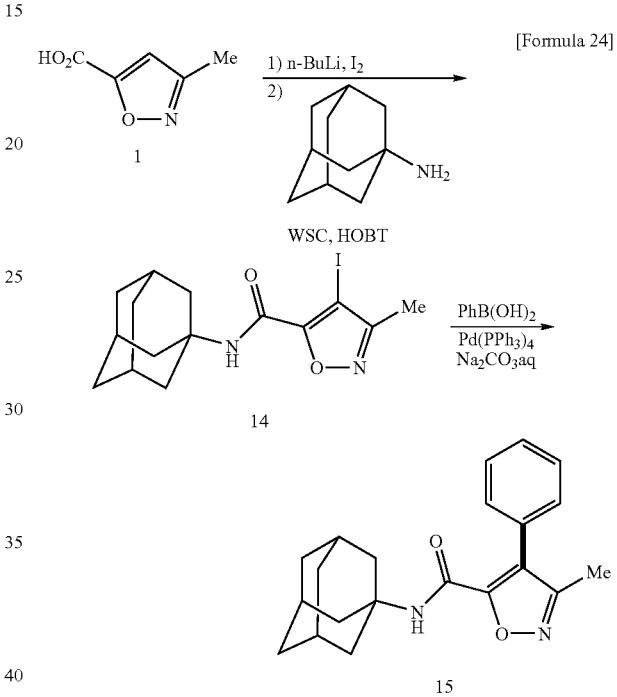

To a solution of 1 (1 g) in THF (30 mL) was added n-Butyllithium (6.39 mL, 2.71M hexane solution) at –78° C. under N₂ atmosphere, then the reaction solution was allowed warm up to –30° C. After cooling again to –78° C., iodine (2.4 g) in THF (20 mL) was added to the reaction solution. After termination of this reaction, dilute hydrochloric acid was added to the solution. The solution was partitioned between water and EtOAc, extracted with EtOAc and washed with sodium thiosulfate soln., water and brine. The extraction was dried with MgSO₄ and concentrated in vacuo. To a solution of the residue in DMF (25 mL) were added 1-adamantanamine (1.43 g), 1-hydroxybenzotriazole (1.28 g) and 1-Ethyl-3-(3-dimethylaminopropyl)-carbodiimide hydrochloride (1.81 g), the resulting solution was stirred at room temp. After termination of this reaction, the mixture was partitioned between 2N HCl soln. and EtOAc, and extracted with EtOAc. The extraction was washed with 2N HCl soln., sat.NaHCO₃ soln., brine successively then dried with MgSO₄ and concentrated in vacuo. The residue was purified by silicagel columnchromatography to give 14 (2.47 g).

To a solution of 14 (100 mg) in dioxane (1.5 mL) were added phenyl boronic acid (37.9 mg), tetrakis-(triphenylphosphine)-palladium (15 mg) and 1M Na₂CO₃ (0.388 mL), and the resulting solution was stirred at 100° C. After termination of this reaction, the solution was cooled to room temp., then partitioned between sat. NaHCO₃ soln. and EtOAc, extracted with EtOAc. The extraction was washed with brine and dried with MgSO₄ and concentrated in vacuo. The residue was purified by silicagel columnchromatography to give 15 (A-24)(79 mg).

Example 6

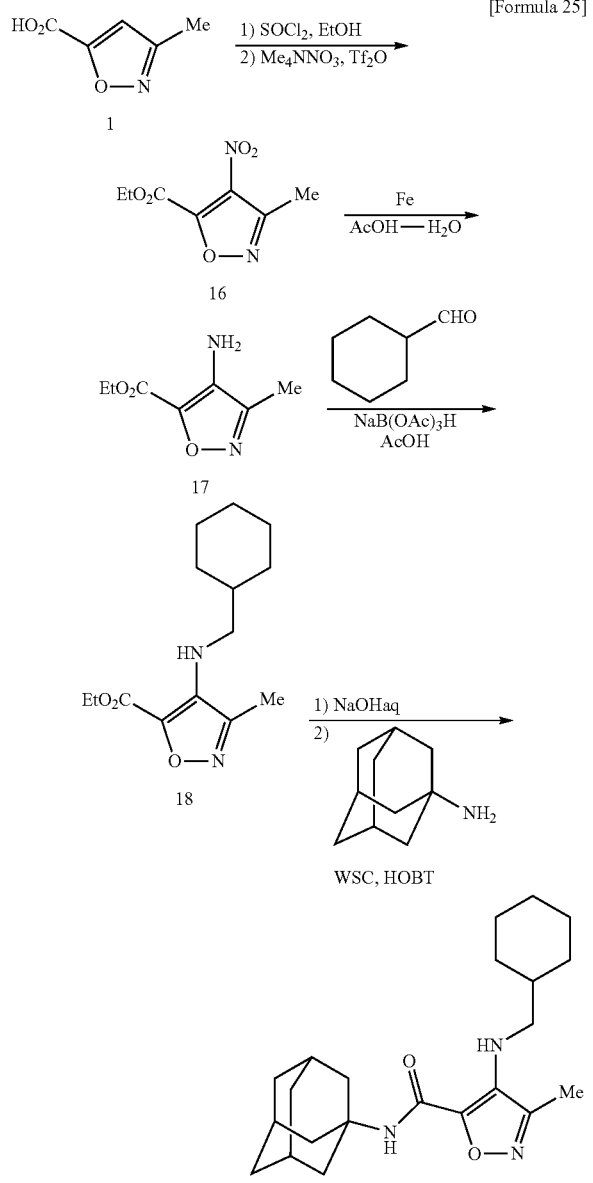

To a solution of 1 (5 g) in EtOH (100 mL) was added thionyl chloride (3.44 mL), and the resulting solution was stirred at 50° C. After termination of this reaction, the solution was cooled to room temp. and the volatile was removed under reduced pressure. The residue was dissolved in EtOAc and partitioned between Na₂CO₃ soln. and EtOAc, then extracted with EtOAc. The extraction was washed with water, brine and dried with MgSO₄ and concentrated in vacuo to give ethylester (6.3 g). To a solution of tetramethylammonium nitrate (6.81 g) in CH₂Cl₂ (40 mL) was added trifluoromethanesulfonic acid anhydride (8.41 mL). Ethylester (5.17 g) in CH₂Cl₂ (15 ml) was added to the solution and the resulting mixture was refluxed overnight. The reaction mixture was cooled to room temp. and added sat. NaHCO₃ soln., then partitioned between water and EtOAc and extracted with EtOAc. The extraction was washed with water and brine, dried with MgSO₄ and concentrated in vacuo. The residue was purified by silicagel columnchromatography to give 16 (5.38 g).

To a solution of 16 (4 g) in AcOH (60 mL)/H₂O (20 mL) was added Fe powder (5.58 g) under N₂ atmosphere and the resulting solution was stirred at 50° C. After termination of this reaction, the solution was cooled to room temp. and the volatile was removed under reduced pressure. The residue was dissolved in EtOAc and sat.NaHCO₃ soln. was added to the mixture. The solution was partitioned between water and EtOAc and extracted with EtOAc. The extraction was washed with brine, dried with MgSO₄ and concentrated in vacuo. The residue was purified by silicagel columnchromatography to give 17 (2.03 g).

To a solution of 17 (100 mg) in CHCl₃ (2 mL) were added cyclohexanecarboxyaldehyde (107 µL), AcOH (10.1 µL) and sodium triacetoxy borohydride (187 mg) under N₂ atmosphere and the resulting solution was stirred at 70° C. After termination of this reaction, the solution was cooled to room temp. and sat.NaHCO₃ soln. was added to the mixture. The solution was partitioned between H₂O and EtOAc and extracted with EtOAc. The extraction was washed with brine, dried with MgSO₄ and concentrated in vacuo. The residue was purified by silicagel columnchromatography to give 18 (88 mg).

To a solution of 18 (80 mg) in MeOH (2 mL) was added 2N NaOH soln. (150 µL) at 0° C. and the resulting solution was stirred at rt. Additional 2N NaOH soln. (30 µL) was added to the mixture and the resulting solution was stirred at 40° C. After termination of this reaction, the solution was neutralized with 2N HCl soln. and diluted with CHCl₃ and dried with MgSO₄ and concentrated in vacuo. To a solution of the residue in DMF (4 mL) were added 1-adamantanamine (227 mg), 1-hydroxybenzotriazole (60.9 mg) and 1-Ethyl-3-(3-dimethylaminopropyl)-carbodiimide hydrochloride (86.4 mg) were added to the solution and the mixture was stirred at 60° C. overnight. The reaction mixture was cooled to room temp. and partitioned between water and EtOAc and extracted with EtOAc. The extraction was washed with water, brine and dried with MgSO₄ and concentrated in vacuo. The residue was purified by silicagel columnchromatography to give 19 (A-25)(59 mg).

Example 7

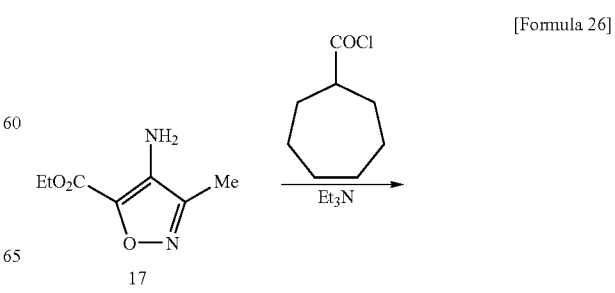

-continued

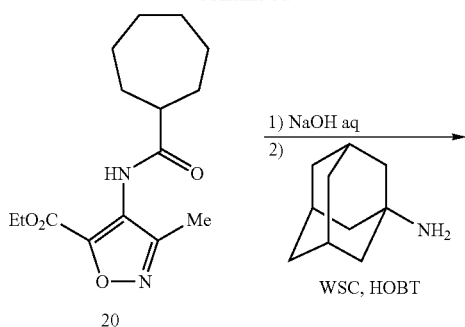

Example 8

[Formula 27]

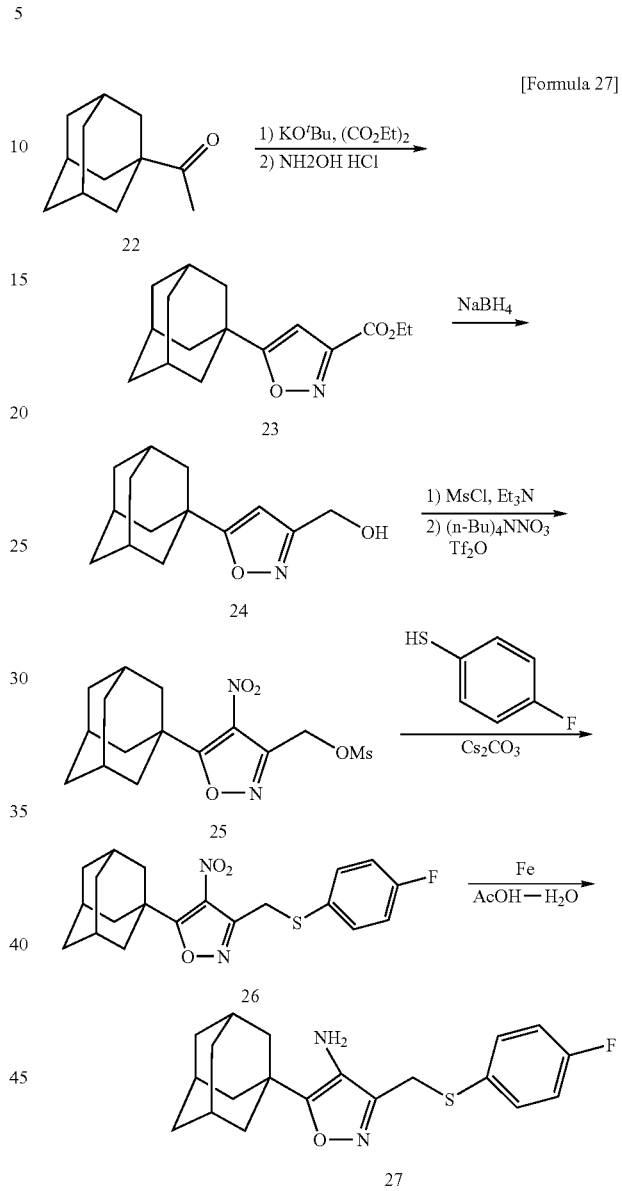

To a solution of cycloheptanecarboxyric acid (194 µL) in toluene (7 mL) were added thionylchloride (0.206 mL) and DMF (1 drop) and the resulting solution was stirred at 70° C. After removal of toluene under reduced pressure, the residue was dissolved in $CH_2Cl_2$ (3 mL). 17 (200 mg) in $CH_2Cl_2$ (2 mL) and triethylamine (0.246 mL) were added to the solution under $N_2$ atmosphere and the resulting solution was stirred at room temp. After termination of this reaction, the solution was partitioned between water and EtOAc and extracted with EtOAc. The extraction was washed with brine and dried with $MgSO_4$ and concentrated in vacuo. The residue was purified by silicagel columnchromatography to give 20 (290 mg).

To a solution of 20 (100 mg) in MeOH (2 mL) was added 2N NaOH soln. (170 µL) at 0° C. and the resulting solution was stirred at room temp. After termination of this reaction, the solution was neutralized with 2N HCl soln. and diluted with $CHCl_3$ and dried with $MgSO_4$ and concentrated in vacuo. To a solution of the residue in DMF (2 mL) were added 1-adamantanamine (77.1 mg), 1-hydroxybenzotriazole (68.9 mg) and 1-Ethyl-3-(3-dimethylaminopropyl)-carbodiimide hydrochloride (97.7 mg) were added to the solution and the mixture was stirred at room temp. After termination of this reaction, the reaction mixture was partitioned between 2N HCl soln. and EtOAc and extracted with EtOAc. The extraction was washed with 2N HCl soln., sat.$NaHCO_3$ soln., brine successively and dried with $MgSO_4$ and concentrated in vacuo. The residue was purified by silicagel columnchromatography to give 21 (A-26)(132 mg).

To a solution of potassium t-butoxide (6.92 g) in THF (90 mL) were added oxalic acid diethyl ester (9.14 mL) and 1-adamantylmethylketone (10 g) in THF (30 mL). After termination of this reaction, cooled 1N HCl soln-EtOAc was added to the mixture and partitioned between water and EtOAc and extracted with EtOAc. The extraction was washed with water, brine and dried with $MgSO_4$ and concentrated in vacuo. To a solution of the residue in EtOH (150 mL) was added hydroxylamine hydrochloride (8.58 g) under $N_2$ atmosphere and the resulting solution was stirred at room temp. The reaction mixture was refluxed, then cooled to room temp. and the volatile was removed under reduced pressure. Sat. $NaHCO_3$ soln. and EtOAc were added to the residue and the aqueous layer was extracted with EtOAc. The extraction was washed with water, brine and dried with $MgSO_4$ and concentrated in vacuo. The residue was purified by silicagel columnchromatography to give 23 (13.4 mg).

To a solution of 23 (6 g) in EtOH (60 mL)-THF (40 mL) was added sodium borohydride (907 mg) under N₂ atmosphere and the resulting solution was stirred at room temp. overnight. After addition of dilute HCl, the volatile was removed under reduced pressure. Water and EtOAc were added to the residue and the aqueous layer was extracted with EtOAc. The extraction was washed with brine and dried with MgSO₄ and concentrated in vacuo to give 24 (5.05 g).

To a solution of 24 (1 g) in toluene (20 mL) were added triethylamine (0.657 mL) and methanesulfonylchloride (0.332 mL) at 0° C. under N₂ atmosphere. After termination of this reaction, the solution was partitioned between NaHCO₃ soln. and EtOAc and extracted with EtOAc. The extraction was washed with brine dried with MgSO₄ and concentrated in vacuo. To a solution of tetra-n-butylammonium nitrate (1.96 g) in CH₂Cl₂ (2 mL) was added trifluoromethanesulfonyl anhydride (1.08 mL) at 0° C. under N₂ atmosphere and the resulting solution was stirred at room temp. The residue was dissolved in CH₂Cl₂ (2 mL) and mixed with the above solution. After termination of this reaction, the reaction mixture was partitioned between sat.NaHCO₃ soln. and EtOAc and extracted with EtOAc. The extraction was washed with brine and dried with MgSO₄ and concentrated in vacuo. The residue was purified by silicagel columnchromatography to give 25 (1.44 g).

To a solution of 25 (300 mg) in MeCN (6 mL) were added 4-fluorothiophenol (98.6 µL) and cesium carbonate (329 mg) under N₂ atmosphere and the resulting solution was stirred at room temp. After termination of this reaction, the solution was partitioned between NaHCO₃ soln. and EtOAc and extracted with EtOAc. The extraction was washed with brine and dried with MgSO₄ and concentrated in vacuo. The residue was purified by silicagel columnchromatography to give 26 (299 mg).

To a solution of 26 (150 mg) in AcOH (3 mL)-H₂O (1 mL) was added Fe powder (108 mg) under N₂ atmosphere and the resulting mixture was stirred at 50° C. After cooling to room temp., EtOAc and aqueous ammonia were added to the mixture, then partitioned between sat.NaHCO₃ soln. and EtOAc and extracted with EtOAc. The extraction was washed with brine and dried with MgSO₄ and concentrated in vacuo. The residue was purified by silicagel columnchromatography to give 27 (44 mg).

Several kinds of the derivatives can be synthesized by modifying amino group of compound 27.

Example 9

[Formula 28]

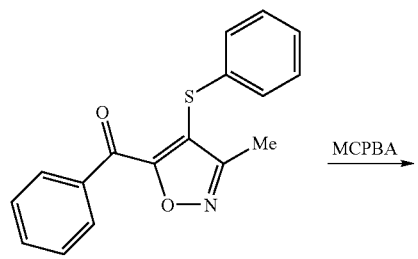

4

-continued

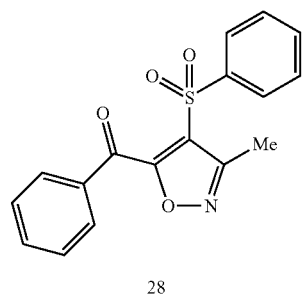

28

To a solution of 4 (100 mg) in THF (2 mL) was added m-chloroperbenzoic acid (175 mg) under N₂ atmosphere and the resulting solution was stirred at 50° C. Additional m-chloroperbenzoic acid (175 mg) was added to the reaction mixture and the whole mixture was refluxed. After cooling to room temp. the mixture was partitioned between sat.NaHCO₃ soln. and EtOAc and extracted with EtOAc. The extraction was washed with brine dried with MgSO₄ and concentrated in vacuo. The residue was purified by silicagel columnchromatography and recrystallized from EtOAc-Et₂O-hexane to give 28 (A-20)(93 mg).

Example 10

[Formula 29]

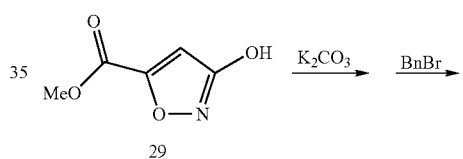

29

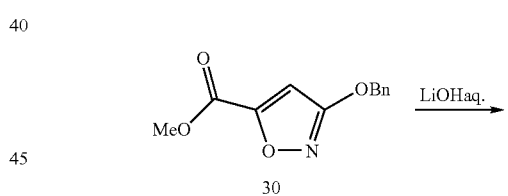

30

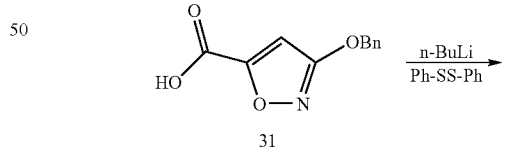

31

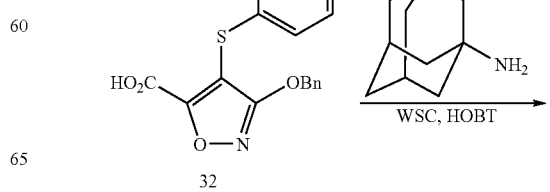

32

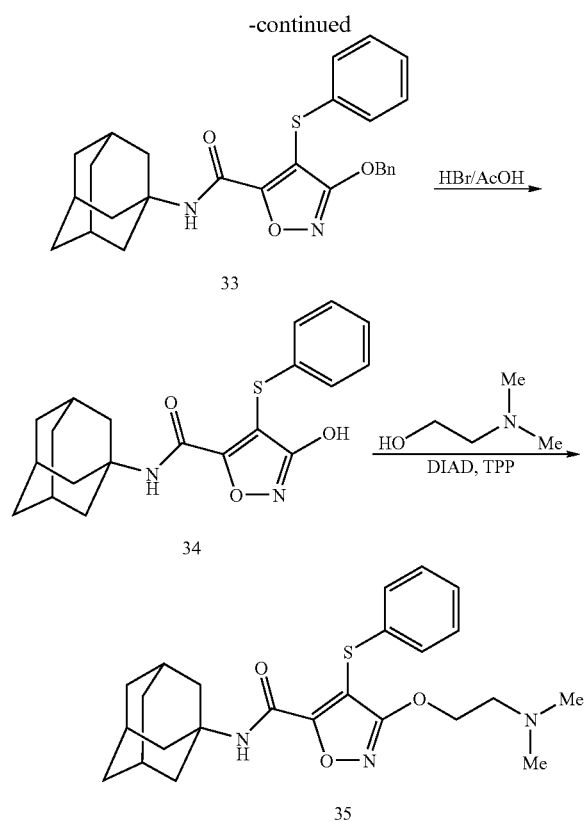

solution was stirred at room temp. for 3 days. After termination of this reaction, the reaction solution was partitioned between 2N HCl soln. and EtOAc and extracted with EtOAc. The extraction was washed with sat.NaHCO₃ soln., brine successively, then dried with MgSO₄ and concentrated in vacuo. The residue was purified by silicagel columnchromatography to give 33 (1.4 g).

25% HBr/AcOH (20 mL) was added to 33 (14 g) under N₂ atmosphere and the resulting mixture was stirred at room temp. overnight. After termination of this reaction, the volatile was removed and the residue was purified by silicagel columnchromatography to give 34 (885 mg).

To a solution of 34 (215 mg) in THF (2 mL) were added 2-dimethylaminoethanol (52 mg) in THF (2 mL), triphenylphosphine (152 mg), azodicarboxylic acid diisopropylester (109 μL) and the resulting solution was stirred at room temp. for 1 hr. Additional 2-dimethylaminoethanol (52 mg) in THF (2 mL), triphenylphosphine (152 mg), azodicarboxylic acid diisopropylester (109 μL) were added to the reaction mixture and stirred at room temp. overnight. After termination of this reaction, the volatile was removed. Sat.NaHCO₃ soln. and EtOAc were added to the residue, then extracted with EtOAc. The extraction was washed with brine and dried with Na₂SO₄ and concentrated in vacuo. The residue was purified by silicagel columnchromatography to give 35 (B-21)(103 mg).

According to below scheme, compound B-20, 34~36, 46, 48~52, 55~58, 67~70, 82~85, 87~95, 99~102, 104~115, 118~120, C-8, 75~85 and 92 were synthesized by the same method as described above.

To a solution of 29 (1.0 g) in acetone (20 mL) was added potassium carbonate (1.9 g) under N₂ atmosphere and the resulting mixture was stirred at 70° C. for 1 hr. Benzyl bromide (1.3 mL) was added to the mixture and the whole mixture was stirred at 70° C. for 2 hrs and at room temp. for 16 hrs. After termination of this reaction, the reaction mixture was filtrated by filter paper. The resulting solution was concentrated in vacuo and the residue was purified by silicagel columnchromatography to give 30 (1.3 g).

To a solution of 30 (1.3 g) in THF/MeOH (1/1)(26 mL) was added 1N LiOH soln. (12 mL) and the resulting solution was stirred at room temp. for 4 hrs. After termination of this reaction, the reaction mixture was extracted with Et₂O. The extraction was neutralized with 2N HCl soln. and extracted with EtOAc and washed with brine and dried with MgSO₄ and concentrated in vacuo. The residue was washed with n-hexane to give 31 (1.2 g).

To a solution of 31 (600 mg) in THF (15 mL) was added n-Butyllithium (3.8 mL, 1.58M hexane solution) at −78° C. under N, atmosphere, then the reaction solution was allowed warm up to room temp. and stirred for 0.5 hr. After cooling again to −78° C., diphenylsulfide (717 mg) was added to the reaction solution and allowed warm up to 0° C. and stirred for 1 hr. After termination of this reaction, dilute hydrochloric acid was added to the solution. The solution was adjusted to pH 8.0 by 1N NaOH soln. and extracted with Et₂O. The extraction was neutralized with 2N HCl soln. and extracted with EtOAc and washed with brine and dried with MgSO₄ and concentrated in vacuo. The residue was washed with n-hexane to give 32 (781 mg).

To a solution of 32 (1.7 g) in DMF (20 mL) were added 1-adamantanamine (681 mg), 1-hydroxybenzotriazole (790 mg) and 1-Ethyl-3-(3-dimethyl-aminopropyl)-carbodiimide hydrochloride (1.1 g) under N₂ atmosphere, and the resulting

[Formula 30]

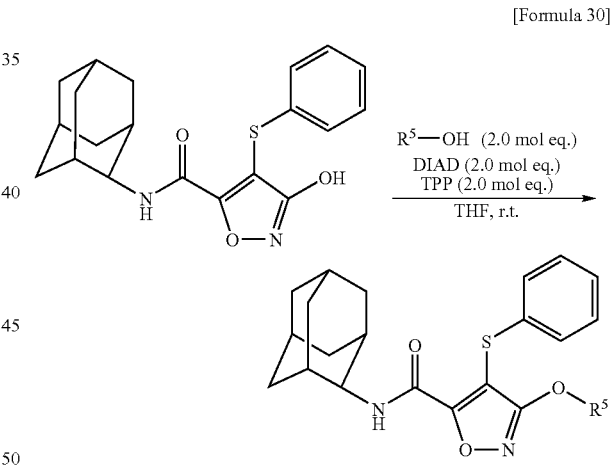

Example 11

[Formula 31]

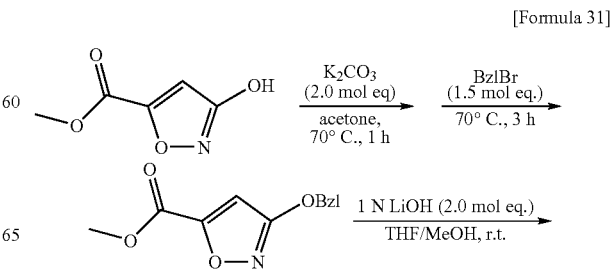

37
-continued
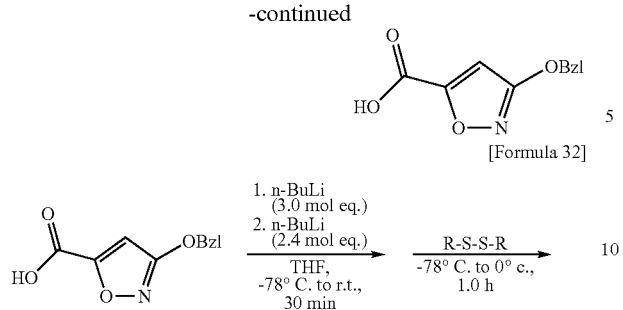
[Formula 32]
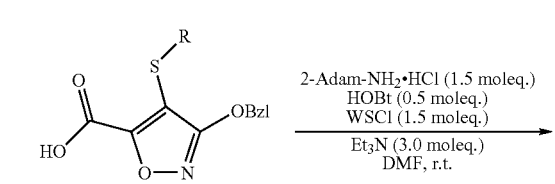
38
-continued
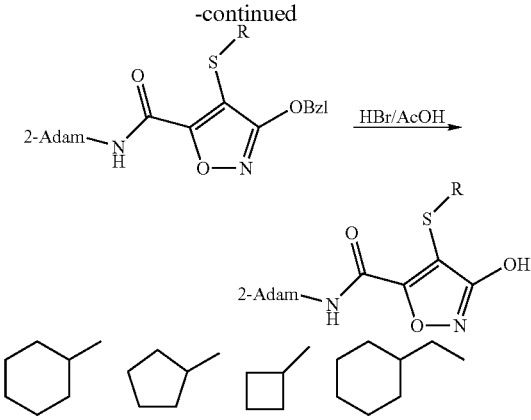
According to above, compound B-71~72, 81, 86, 103, 117, C-1~7, 9~24, 31~74, 86~91, 93~120 were synthesized.
Example 12
[Formula 33]
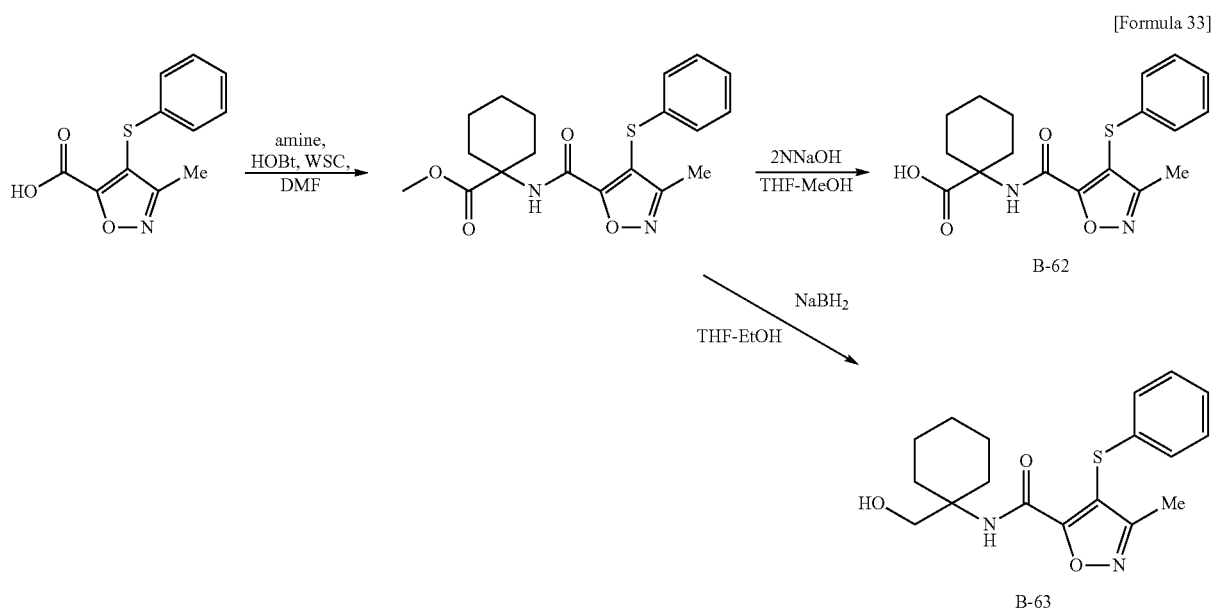
According to above scheme, compound B-62 and B-63 were synthesized.
Example 13
[Formula 34]
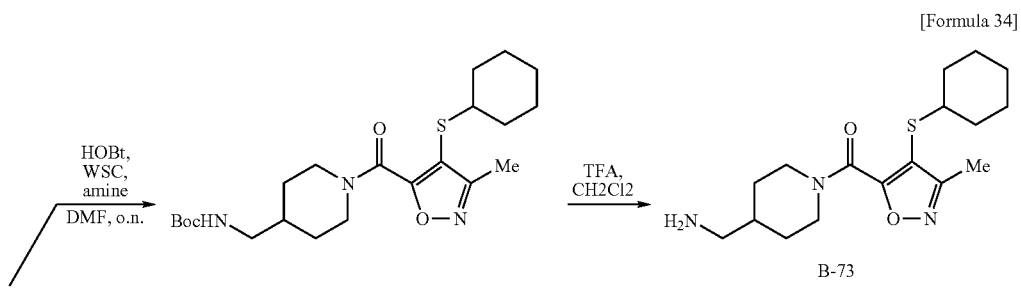

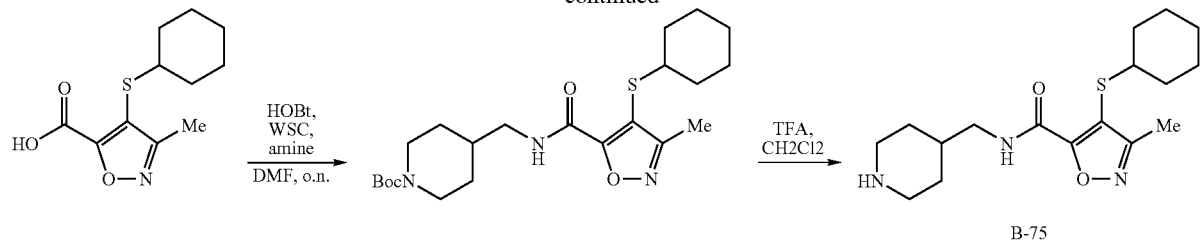
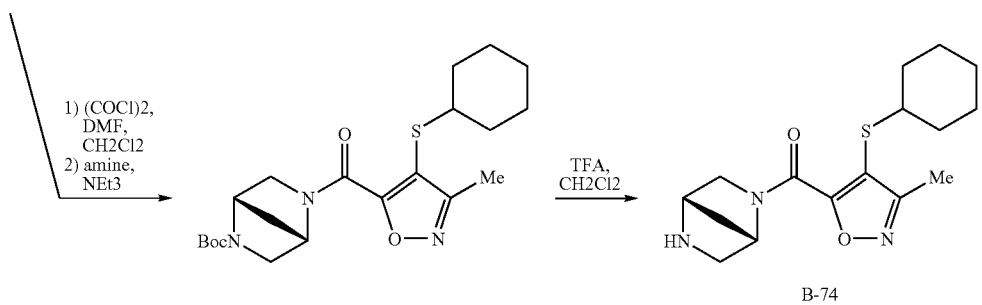
According to above scheme, compound B-73, B-74 and B-75 were synthesized.
Example 14
[Formula 35]
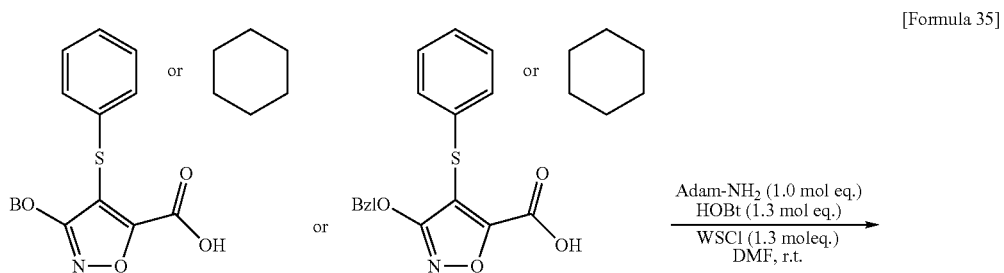
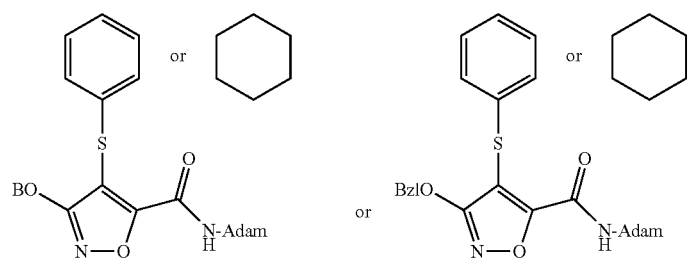

According to above scheme, compound B-1, B-2, B-3 and B-4-were synthesized.
Example 15
[Formula 36]
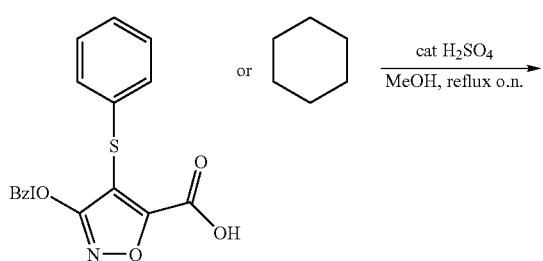
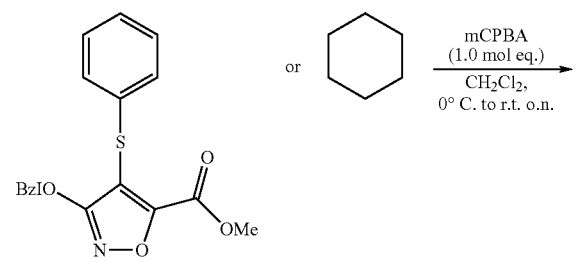
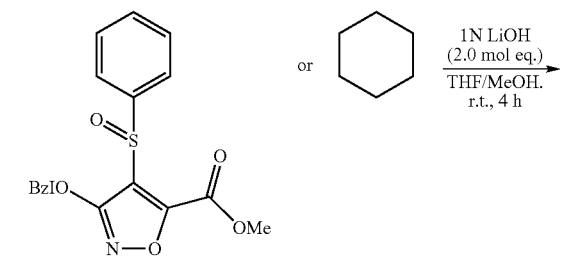
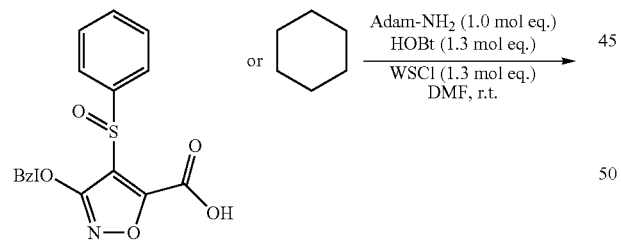
According to above scheme, compound B-9 and B-10 were synthesized.
Example 16
[Formula 37]
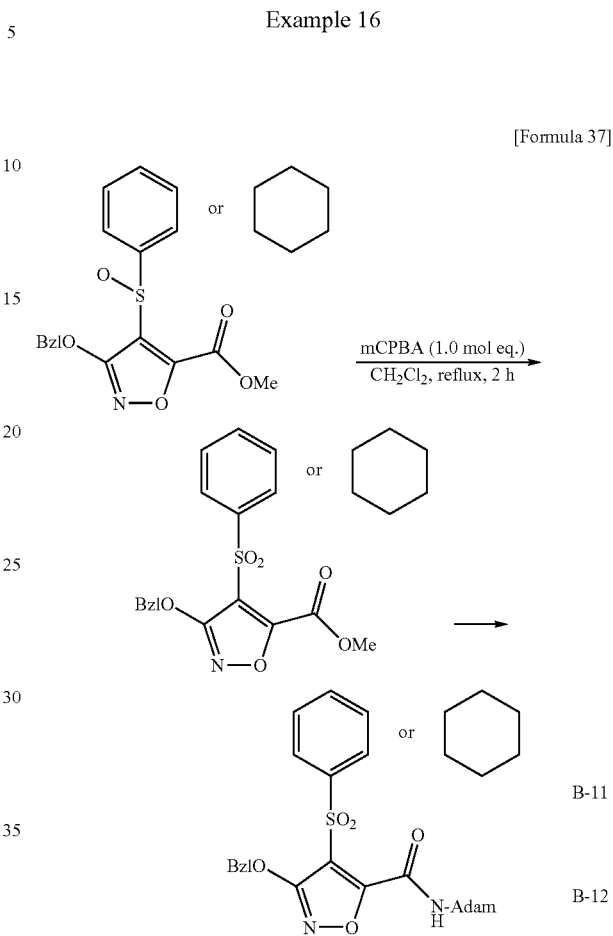
According to above scheme, compound B-11 and B-12 were synthesized.
Example 17
[Formula 38]
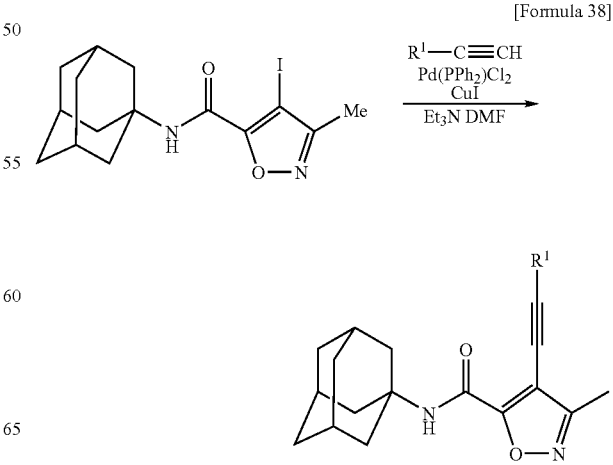

R¹ =

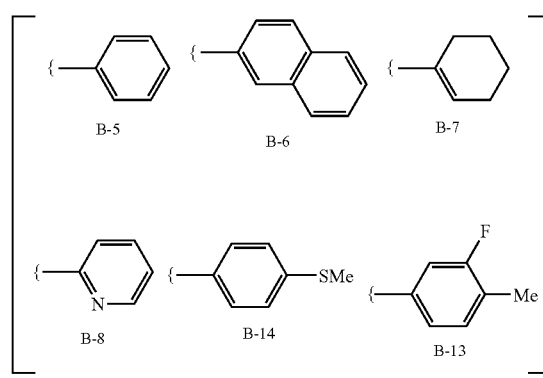

According to above scheme, compound B-5, B-6, B-7, B-8, 1'-13 and B-14 were synthesized.

Example 18

[Formula 39]

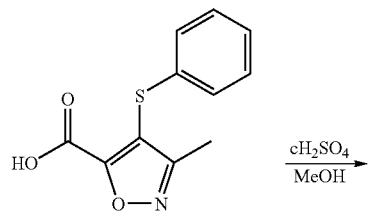

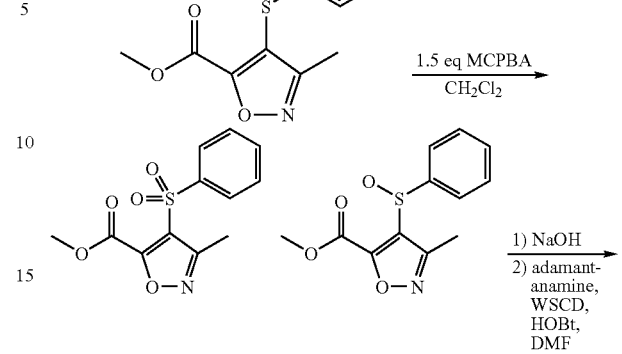

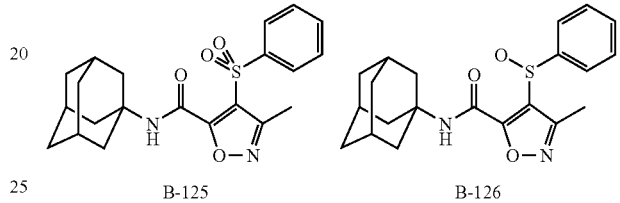

According to above scheme, compound B-125 and B-126 were synthesized.

The following compounds were synthesized as well as the above-mentioned execution example. Liquid chromatography mass spectrometry (LC-MS) was analyzed by the following condition. The device made of Waters and the column made of Phenomenex Luna 5 μC18 (2) 100 A (50 mm×4.60 mmφ) was used for the measurement. The elution was a straight line inclination of MeCN density (10%~100%/3 min) at flow velocity 3.0 mL/min.

TABLE 1

| No. | Structure | 300 MzNMR (CDCl3 or d6-DMSO) |
|---|---|---|
| A-1 | 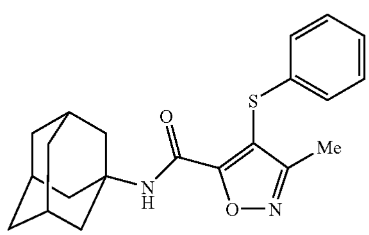 | 1.66-1.72 (6H, m), 2.03-2.15 (9H, m), 2.13 (3H, s), 6.73-6.84 (1H, br), 7.16-7.33 (5H, m). |
| A-2 | 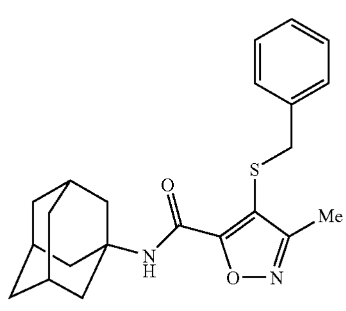 [SMILES: Cc1noc(C(=O)NC23CC4CC(CC(C4)C2)C3)c1SCc1ccccc1] | 1.69-1.74 (6H, m), 2.00 (3H, s), 2.03-2.16 (9H, m), 3.96 (2H, s), 6.77-6.85 (1H, br), 7.03-7.09 (2H, m), 7.21-7.27 (2H, m). |

TABLE 1-continued
| No. | Structure | 300 MzNMR (CDCl3 or d6-DMSO) |
|---|---|---|
| A-3 | 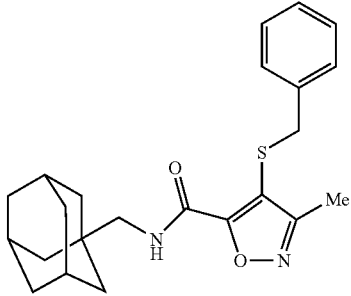 [SMILES: Cc1noc(C(=O)NCC23CC4CC(CC(C4)C2)C3)c1SCc1ccccc1] | 1.51-1.80 (12H, m), 1.97-2.05 (3H, m), 2.02 (3H, s), 3.07 (2H, d, J = 6.3 Hz), 3.97 (2H, s), 7.04-7.28 (6H, m). |
| A-4 | 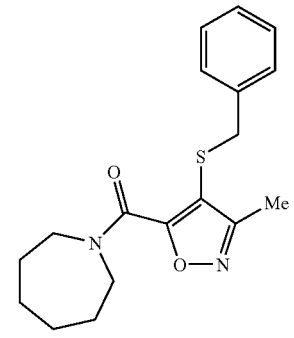 [SMILES: Cc1noc(C(=O)N2CCCCCC2)c1SCc1ccccc1] | 1.55-1.90 (8H, m), 1.78 (3H, s), 3.25 (2H, t, J = 5.9 Hz), 3.68 (2H, t, J = 5.9 Hz), 3.95 (2H, s), 7.11-7.28 (5H, m). |
| A-5 | 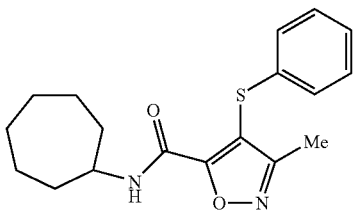 [SMILES: Cc1noc(C(=O)NC2CCCCCC2)c1Sc1ccccc1] | 1.45-1.67 (10H, m), 1.88-2.02 (2H, m), 2.16 (3H, s), 4.09-4.23 (1H, m), 7.04-7.16 (1H, br), 7.16-7.33 (5H, m). |
| A-6 | 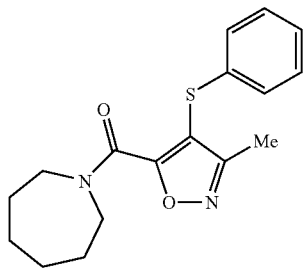 [SMILES: Cc1noc(C(=O)N2CCCCCC2)c1Sc1ccccc1] | 1.51-1.86 (8H, m), 2.17 (3H, s), 3.35 (2H, t, J = 6.0 Hz), 3.65 (2H, t, J = 6.0 Hz), 7.15-7.30 (5H, m). |
TABLE 2
| No. | Structure | 300 MzNMR (CDCl3 or d6-DMSO) |
|---|---|---|
| A-7 | 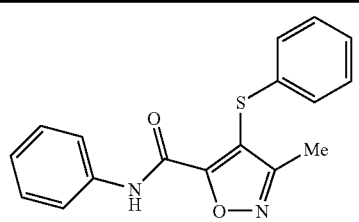 | 2.19 (3H, s), 7.14-7.41 (8H, m), 7.60-7.67 (2H, m), 8.86-8.94 (1H, br). |

TABLE 2-continued

| No. | Structure | 300 MzNMR (CDCl3 or d6-DMSO) |
|---|---|---|
| A-8 | 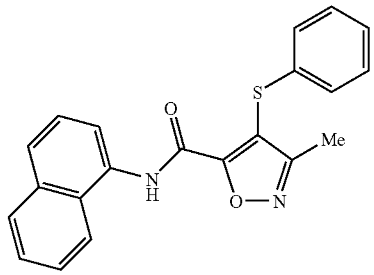 [SMILES: Cc1noc(C(=O)Nc2cccc3ccccc23)c1Sc1ccccc1] | 2.26 (3H, s), 7.24-7.38 (5H, m), 7.41-7.55 (3H, m), 7.71-7.91 (3H, m), 8.25 (1H, d, J = 7.2 Hz), 9.48-9.56 (1H, br). |
| A-9 | 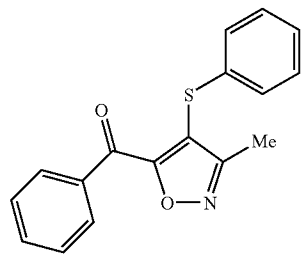 [SMILES: Cc1noc(C(=O)c2ccccc2)c1Sc1ccccc1] | 2.11 (3H, s), 7.19-7.32 (5H, m), 7.48-7.56 (2H, m), 7.665 (1H, tt, J = 7.4, 1.6 Hz), 8.05-8.10 (2H, m). |
| A-10 | 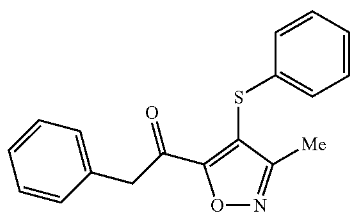 [SMILES: Cc1noc(C(=O)Cc2ccccc2)c1Sc1ccccc1] | 2.03 (3H, s), 4.29 (2H, s), 7.08-7.36 (10H, m). |
| A-11 | 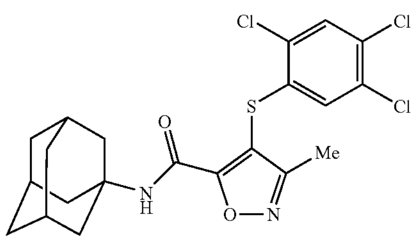 [SMILES: Cc1noc(C(=O)NC23CC4CC(CC(C4)C2)C3)c1Sc1cc(Cl)c(Cl)cc1Cl] | 1.67-1.73 (6H, m), 2.06-2.15 (9H, m), 2.20 (3H, s), 6.39-6.47 (1H, br), 6.85 (1H, s), 7.48 (1H, s). |
| A-12 | 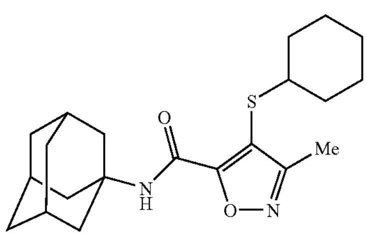 | 1.18-1.96 (16H, m), 2.12 (9H, br-s), 2.34 (3H, s), 2.91-3.03 (1H, m), 7.29-7.36 (1H, br). |

TABLE 3

| No. | Structure | 300 MzNMR (CDCl3 or d6-DMSO) |
|---|---|---|
| A-13 | 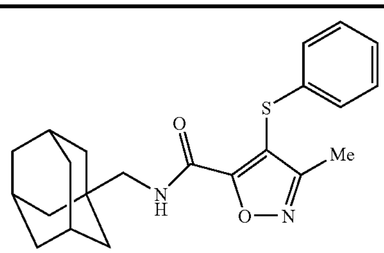 | 1.42-1.59 (9H, m), 1.61-1.72 (3H, m), 1.87-1.96 (3H, br), 2.19 (3H, s), 3.14 (2H, d, J = 6.3 Hz), 7.12-7.35 (6H, m). |

TABLE 3-continued

| No. | Structure | 300 MzNMR (CDCl3 or d6-DMSO) |
|---|---|---|
| A-14 | 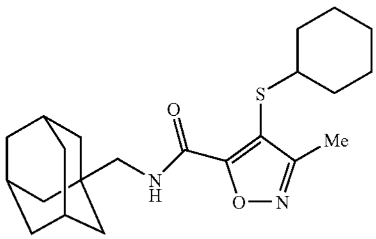 [SMILES: Cc1noc(C(=O)NCC23CC4CC(CC(C4)C2)C3)c1SC1CCCCC1] | 1.17-1.44 (5H, m), 1.54-2.06 (20H, m), 2.36 (3H, s), 2.96-3.09 (1H, m), 3.18 (2H, d, J = 6.3 Hz), 7.58-7.70 (1H, br). |
| A-15 | 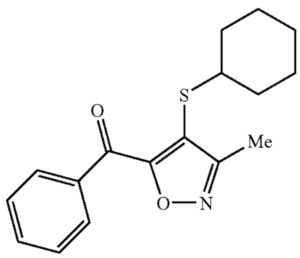 [SMILES: Cc1noc(C(=O)c2ccccc2)c1SC1CCCCC1] | 1.17-1.41 (5H, m), 1.53-1.93 (5H, m), 2.42 (3H, s), 3.15-3.27 (1H, m), 7.48-7.56 (2H, m), 7.65 (1H, tt, J = 7.4, 1.4 Hz), 8.00-8.05 (2H, m). |
| A-16 | 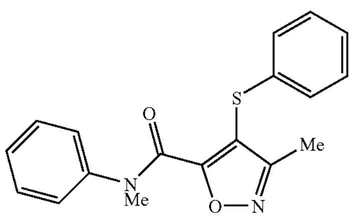 [SMILES: Cc1noc(C(=O)N(C)c2ccccc2)c1Sc1ccccc1] | 1.95 (3H, s), 3.47 (3H, s), 6.86-6.95 (2H, m), 7.08-7.28 (8H, m). |
| A-17 | 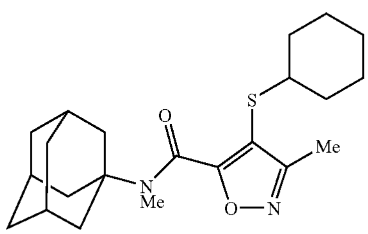 [SMILES: Cc1noc(C(=O)N(C)C23CC4CC(CC(C4)C2)C3)c1SC1CCCCC1] | 1.18-1.39 (5H, m), 1.54-1.94 (11H, m), 2.11-2.30 (9H, m), 2.31 (3H, s), 2.81 (3H, s), 2.86-2.99 (1H, m). |
| A-18 | 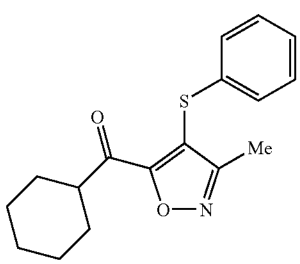 [SMILES: Cc1noc(C(=O)C2CCCCC2)c1Sc1ccccc1] | 1.12-2.00 (10H, m), 2.05 (3H, s), 3.20-3.32 (1H, m), 7.18-7.32 (5H, m). |

TABLE 4

| No. | Structure | 300 MzNMR (CDCl3 or d6-DMSO) |
|---|---|---|
| A-19 | 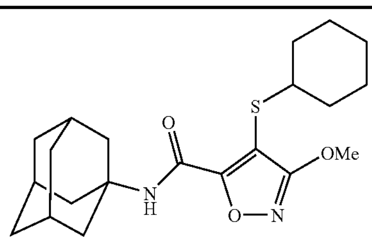 | 1.19-1.99 (16H, m), 2.11 (9H, br-s), 3.04-3.17 (1H, m), 4.06 (3H, s), 7.25-7.35 (1H, br). |

TABLE 4-continued

| No. | Structure | 300 MzNMR (CDCl3 or d6-DMSO) |
|---|---|---|
| A-20 | 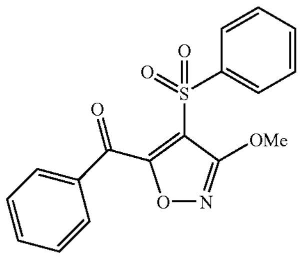 [SMILES: COc1noc(C(=O)c2ccccc2)c1S(=O)(=O)c1ccccc1] | 2.53 (3H, s), 7.51-7.75 (6H, m), 7.86-7.92 (2H, m), 8.07-8.13 (2H, m). |
| A-21 | 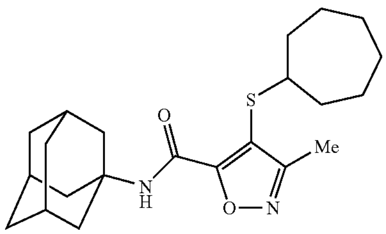 [SMILES: Cc1noc(C(=O)NC23CC4CC(CC(C4)C2)C3)c1SC1CCCCCC1] | 1.36-2.17 (27H, m), 2.33 (3H, s), 3.19 (1H, septet, J = 4.5 Hz), 7.29-7.37 (1H, br). |
| A-22 | 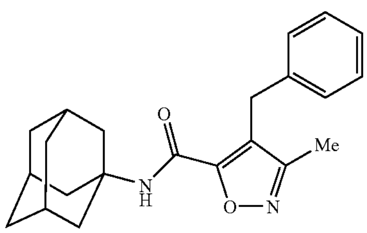 [SMILES: Cc1noc(C(=O)NC23CC4CC(CC(C4)C2)C3)c1Cc1ccccc1] | 1.66-1.79 (6H, m), 2.11 (3H, s), 2.13 (9H, br-s), 4.15 (2H, s), 6.20-6.30 (1H, br), 7.14-7.30 (5H, m). |
| A-23 | 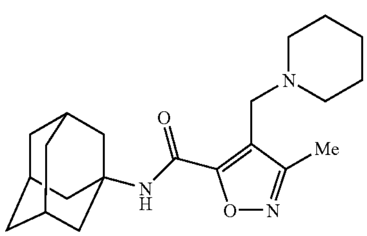 [SMILES: Cc1noc(C(=O)NC23CC4CC(CC(C4)C2)C3)c1CN1CCCCC1] | 1.42-1.62 (6H, m), 1.66-1.79 (6H, m), 2.12 (9H, br-s), 2.28 (3H, br-s), 2.32-2.46 (4H, br), 3.33 (2H, br-s), 8.56-8.67 (1H, br). |
| A-24 | 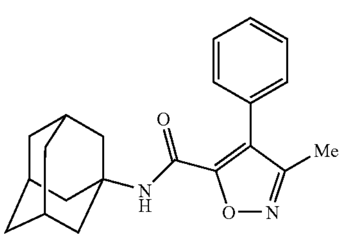 [SMILES: Cc1noc(C(=O)NC23CC4CC(CC(C4)C2)C3)c1-c1ccccc1] | 1.64-1.70 (6H, m), 2.01-2.12 (9H, m), 2.25 (3H, s), 6.06-6.17 (1H, br), 7.34-7.48 (5H, m). |

TABLE 5

| No. | Structure | 300 MzNMR (CDCl3 or d6-DMSO) |
|---|---|---|
| A-25 | 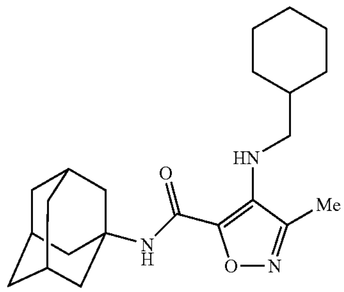 [SMILES: Cc1noc(C(=O)NC23CC4CC(CC(C4)C2)C3)c1NCC1CCCCC1] | 0.85-1.86 (18H, m), 2.06-2.16 (9H, m), 2.38 (3H, s), 2.99 (2H, d, J = 6.9 Hz), 5.81-5.91 (1H, br). |
| A-26 | 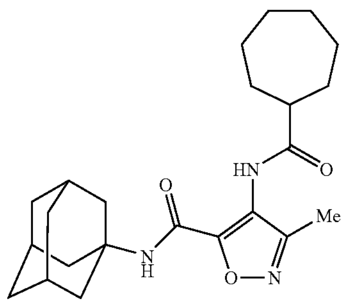 [SMILES: Cc1noc(C(=O)NC23CC4CC(CC(C4)C2)C3)c1NC(=O)C1CCCCCC1] | 1.43-2.18 (27H, m), 2.41 (3H, s), 2.41-2.53 (1H, m), 6.05-6.13 (1H, br), 8.26-8.34 (1H, br). |
| A-27 | 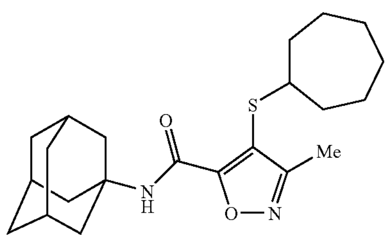 [SMILES: Cc1noc(C(=O)NC23CC4CC(CC(C4)C2)C3)c1SC1CCCCCC1] | 1.36-2.17 (27H, m), 2.33 (3H, s), 3.19 (1H, septet, J = 4.5 Hz), 7.29-7.37 (1H, br). |

TABLE 6

| No. | Structure | NMR (CDCl3 or d6-DMSO), MS or m.p. |
|---|---|---|
| B-1 | 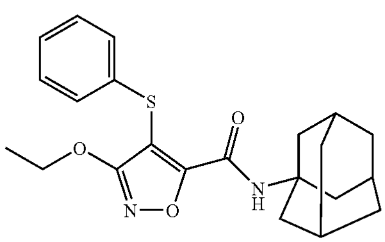 [SMILES: CCOc1noc(C(=O)NC23CC4CC(CC(C4)C2)C3)c1Sc1ccccc1] | 400 MHz (d6-DMSO) 1.22 (t, J = 6.8 Hz, 3H), 1.63 (s, 6H), 1.99 (s, 6H), 2.02 (s, 3H), 4.25 (q, J = 6.8 Hz, 2H), 7.22-7.35 (m, 5H), 8.17 (s, 1H) |
| B-2 | 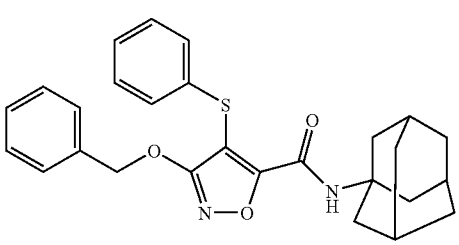 [SMILES: O=C(NC12CC3CC(CC(C3)C1)C2)c1onc(OCc2ccccc2)c1Sc1ccccc1] | 400 MHz (d6-DMSO) 1.63 (s, 6H), 1.99 (s, 6H), 2.03 (s, 3H), 5.28 (s, 2H), 7.18-7.35 (m, 10H), 8.21 (s, 1H) |

TABLE 6-continued

| No. | Structure | NMR (CDCl3 or d6-DMSO), MS or m.p. |
|---|---|---|
| B-3 | 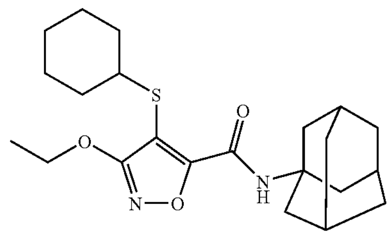 [SMILES: CCOc1noc(C(=O)NC23CC4CC(CC(C4)C2)C3)c1SC1CCCCC1] | LC-MS 405 [M + 1]+, 403 [M − 1]− |
| B-4 | 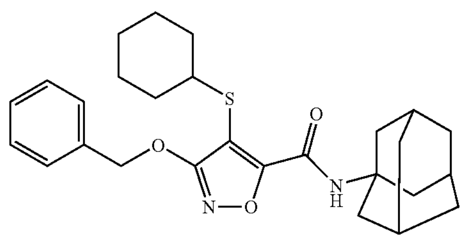 [SMILES: O=C(NC12CC3CC(CC(C3)C1)C2)c1onc(OCc2ccccc2)c1SC1CCCCC1] | FABMS 467 [M + 1]+ |
| B-5 | 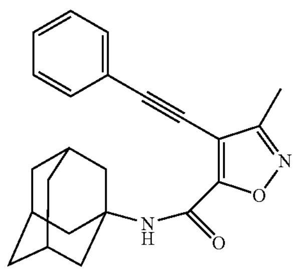 | 300 MHz (d6-DMSO) 1.65 (s, 6H), 2.05 (s, 9H), 2.37 (s, 3H), 7.45-7.48 (m, 3H), 7.55-7.58 (m, 2H), 8.04 (s, 1H) |
| B-6 | 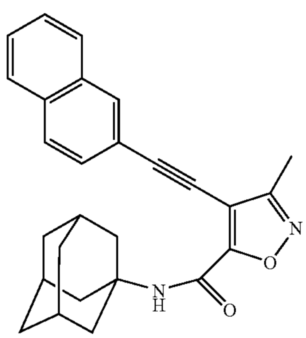 [SMILES: Cc1noc(C(=O)NC23CC4CC(CC(C4)C2)C3)c1C#Cc1ccc2ccccc2c1] | 300 MHz (d6-DMSO) 1.66 (s, 6H), 2.08 (s, 9H), 2.42 (s, 3H), 7.58-7.63 (m, 3H), 7.74-8.02 (m, 3H), 8.08 (s, 1H), 8.21 (s, 1H) |

TABLE 7

| No. | Structure | NMR (CDCl3 or d6-DMSO), MS or m.p. |
|---|---|---|
| B-7 | 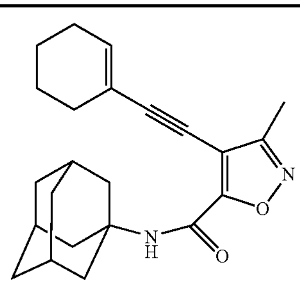 | 300 MHz (d6-DMSO) 1.50-1.64 (m, 5H), 1.65 (s, 6H), 2.03 (s, 9H), 2.10-2.20 (m, 3H), 2.27 (s, 3H), 6.26 m, 1H), 7.87 (s, 1H) |

TABLE 7-continued

| No. | Structure | NMR (CDCl3 or d6-DMSO), MS or m.p. |
|---|---|---|
| B-8 | 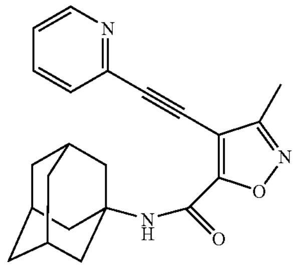 [SMILES: Cc1noc(C(=O)NC23CC4CC(CC(C4)C2)C3)c1C#Cc1ccccn1] | 300 MHz (d6-DMSO) 1.65 (s, 6H), 2.06 (s, 9H), 2.38 (s, 3H), 7.44-7.49 (m, 1H), 7.66 (d, J = 7.8 Hz, 1H), 7.89 (dt, J = 2.1, 7.8 Hz, 1H), 8.14 (s, 1H), 8.63 (d, J = 5.4 Hz, 1H) |
| B-9 | 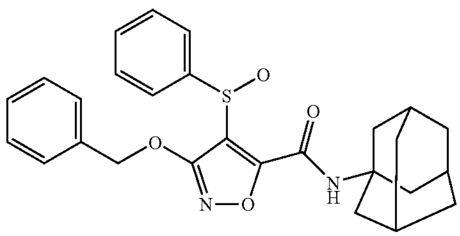 | LC-MS 477 [M + 1]+ |
| B-10 | 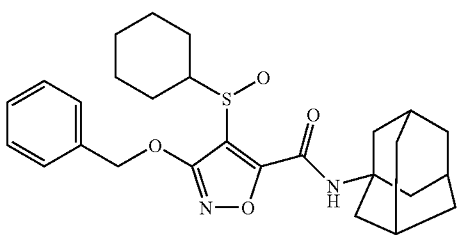 | LC-MS 483 [M + 1]+ |
| B-11 | 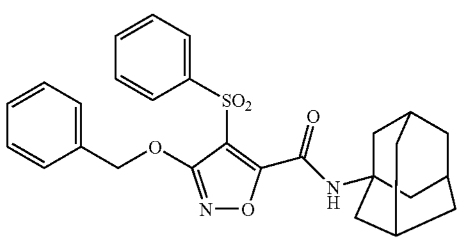 | LC-MS 493 [M + 1]+ |
| B-12 | 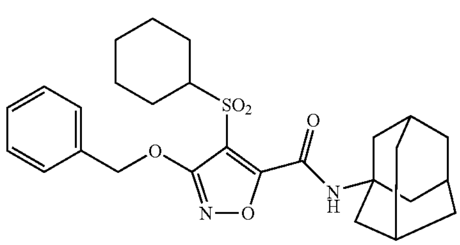 [SMILES: O=C(NC12CC3CC(CC(C3)C1)C2)c1onc(OCc2ccccc2)c1S(=O)(=O)C1CCCCC1] | LC-MS 499 [M + 1]+ |

TABLE 8

| No. | Structure | NMR (CDCl3 or d6-DMSO), MS or m.p. |
|---|---|---|
| B-13 | 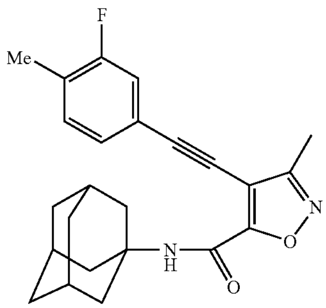 [SMILES: Cc1ccc(C#Cc2c(C)noc2C(=O)NC23CC4CC(CC(C4)C2)C3)cc1F] | 300 MHz (d6-DMSO) 1.65 (s, 6H), 2.05 (s, 9H), 2.28 (s, 3H), 2.37 (s, 3H), 7.29-7.41 (m, 5H), 8.06 (s, 1H) d6-DMSO |
| B-14 | 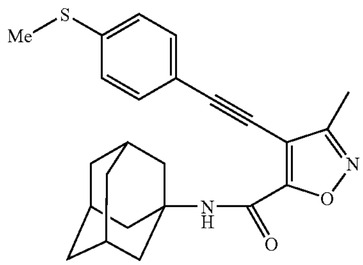 [SMILES: CSc1ccc(C#Cc2c(C)noc2C(=O)NC23CC4CC(CC(C4)C2)C3)cc1] | 300 MHz (d6-DMSO) 1.65 (s, 6H), 2.05 (s, 9H), 2.36 (s, 3H), 7.32 (d, J = 8.4 Hz, 2H), 7.48 (d, J = 8.4 Hz, 2H), 8.01 (s, 1H) |
| B-15 | trans- | 300 MHz (CDCl3) 0.81-1.79 (m, 12H), 2.18 (s, 1.5H), 2.20 (s, 1.5H), 2.32-2.40 (m, 0.5H), 2.63-2.76 (m, 1H), 3.00-3.09 (m, 0.5H), 3.31-3.37 (m, 0.5H), 3.53-3.59 (m, 0.5H), 4.50-4.56 (m, 0.5H), 4.67-4.74 (m, 0.5H), 7.18-7.29 (m, 5H) |
| B-16 | 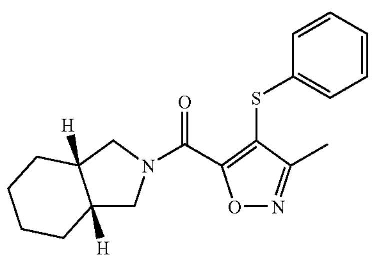 [SMILES: Cc1noc(C(=O)N2C[C@H]3CCCC[C@H]3C2)c1Sc1ccccc1] | 300 MHz (d6-DMSO) 1.20-1.60 (m, 8H), 2.12 (s, 3H), 2.22 (br, 2H), 3.20-3.31 (m, 2H), 3.42-2.47 (m, 2H), 7.21-7.37 (m, 5H) |
| B-17 | 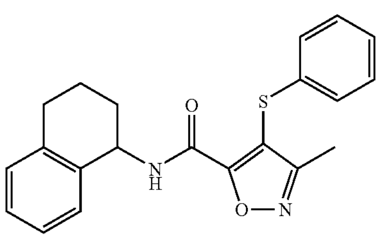 [SMILES: Cc1noc(C(=O)NC2CCCc3ccccc32)c1Sc1ccccc1] | 300 MHz (d6-DMSO) 1.67-1.99 (m, 4H), 2.09 (s, 3H), 2.70-2.78 (brm, 2H), 5.12-5.19 (m, 1H), 7.08-7.38 (m, 9H), 9.28 (d, J = 9.0 Hz, 1H) |
| B-18 | 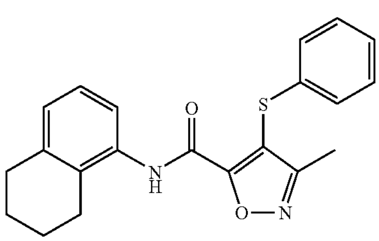 [SMILES: Cc1noc(C(=O)Nc2cccc3c2CCCC3)c1Sc1ccccc1] | LC-MS 365 [M + 1]+ |

TABLE 9

| No. | Structure | NMR (CDCl3 or d6-DMSO), MS or m.p. |
|---|---|---|
| B-19 | 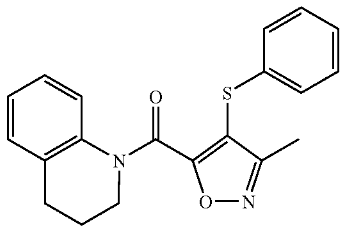 [SMILES: Cc1noc(C(=O)N2CCCc3ccccc32)c1Sc1ccccc1] | LC-MS 351 [M + 1]+ |
| B-20 | 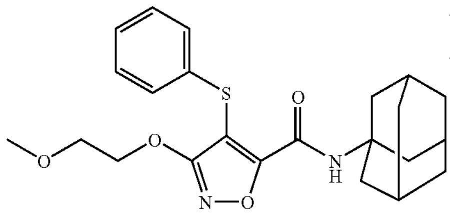 | 400 MHz (d6-DMSO) 1.63 (s, 6H), 1.99 (s, 6H), 2.03 (s, 3H), 3.18 (s, 3H), 3.55 (t, J = 4.4 Hz, 2H), 4.34 (t, J = 4.4 Hz, 2H), 7.23-7.35 (m, 5H), 8.16 (s, 1H) |
| B-21 | 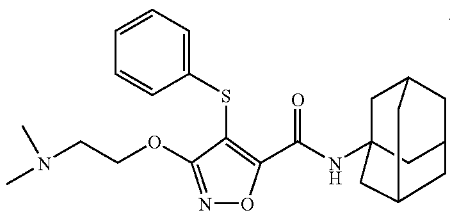 | 400 MHz (d6-DMSO) 1.63 (s, 6H), 1.99 (s, 6H), 2.03 (s, 3H), 2.08 (s, 6H), 2.53 (t, J = 5.2 Hz, 2H), 4.29 (t, J = 5.2 Hz, 2H), 7.18-7.37 (m, 5H), 8.16 (s, 1H) |
| B-22 | 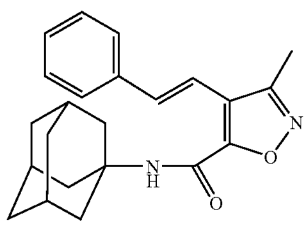 [SMILES: Cc1noc(C(=O)NC23CC4CC(CC(C4)C2)C3)c1/C=C/c1ccccc1] | 300 MHz (d6-DMSO) 1.65 (s, 6H), 2.00-2.07 (m, 9H), 2.50 (s, 3H), 7.15 (d, J = 17.1 Hz, 1H), 7.08-7.43 (m, 3H), 7.48 (d, J = 17.1 Hz, 1H), 7.54-7.57 (m, 2H), 8.05 (s, 1H) |
| B-23 | 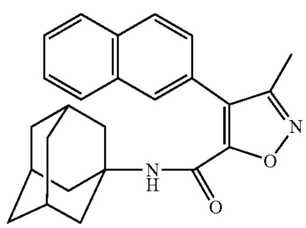 [SMILES: Cc1noc(C(=O)NC23CC4CC(CC(C4)C2)C3)c1-c1ccc2ccccc2c1] | 300 MHz (d6-DMSO) 1.60 (s, 6H), 1.98-2.02 (m, 9H), 2.32 (s, 3H), 7.32-7.60 (m, 3H), 7.94-8.00 (m, 4H), 8.09 (s, 1H) |
| B-24 | 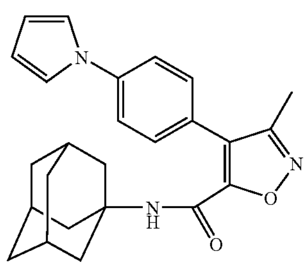 [SMILES: Cc1noc(C(=O)NC23CC4CC(CC(C4)C2)C3)c1-c1ccc(-n2cccc2)cc1] | 300 MHz (d6-DMSO) 1.62 (s, 6H), 1.99 (s, 9H), 2.29 (s, 3H), 6.29 (t, J = 2.1 Hz, 2H), 7.45 (t, J = 2.1 Hz, 2H), 7.51 (d, J = 8.4 Hz, 2H), 7.66 (d, J = 8.4 Hz, 2H), 8.07 (s, 1H) |

TABLE 10

| No. | Structure | NMR (CDCl3 or d6-DMSO), MS or m.p. |
|---|---|---|
| B-25 | 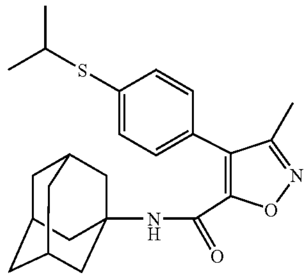 [SMILES: Cc1noc(C(=O)NC23CC4CC(CC(C4)C2)C3)c1-c1ccc(SC(C)C)cc1] | 300 MHz (d6-DMSO) 1.28 (d, J = 6.6 Hz, 6H), 1.61 (s, 6H), 1.97-2.03 (m, 9H), 2.25 (s, 3H), 3.60 (m, 1H), 7.36-7.43 (m, 4H), 7.99 (s, 1H) |
| B-26 | 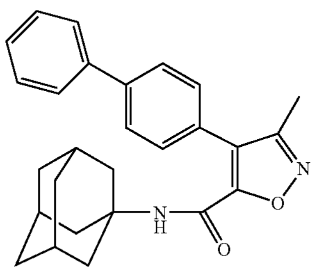 [SMILES: Cc1noc(C(=O)NC23CC4CC(CC(C4)C2)C3)c1-c1ccc(-c2ccccc2)cc1] | 300 MHz (d6-DMSO) 1.62 (s, 6H), 2.00 (s, 9H), 2.30 (s, 3H), 7.39 (m, 1H), 7.47-7.54 (m, 4H), 7.72-7.76 (m, 4H), 8.08 (s, 1H) |
| B-27 | 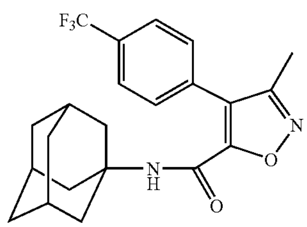 [SMILES: Cc1noc(C(=O)NC23CC4CC(CC(C4)C2)C3)c1-c1ccc(C(F)(F)F)cc1] | 300 MHz (d6-DMSO) 1.62 (s, 6H), 1.99 (s, 9H), 2.27 (s, 3H), 7.66 (d, J = 8.1 Hz, 2H), 7d6-DMSO |
| B-28 | 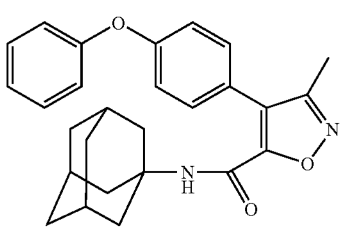 [SMILES: Cc1noc(C(=O)NC23CC4CC(CC(C4)C2)C3)c1-c1ccc(Oc2ccccc2)cc1] | 300 MHz (d6-DMSO) 1.62 (s, 6H), 1.98 (s, 9H), 2.25 (s, 3H), 7.02-7.12 8m, 4H), 7.19 (m, 1H), 7.41-7.47 (m, 4H), 7.69 (s, 1H) |
| B-29 | 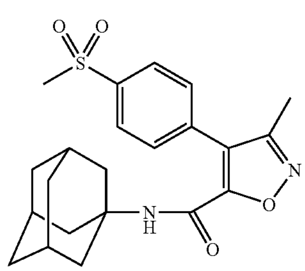 [SMILES: Cc1noc(C(=O)NC23CC4CC(CC(C4)C2)C3)c1-c1ccc(S(C)(=O)=O)cc1] | 300 MHz (d6-DMSO) 1.62 (s, 6H), 1.99 (s, 9H), 2.28 (s, 3H), 3.29 (s, 3H), 7.70 (d, J = 8.1 Hz, 2H), 7.99 (d, J = 8.1 Hz, 2H), 8.21 (s, 1H) |
| B-30 | 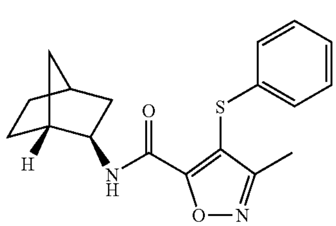 [SMILES: Cc1noc(C(=O)N[C@@H]2CC3CC[C@@H]2C3)c1Sc1ccccc1] | 300 MHz (d6-DMSO) 1.05-1.18 (m, 3H), 1.39-1.65 (m, 5H), 2.06 (s, 3H), 2.12 (d, J = 2.4 Hz, 1H), 2.20 (br, 1H), 3.65 (m, 1H), 7.16-7.34 (m, 5H), 8.69 (d, J = 6.6 Hz, 1H) |

TABLE 11

| No. | Structure | NMR (CDCl3 or d6-DMSO), MS or m.p. |
|---|---|---|
| B-31 | 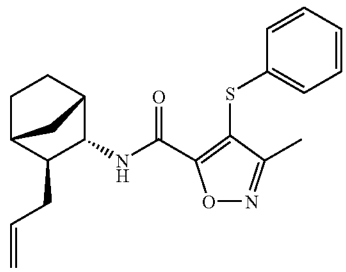 [SMILES: C=CC[C@H]1[C@@H]2CC[C@@H](C2)[C@@H]1NC(=O)c1onc(C)c1Sc1ccccc1] | 300 MHz (d6-DMSO) 1.16-1.56 (m, 7H), 1.93-2.05 (m, 3H), 2.09 (s, 3H), 2.34 (br, 1H), 3.64 (m, 1H), 4.88 (dd, J = 2.1, 7.8 Hz, 1H), 4.99 (dd, J = 2.1, 17.1 Hz, 1H), 5.61-5.75 (m, 1H), 7.18-7.36 (m, 5H), 8.30 (d, J = 7.2 Hz, 1H) |
| B-32 | 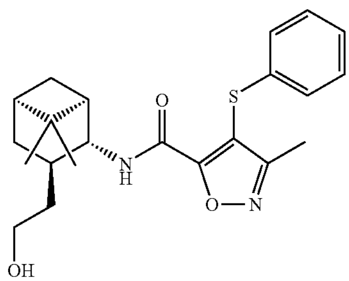 [SMILES: Cc1noc(C(=O)N[C@@H]2[C@@H](CCO)C[C@H]3C[C@@H]2C3(C)C)c1Sc1ccccc1] | 300 MHZ (d6-DMSO) 0.82 (d, J = 9.6 Hz, 1H), 1.00 (s, 3H), 1.10 (s, 3H), 1.35-1.75 (m, 3H), 1.90-2.15 (m, 5H), 2.23-2.31 (m, 1H), 3.37 (brm, 1H), 4.00 (m, 1H), 4.35 (br, 1H), 7.18-7.37 (m, 5H), 8.44 (d, J = 7.5 Hz, 1H) |
| B-33 | 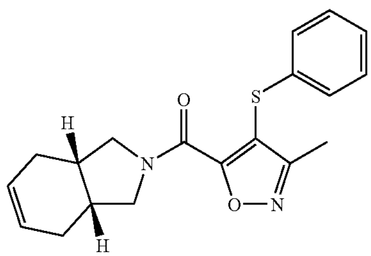 [SMILES: Cc1noc(C(=O)N2C[C@H]3CC=CC[C@H]3C2)c1Sc1ccccc1] | 300 MHZ (d6-DMSO) 1.70-1.87 (m, 2H), 2.10 (s, 3H), 2.18-2.40 (m, 4H), 3.14-3.25 (m, 2H), 3.51-3.59 (m, 2H), 5.61 (br, 2H), 7.20-7.37 (m, 5H) |
| B-34 | 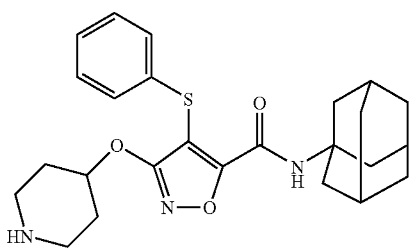 [SMILES: O=C(NC12CC3CC(CC(C3)C1)C2)c1onc(OC2CCNCC2)c1Sc1ccccc1] | 400 MHz (d6-DMSO) 1.36-1.45 (m, 2H), 1.63 (s, 6H), 1.83-1.90 (m, 2H), 1.99 (s, 6H), 2.03 (s, 3H), 2.50-2.55 (m, 2H), 2.73-2.76 (m, 2H), 4.65-4.70 (m, 1H), 7.25-7.35 (m, 5H), 8.14 (s, 1H) |
| B-35 | 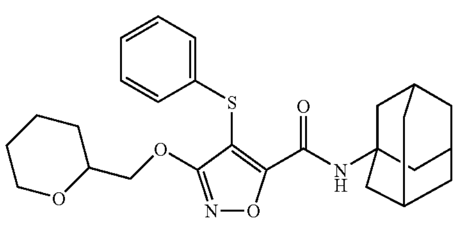 [SMILES: O=C(NC12CC3CC(CC(C3)C1)C2)c1onc(OCC2CCCCO2)c1Sc1ccccc1] | 400 MHz (d6-DMSO) 1.04-1.15 (m, 1H), 1.32-1.50 (m, 5H) 1.56-1.79 (m, 7H), 1.99 (s, 6H), 2.03 (s, 3H), 3.47-3.57 (m, 1H), 3.81-3.88 (m, 1H), 4.13-4.17 (m, 2H), 7.19-7.35 (m, 5H), 8.15 (s, 1H) |
| B-36 | 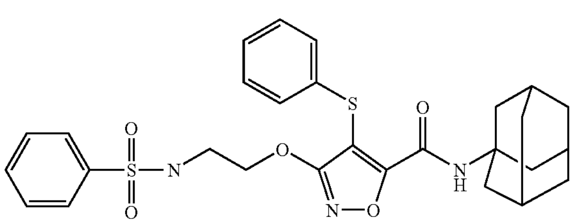 [SMILES: O=C(NC12CC3CC(CC(C3)C1)C2)c1onc(OCCNS(=O)(=O)c2ccccc2)c1Sc1ccccc1] | 400 MHz (d6-DMSO) 1.63 (s, 6H), 1.99 (s, 6H), 2.04 (s, 3H), 2.55 (s, 3H), 4.34-4.36 (m, 2H), 4.74-4.81 (m, 2H), 7.22-7.34 (m, 5H), 7.61-7.76 (m, 5H), 8.17 (s, 1H) |

TABLE 12

| No. | Structure | NMR (CDCl3 or d6-DMSO), MS or m.p. |
|---|---|---|
| B-37 | 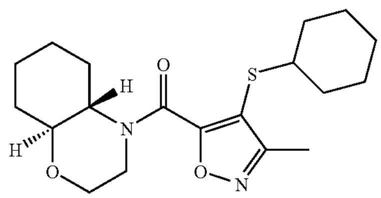 [SMILES: Cc1noc(C(=O)N2CCO[C@H]3CCCC[C@@H]32)c1SC1CCCCC1] | 300 MHz (CDCl3) 1.18-1.42 (m, 8H), 1.50-1.64 (m, 2H), 1.68-1.94 (m, 6H), 1.96-2.06 (m, 1H), 2.33 (s, 3H), 2.36-2.54 (m, 1H), 2.94-3.05 (m, 1H), 3.32-3.44 (m, 1H), 3.50-3.76 (m, 3H), 3.82-4.00 (m, 2H) |
| B-38 | trans- | 300 MHz (CDCl3) 1.24-1.38 (m, 3H), 1.49-1.76 (m, 3H), 1.94-2.00 (m, 1H), 2.17 (s, 3H), 2.44 (br, 1H), 3.35-3.93 (m, 6H), 7.19-7.30 (m, 5H) |
| B-39 | 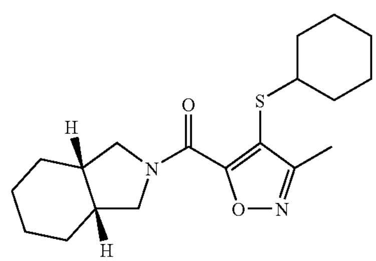 [SMILES: Cc1noc(C(=O)N2C[C@H]3CCCC[C@H]3C2)c1SC1CCCCC1] | 400 MHz (d6-DMSO) 1.17-1.79 (m, 18H), 2.26 (br, 2H), 2.28 (s, 3H), 3.03 (br, 1H), 3.21-3.50 (m, 4H) |
| B-40 | 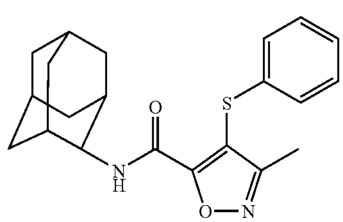 [SMILES: Cc1noc(C(=O)NC2C3CC4CC(C3)CC2C4)c1Sc1ccccc1] | 400 MHz (d6-DMSO) 1.49 (d, J = 12.4 Hz, 2H), 1.68-1.93 (m, 12H), 2.12 (s, 3H), 4.01 (brd, J = 6.0 Hz, 1H), 7.18-7.36 (m, 5H), 8.51 (d, J = 6.8 Hz, 1H) |
| B-41 | 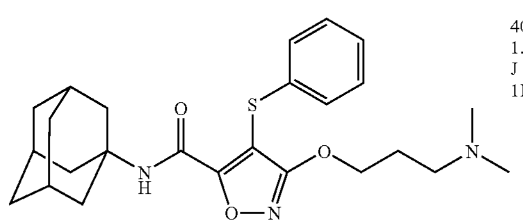 | 400 MHz (d6-DMSO) 1.63 (s, 6H), 1.67-1.74 (m, 2H), 1.95-2.13 (m, 17H), 4.21 (t, J = 6.0 Hz, 2H), 7.22-7.35 (m, 5H), 8.15 (s, 1H) |
| B-42 | trans- | 400 MHz (d6-DMSO) 0.95-1.70 (m, 12H), 1.99 (br, 1H), 2.15 (s, 3H), 3.10-3.38 (m, 3H), 7.21-7.36 (m, 5H) |

TABLE 13

| No. | Structure | NMR (CDCl3 or d6-DMSO), MS or m.p. |
|---|---|---|
| B-43 | 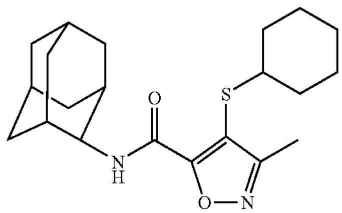 [SMILES: Cc1noc(C(=O)NC2C3CC4CC(C3)CC2C4)c1SC1CCCCC1] | 400 MHz (d6-DMSO) 1.10-2.01 (m, 24H), 2.30 (s, 3H), 3.04 (br, 1H), 4.00-4.08 (m, 1H), 8.50 (d, J = 7.2 Hz, 1H) |
| B-44 | 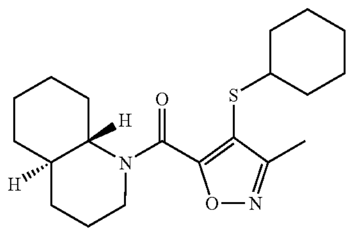 [SMILES: Cc1noc(C(=O)N2CCC[C@H]3CCCC[C@@H]32)c1SC1CCCCC1] | 400 MHz (d6-DMSO) 0.97-1.80 (m, 12H), 2.06 (br, 1H), 2.27 (s, 3H), 2.95 (br, 1H), 3.15 (br, 1H), 3.32-3.26 (m, 2H) |
| B-45 | 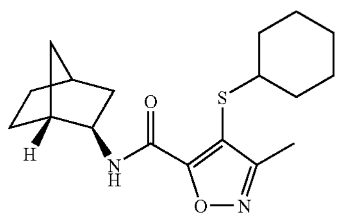 [SMILES: Cc1noc(C(=O)N[C@@H]2CC3CC[C@@H]2C3)c1SC1CCCCC1] | 400 MHz (d6-DMSO) 1.09-1.78 (m, 18H), 2.19 (br, 1H), 2.24 (br, 1H), 2.28 (s, 3H), 3.09 (br, 1H), 3.69 (br, 1H), 8.54 (d, J = 6.4 Hz, 1H) |
| B-46 | 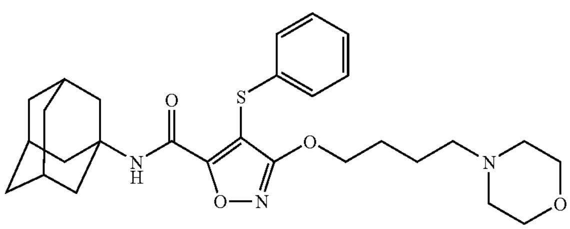 [SMILES: O=C(NC12CC3CC(CC(C3)C1)C2)c1onc(OCCCCN2CCOCC2)c1Sc1ccccc1] | 400 MHz (d6-DMSO) 1.24-1.33 (m, 2H), 1.55-1.63 (m, 8H), 1.99-2.01 (m, 9H), 2.22 (br, 4H), 3.52 (t, J = 4.4 Hz, 4H), 4.21 (t, J = 6.0 Hz, 2H), 7.21-7.34 (m, 5H), 8.15 (s, 1H) |
| B-47 | 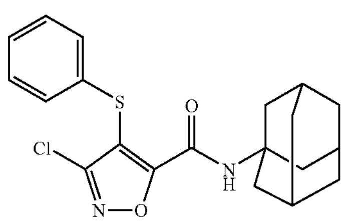 [SMILES: O=C(NC12CC3CC(CC(C3)C1)C2)c1onc(Cl)c1Sc1ccccc1] | 400 MHz (d6-DMSO) 1.63 (s, 6H), 1.99 (s, 6H), 2.04 (s, 3H), 7.26-7.38 (m, 5H), 8.40 (s, 1H) |
| B-48 | 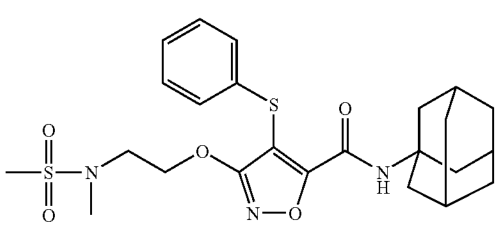 [SMILES: CN(CCOc1noc(C(=O)NC23CC4CC(CC(C4)C2)C3)c1Sc1ccccc1)S(C)(=O)=O] | 400 MHz (d6-DMSO) 1.63 (s, 6H), 1.99 (s, 6H), 2.04 (s, 3H), 2.65 (s, 3H), 2.83 (s, 3H), 3.40-3.43 (m, 2H), 4.36-4.39 (m, 2H), 7.24-7.35 (m, 5H), 8.19 (s, 1H) |

TABLE 14

| No. | Structure | NMR (CDCl3 or d6-DMSO), MS or m.p. |
|---|---|---|
| B-49 | 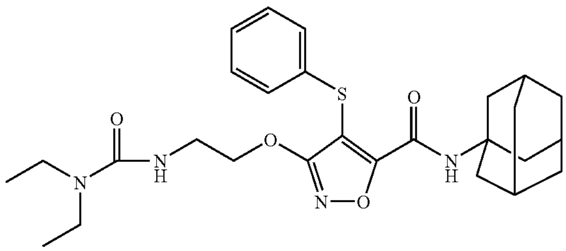 [SMILES: CCN(CC)C(=O)NCCOc1noc(C(=O)NC23CC4CC(CC(C4)C2)C3)c1Sc1ccccc1] | 400 MHz (d6-DMSO) 0.96 (t, J = 6.8 Hz, 6H), 1.63 (s, 6H), 1.98 (s, 6H), 2.03 (s, 3H), 3.13 (q, J = 6.8 Hz, 4H), 3.28-3.31 (m, 2H), 4.21-4.24 (m, 2H), 6.24 (t, J = 5.2 Hz, 1H), 7.23-7.34 (m, 5H), 8.14 (s, 1H) |
| B-50 | 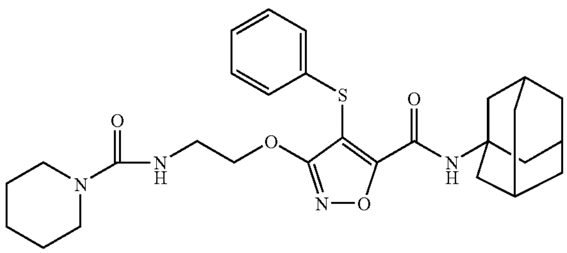 [SMILES: O=C(NC12CC3CC(CC(C3)C1)C2)c1onc(OCCNC(=O)N2CCCCC2)c1Sc1ccccc1] | 400 MHz (d6-DMSO) 1.37-1.38 (m, 4H), 1.47-1.52 (m, 2H), 1.63 (s, 6H), 1.98 (s, 6H), 2.03 (s, 3H), 3.2 (t, J = 5.6 Hz, 4H), 3.28-3.32 (m, 2H), 42.1-4.24 (m, 2H), 6.47 (t, J = 5.2 Hz, 1H), 7.24-7.34 (m, 5H), 8.14 (s, 1H) |
| B-51 | 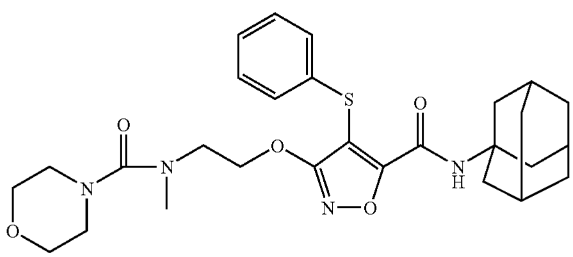 [SMILES: CN(CCOc1noc(C(=O)NC23CC4CC(CC(C4)C2)C3)c1Sc1ccccc1)C(=O)N1CCOCC1] | 400 MHz (d6-DMSO) 1.63 (s, 6H), 1.99 (s, 6H), 2.03 (s, 3H), 2.66 (s, 3H), 2.95 (t, J = 4.4 Hz, 4H), 3.43 (t, J = 5.2 Hz, 2H), 3.49 (t, J = 4.4 Hz, 4H), 4.36 (t, J = 5.2 Hz, 2H), 7.20-7.34 (m, 5H), 8.17 (s, 1H) |
| B-52 | 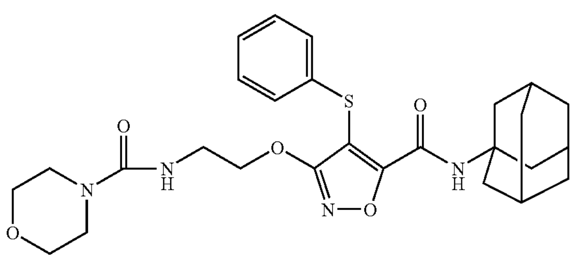 [SMILES: O=C(NC12CC3CC(CC(C3)C1)C2)c1onc(OCCNC(=O)N2CCOCC2)c1Sc1ccccc1] | 400 MHz (d6-DMSO) 1.63 (s, 6H), 1.98 (s, 6H), 2.03 (s, 3H), 3.19 (t, J = 4.8 Hz, 4H), 3.29-3.35 (m, 2H), 3.50 (t, J = 4.8 Hz, 2H), 4.26 (t, J = 6.0 Hz, 2H), 6.62 (t, J = 5.2 Hz, 1H), 7.23-7.34 (m, 5H), 8.14 (s, 1H) |
| B-53 | 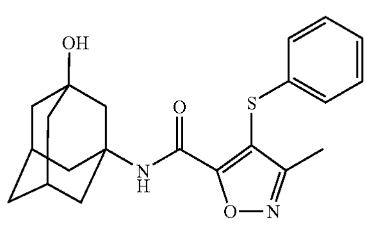 [SMILES: Cc1noc(C(=O)NC23CC4CC(CC(O)(C4)C2)C3)c1Sc1ccccc1] | 300 MHz (CDCl3) 1.56 (br.s, 2H), 1.70 (br. s, 4H), 1.98 (br.s, 4H), 2.04 (br.s, 2H), 2.14 (s, 3H), 2.30 (m, 2H), 6.90 (br.s, 1H), 7.14-7.32 (m, 5H) |
| B-54 | 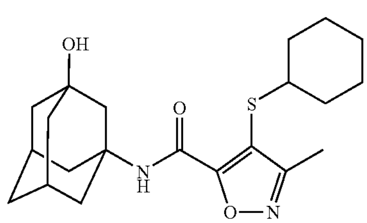 [SMILES: Cc1noc(C(=O)NC23CC4CC(CC(O)(C4)C2)C3)c1SC1CCCCC1] | LC-MS 391 [M + 1]+ |

TABLE 15

| No. | Structure | NMR (CDCl3 or d6-DMSO), MS or m.p. |
|---|---|---|
| B-55 | 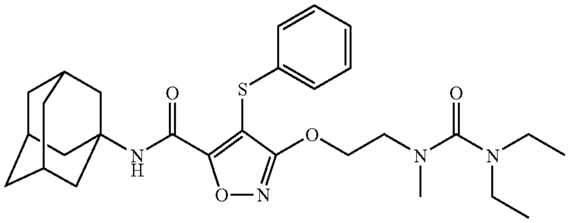 [SMILES: CCN(CC)C(=O)N(C)CCOc1noc(C(=O)NC23CC4CC(CC(C4)C2)C3)c1Sc1ccccc1] | 400 MHz (d6-DMSO) 0.95 (t, J = 6.8 Hz, 6H), 1.63 (s, 6H), 1.99 (s, 6H), 2.03 (s, 3H), 2.61 (s, 3H), 2.96 (q, J = 6.8 Hz, 4H), 3.38 (t, J = 5.2 Hz, 2H) 4.33 (t, J = 5.2 Hz, 2H), 7.20-7.34 (m, 5H), 8.18 (s, 1H) |
| B-56 | 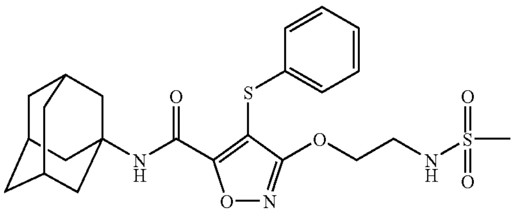 [SMILES: CS(=O)(=O)NCCOc1noc(C(=O)NC23CC4CC(CC(C4)C2)C3)c1Sc1ccccc1] | 400 MHz (d6-DMSO) 1.63 (s, 6H), 1.98 (s, 6H), 2.03 (s, 3H), 2.85 (s, 3H), 3.27-3.32 (m, 2H), 4.28 (t, J = 5.2 Hz, 2H), 7.20-7.35 (m, 6H), 8.17 (s, 1H) |
| B-57 | 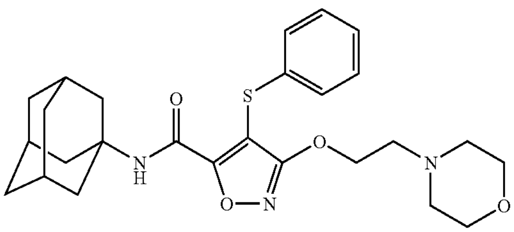 [SMILES: O=C(NC12CC3CC(CC(C3)C1)C2)c1onc(OCCN2CCOCC2)c1Sc1ccccc1] | 400 MHz (d6-DMSO) 1.63 (s, 6H), 2.00 (s, 6H), 2.03 (s, 3H), 2.26 (t, J = 4.4 Hz, 4H), 2.57 (t, J = 5.2 Hz, 2H), 3.43 (t, J = 4.4 Hz, 4H), 4.31 (t, J = 5.2 Hz, 2H), 7.22-7.34 (m, 5H), 8.16 (s, 1H) |
| B-58 | 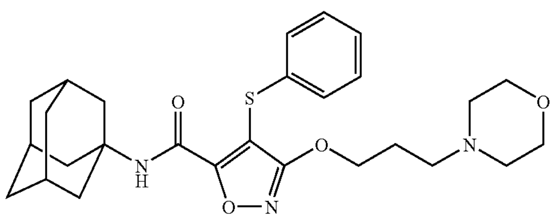 [SMILES: O=C(NC12CC3CC(CC(C3)C1)C2)c1onc(OCCCN2CCOCC2)c1Sc1ccccc1] | 400 MHz (d6-DMSO) 1.63 (s, 6H), 1.74 (quint, J = 6.4 Hz, 2H), 2.01 (s, 6H), 2.03 (s, 3H), 2.12 (t, J = 6.4 Hz, 2H), 2.17-2.24 (m, 4H), 3.52 (t, J = 4.4 Hz, 4H), 4.23 (t, J = 6.4 Hz, 2H), 7.23-7.35 (m, 5H), 8.14 (s, 1H) |
| B-59 | 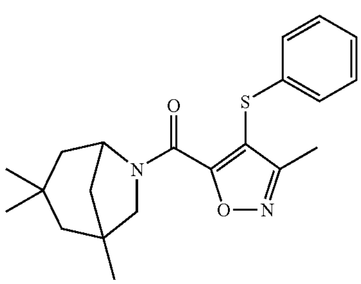 [SMILES: Cc1noc(C(=O)N2CC3(C)CC2CC(C)(C)C3)c1Sc1ccccc1] | LC-MS 371 [M + 1]+ |
| B-60 | 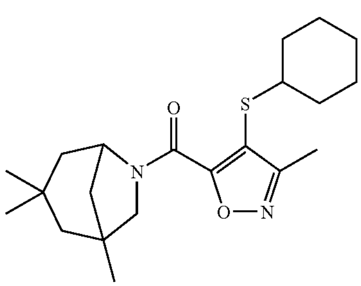 [SMILES: Cc1noc(C(=O)N2CC3(C)CC2CC(C)(C)C3)c1SC1CCCCC1] | LC-MS 377 [M + 1]+ |

TABLE 16
| No. | Structure | NMR (CDCl3 or d6-DMSO), MS or m.p. |
|---|---|---|
| B-61 | 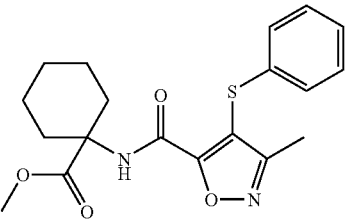 [SMILES: COC(=O)C1(NC(=O)c2onc(C)c2Sc2ccccc2)CCCCC1] | 300 MHz (CDCl₃) 1.26-2.11 (m, 10H), 2.19 (3H, s), 3.71 (3H, s), 7.19-7.34 (m, 5H), 7.52 (s, 1H) |
| B-62 | 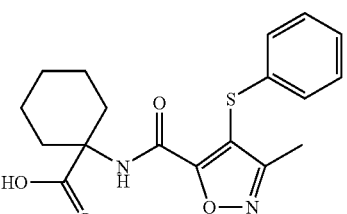 | 300 MHz (DMSO) 1.22-2.06 (m, 10H) 2.10 (3H, s), 7.19-7.37 (m, 5H), 8.77 (s, 1H), 12.5 (s, 1H) |
| B-63 | 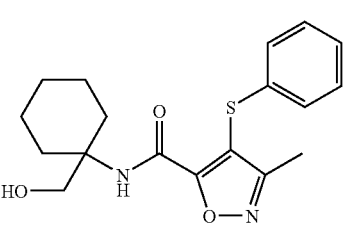 [SMILES: Cc1noc(C(=O)NC2(CO)CCCCC2)c1Sc1ccccc1] | 300 MHz (CDCl₃) 1.26-1.99 (m, 10H), 2.18 (3H, s), 3.76 (2H, s), 7.16-7.34 (m, 5H) |
| B-64 | 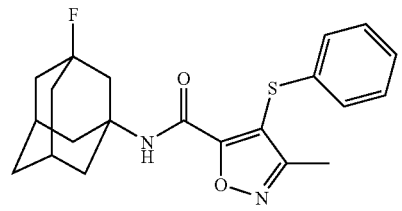 [SMILES: Cc1noc(C(=O)NC23CC4CC(CC(F)(C4)C2)C3)c1Sc1ccccc1] | 300 MHz (CDCl3) 1.56 (brs, 2H), 1.85-1.91 (m, 4H), 1.98-2.03 (m, 4H), 2.14 (m, 3H), 2.20-2.25 (m, 2H), 2.34-2.40 (m, 2H), 6.91 (brs, 1H), 7.17-7.34 (m, 5H) |
| B-65 | 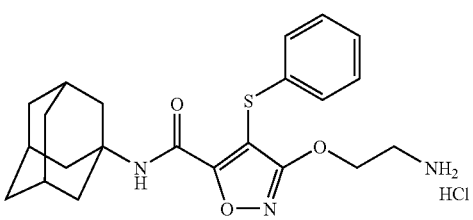 [SMILES: NCCOc1noc(C(=O)NC23CC4CC(CC(C4)C2)C3)c1Sc1ccccc1 ; Cl] | 400 MHz (d6-DMSO) 1.62 (s, 6H), 1.96 (s, 6H), 2.02 (s, 3H), 3.14 (s, 2H), 4.44-4.47 (m, 2H), 7.23-7.36 (m, 5H), 8.16 (s, 1H), 8.21 (s, 2H) |
| B-66 | 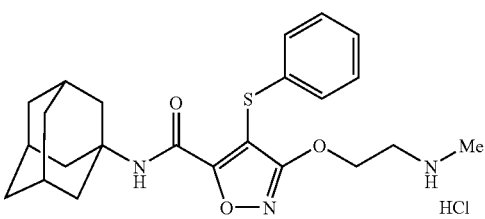 [SMILES: CNCCOc1noc(C(=O)NC23CC4CC(CC(C4)C2)C3)c1Sc1ccccc1 ; Cl] | 400 MHz (d6-DMSO) 1.62 (s, 6H), 1.97 (s, 6H), 2.03 (s, 3H), 2.42-2.50 (m, 3H), 3.22-3.27 (m, 2H), 4.52-4.55 (m, 2H), 7.23-7d6-DMSO/400 MHz |

TABLE 17
| No. | Structure | NMR (CDCl3 or d6-DMSO), MS or m.p. |
|---|---|---|
| B-67 | 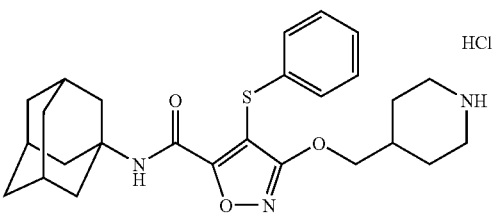 [SMILES: O=C(NC12CC3CC(CC(C3)C1)C2)c1onc(OCC2CCNCC2)c1Sc1ccccc1 ; Cl] | 400 MHz (d6-DMSO) 1.28-2.03 (m, 20H), 2.70-2.84 (m, 2H), 3.16-3.25 (m, 2H), 4.08 (d, J = 6.6 Hz, 2H), 7.23-7.36 (m, 5H), 8.17 (s, 1H), 8.80 (brs, 1H) |
| B-68 | 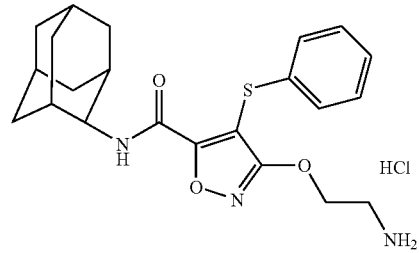 [SMILES: NCCOc1noc(C(=O)NC2C3CC4CC(C3)CC2C4)c1Sc1ccccc1 ; Cl] | DMSO-d6 δ 1.38-2.07 (m, 14H), 3.17 (s, 2H), 3.96-4.06 (m, 1H), 4.42-4.53 (m, 2H), 7.16-7.40 (m, 5H), 8.16-8.55 (m, 3H). |
| B-69 | 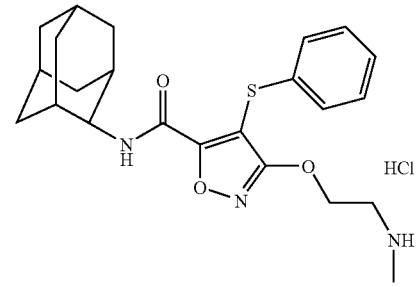 [SMILES: CNCCOc1noc(C(=O)NC2C3CC4CC(C3)CC2C4)c1Sc1ccccc1 ; Cl] | DMSO-d6 δ 1.38-1.95 (m, 12H), 2.44 (s, 2H), 2.60 (s, 2H), 3.27 (s, 3H), 3.94-4.02 (m, 1H), 4.53-4.58 (m, 2H) 7.16-7.39 (m, 5H), 8.51 (d, J = 7.2 Hz, 1H), 9.02 (brs, 1H). |
| B-70 | 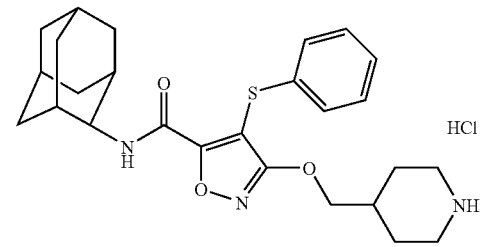 [SMILES: O=C(NC1C2CC3CC(C2)CC1C3)c1onc(OCC2CCNCC2)c1Sc1ccccc1 ; Cl] | DMSO-d6 δ 1.25-2.05 (m, 14H), 2.70-2.84 (m, 2H), 3.10-3.23 (m, 2H), 3.57 (s, 4H), 3.97-4.03 (m, 1H), 4.11 (d, J = 6.4 Hz, 2H), 7.23-7.38 (m, 5H), 8.50 (d, J = 6.8 Hz, 1H), 8.70 (brs, 1H), 9.05 (brs, 1H). |
| B-71 | 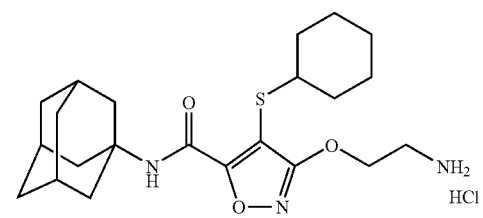 [SMILES: NCCOc1noc(C(=O)NC23CC4CC(CC(C4)C2)C3)c1SC1CCCCC1 ; Cl] | 300 MHz (d6-DMSO) 1.15-1.20 (m, 4H), 1.55 (m, 1H), 1.65 (s, 7H), 1.80-1.90 (m, 2H), 2.02 (s, 9H), 3.20-3.30 (m, 3H), 4.48-4.56 (m, 2H), 8.05 (s, 1H), 8.40 (s, 2H) |
| B-72 | 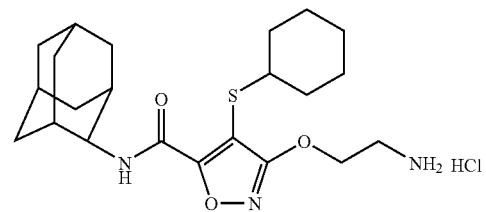 [SMILES: NCCOc1noc(C(=O)NC2C3CC4CC(C3)CC2C4)c1SC1CCCCC1 ; Cl] | 400 MHz (DMSO) 1.17-1.99 (m, 24H), 3.27 (br, 3H), 4.05 (d, J = 6.4 Hz, 1H), 4.52 (t, J = 5.2 Hz, 2H), 8.41 (br, 3H), 8.46 (d, J = 7.6 Hz, 1H) |

TABLE 18

| No. | Structure | NMR (CDCl3 or d6-DMSO), MS or m.p. |
|---|---|---|
| B-73 | 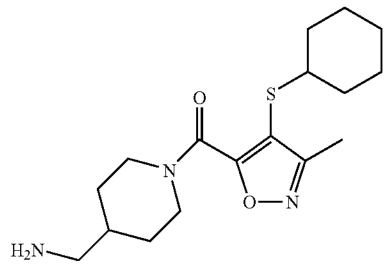 [SMILES: Cc1noc(C(=O)N2CCC(CN)CC2)c1SC1CCCCC1] | 300 MHz (CDCl3) 1.22-1.97 (m, 16H) 2.34 (s, 3H) 2.77-3.13 (m, 4H) 3.58 (d, J = 12.9 Hz, 1H) 4.72 (d, J = 12.9 Hz, 1H) |
| B-74 | 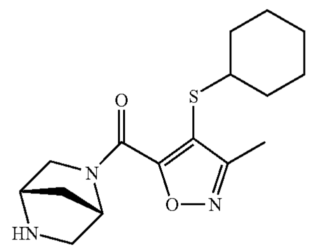 [SMILES: Cc1noc(C(=O)N2C[C@@H]3C[C@H]2CN3)c1SC1CCCCC1] | 300 MHz (CDCl3) 0.88-2.27 (m, 11H) 2.33 (s, 3H) 3.14-3.29 (m, 3H) 3.53-3.82 (m, 3H) |
| B-75 | 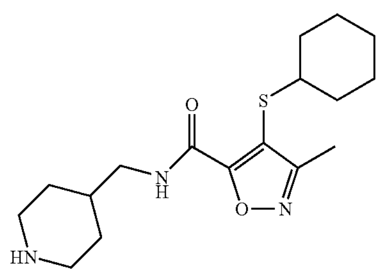 [SMILES: Cc1noc(C(=O)NCC2CCNCC2)c1SC1CCCCC1] | 300 MHz (CDCl3) 1.24-2.17 (m, 16H) 2.36 (s, 3H) 2.64-2.72 (m, 2H) 2.99-3.06 (m, 1H) 3.24 (d, J = 12 Hz, 2H) 3.36-3.44 (m, 2H) 7.62 (s, 1H) |
| B-76 | 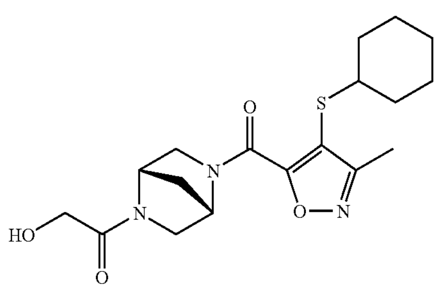 [SMILES: Cc1noc(C(=O)N2C[C@@H]3C[C@H]2CN3C(=O)CO)c1SC1CCCCC1] | 300 MHz (CDCl3) 1.23-2.05 (m, 13H) 2.32 (s, 3H) 3.2 (bs, 1H) 3.49-3.84 (m, 4H) 4.02-4.09 (m, 2H) 5.05-5.15 (m, 2H) |
| B-77 | 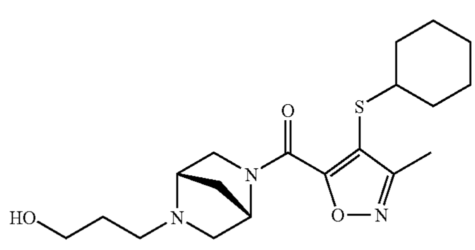 [SMILES: Cc1noc(C(=O)N2C[C@@H]3C[C@H]2CN3CCCO)c1SC1CCCCC1] | 300 MHz (CDCl3) 1.24-1.97 (m, 13H) 2.35 (s, 3H) 2.79-2.94 (m, 4H) 3.06-3.18 (m, 2H) 3.48-3.58 (m, 2H) 3.71-4.92 (m, 4H) |
| B-78 | 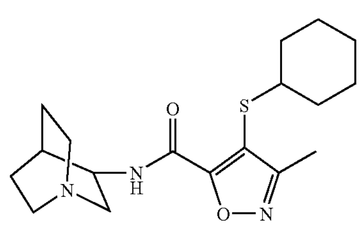 [SMILES: Cc1noc(C(=O)NC2CN3CCC2CC3)c1SC1CCCCC1] | 300 MHz (CDCl3) 1.21-2.07 (m, 16H) 20.6 (s, 3H) 2.61-2.67 (m, 1H) 2.83-3.05 (m, 4H) 3.41-3.49 (m, 1H) 4.21 (bs, 1H) 7.96 (d, J = 7.5 Hz, 1H) |

TABLE 19

| No. | Structure | NMR (CDCl3 or d6-DMSO), MS or m.p. |
| --- | --- | --- |
| B-79 | 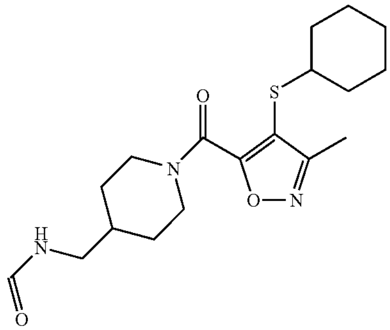 [SMILES: Cc1noc(C(=O)N2CCC(CNC=O)CC2)c1SC1CCCCC1] | 300 MHz (CDCl3) 1.24-1.89 (m, 16H) 2.34 (s, 3H) 2.77-3.28 (m, 4H) 3.57 (d, J = 15.6 Hz, 1H) 4.69 (d, J = 15.6 Hz, 1H) 5.65 (s, 1H) 8.22 (s, 1H) |
| B-80 | 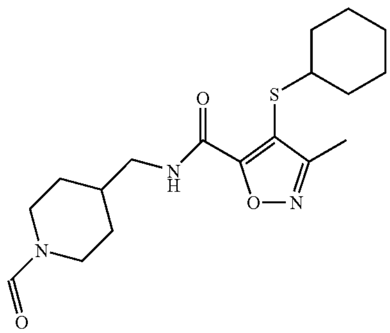 [SMILES: Cc1noc(C(=O)NCC2CCN(C=O)CC2)c1SC1CCCCC1] | 300 MHz (CDCl3) 1.17-2.03 (m, 16H) 2.35 (s, 3H) 2.57-2.69 (m, 2H) 2.98-3.14 (m, 2H) 3.32-3.47 (m, 2H) 3.36-3.44 (m, 2H) 3.66 (d, J = 12.9 Hz, 1H) 4.45 (d, J = 12.9 Hz, 1H) 7.65 (bs, 1H) 8.03 (s, 1H) |
| B-81 | 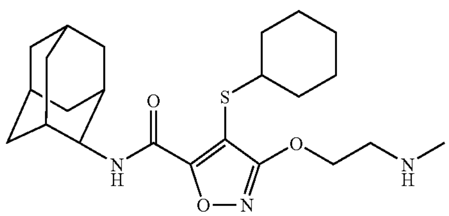 | 400 MHz (DMSO) 1.16-2.00 (m, 24H), 2.63 (s, 3H), 3.20 (br, 1H), 3.48 (br, 2H), 4.05 (d, J = 6.8 Hz, 1H), 4.60 (t, J = 4.8 Hz, 2H), 8.46 (d, J = 7.2 Hz, 1H), 9.33 (br, 2H) |
| B-82 | 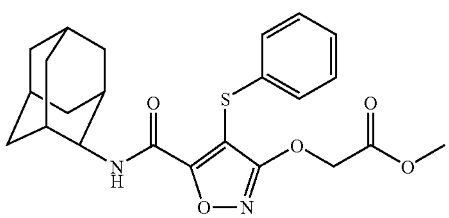 [SMILES: COC(=O)COc1noc(C(=O)NC2C3CC4CC(C3)CC2C4)c1Sc1ccccc1] | 300 MHz (d6-DMSO) 1.48-1.52 (m, 2H), 1.68-1.95 (m, 12H), 3.68 (s, 3H), 3.99-4.02 (m, 1H), 4.99 (s, 2H), 723-7.35 (m, 5H), 8.61 (d, J = 6.6 Hz, 1H) |
| B-83 | 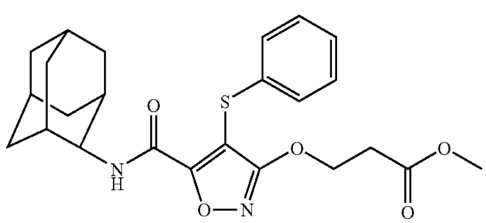 [SMILES: COC(=O)CCOc1noc(C(=O)NC2C3CC4CC(C3)CC2C4)c1Sc1ccccc1] | 300 MHz (d6-DMSO) 1.2-1.94 (m, 14H), 2.75 (t, J = 6 Hz, 2H), 3.53 (s, 3H), 3.98-4.00 (m, 1H), 4.45 (t, J = 6 Hz, 2H), 7.19-7.34 (m, 5H), 8.52 (d, J = 7.2 Hz, 1H) |
| B-84 | 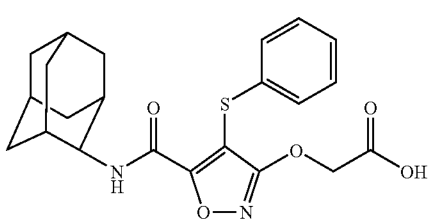 [SMILES: O=C(O)COc1noc(C(=O)NC2C3CC4CC(C3)CC2C4)c1Sc1ccccc1] | 300 MHz (d6-DMSO) 1.02-1.94 (m, 14H), 3.98-4.00 (m, 1H), 4.86 (s, 2H), 7.20-7.34 (m, 5H), 8.60 (d, J = 7.2 Hz, 1H), 13.28 (brs, 1H) |

TABLE 20

| No. | Structure | NMR (CDCl3 or d6-DMSO), MS or m.p. |
|---|---|---|
| B-85 | 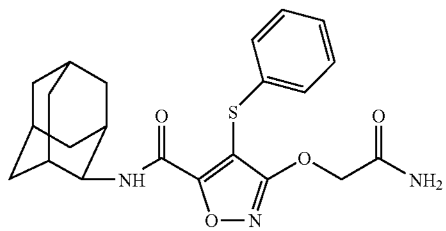 [SMILES: NC(=O)COc1noc(C(=O)NC2C3CC4CC(C3)CC2C4)c1Sc1ccccc1] | 400 MHz (DMSO) 1.48-1.88 (m, 14H), 3.99-4.03 (m, 1H), 4.70 (s, 2H), 7.07-7.34 (m, 7H), 8.53 (d, J = 7.2 Hz, 1H) |
| B-86 | HCl | 300 MHz (DMSO) 1.00-2.20 (m, 29H), 2.84-2.96 (m, 2H), 3.11 (br, 1H), 3.27 (br, 2H), 4.02-4.05 (m, 1H), 4.19 (d, J = 6.6 Hz, 2H), 8.43 (d, J = 7.2 Hz, 1H), 8.68 (br, 1H), 8.99 (br, 1H) |
| B-87 | HCl | 300 MHz (CDCl3) 1.20-1.30 (m, 4H), 1.60-2.00 (m, 14H), 2.48-2.60 (m, 4H), 2.87 (t, J = 5.7 Hz, 2H), 4.25 (m, 1H), 4.47 (t, J = 5.4 Hz, 2H), 7.22-7.56 (m, 5H, 7.70 (d, J = 8.1 Hz, 1H) |
| B-88 | 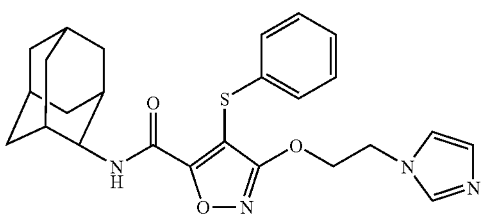 [SMILES: O=C(NC1C2CC3CC(C2)CC1C3)c1onc(OCCn2ccnc2)c1Sc1ccccc1] | 300 MHz (CDCl3) 1.60-2.20 (m, 14H), 4.24 (m, 1H), 4.28 (t, J = 5.1 Hz, 2H), 4.54 (t, J = 5.1 Hz, 2H), 6.74 (s, 1H), 6.97 (s, 1H), 7.22-7.33 (m, 5H), 7.51 (s, 1H), 7.70 (d, J = 8.1 Hz, 1H) |
| B-89 | HCl | 300 MHz (d6-DMSO) 1.20-1.30 (m, 2H), 1.50-1.98 (m, 18H), 2.65-2.80 (m, 2H), 3.10-3.20 (m, 2H), 3.38-3.42 (m, 2H), 4.00 (m, 1H), 4.68 (s, 2H), 7.22-7.38 (m, 2H), 7.52-7.68 (m, 3H), 8.57 (d, J = 7.2 Hz, 1H) |
| B-90 | HCl | 400 MHz (d6-DMSO) 1.09-1.91 (m, 20H), 2.62-2.67 (m, 2H), 3.13-3.16 (m, 2H), 3.98-4.02 (m, 1H), 4.26-4.29 (m, 2H), 7.23-7.36 (m, 5H), 8.50 (d, J = 6.8 Hz, 1H), 8.61-8.86 (brs, 1H) |

TABLE 21

| No. | Structure | NMR (CDCl3 or d6-DMSO), MS or m.p. |
|---|---|---|
| B-91 | 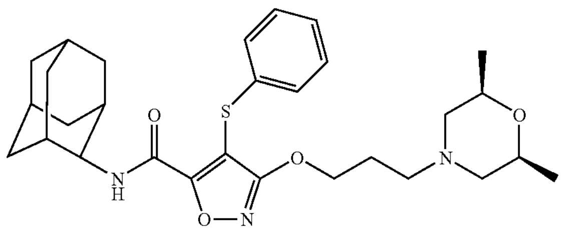 [SMILES: C[C@@H]1CN(CCCOc2noc(C(=O)NC3C4CC5CC(C4)CC3C5)c2Sc2ccccc2)C[C@H](C)O1] | 400 MHz (d6-DMSO) 1.01 (d, J = 2.0 Hz, 6H), 1.43-1.52 (m, 4H), 1.69-1.91 (m, 14H), 2.11 (t, J = 7.2 Hz, 2H), 2.56 (d, J = 7.2 Hz, 2H), 3.45-3.49 (m, 2H), 3.98-4.02 (m, 1H), 4.25 (t, J = 6.0 Hz, 2H), 7.22-7.35 (m, 5H), 8.50 (d, J = 7.2 Hz, 1H) |
| B-92 | 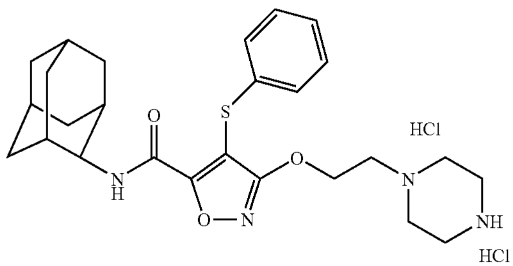 [SMILES: O=C(NC1C2CC3CC(C2)CC1C3)c1onc(OCCN2CCNCC2)c1Sc1ccccc1 ; Cl ; Cl] | 400 MHz (d6-DMSO) 1.49-1.91 (m, 14H), 2.23-2.34 (m, 4H), 2.61 (t, J = 5.2 Hz, 2H), 2.69-2.70 (m, 4H), 3.45-3.81 (brs, 3H), 4.33 (t, J = 5.2 Hz, 2H), 7.22-7.35 (m, 5H), 8.51 (d, J = 7.2 Hz, 1H) |
| B-93 | 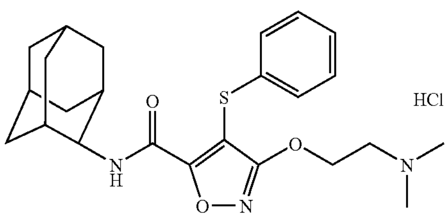 [SMILES: CN(C)CCOc1noc(C(=O)NC2C3CC4CC(C3)CC2C4)c1Sc1ccccc1 ; Cl] | 300 MHz (d6-DMSO) 1.45-1.58 (m, 2H), 1.65-1.95 (m, 12H), 2.60 (s, 6H), 3.44 (t, J = 4.6 Hz, 2H), 4.01 (d, J = 7.7 Hz, 1H), 4.65 (t, J = 4.8 Hz, 2H), 7.20-7.38 (m, 5H), 8.56 (d, J = 7.2 Hz, 1H) |
| B-94 | 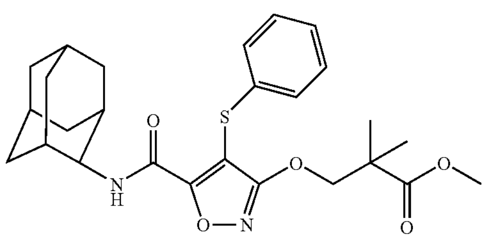 [SMILES: COC(=O)C(C)(C)COc1noc(C(=O)NC2C3CC4CC(C3)CC2C4)c1Sc1ccccc1] | 300 MHz (d6-DMSO) 1.05 (s, 6H), 1.50-1.99 (m, 14H), 3.50 (s, 3H), 4.02-4.04 (m, 1H), 4.22 (s, 2H), 7.22-7.35 (m, 5H), 8.54 (d, J = 6.9 Hz, 1H) |
| B-95 | 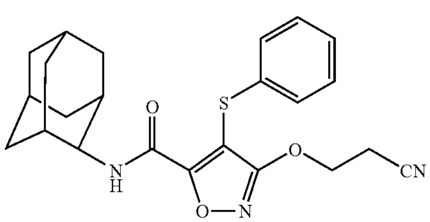 [SMILES: N#CCCOc1noc(C(=O)NC2C3CC4CC(C3)CC2C4)c1Sc1ccccc1] | 300 MHz (CDCl3) 1.58-2.00 (m, 14H), 2.78 (t, J = 6.3 Hz, 2H), 4.26 (d, J = 8.4 Hz, 1H), 4.49 (t, J = 6.3 Hz, 2H), 7.30-7.35 (m, 5H), 7.72 (d, J = 8.4 Hz, 1H) |
| B-96 | 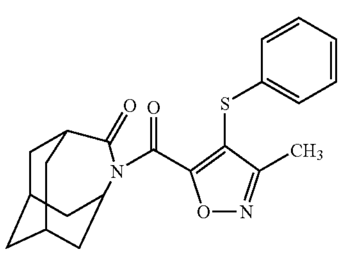 [SMILES: Cc1noc(C(=O)N2C(=O)C3CC4CC(C3)CC2C4)c1Sc1ccccc1] | 300 MHz (CDCl3); 1.60-2.14 (m, 12H), 2.10 (s, 3H), 2.88 (t, J = 6.3 Hz, 1H), 4.96 (brs, 1H), 7.1-7.3 (m, 5H) |

TABLE 22

| No. | Structure | NMR (CDCl3 or d6-DMSO), MS or m.p. |
|---|---|---|
| B-97 | 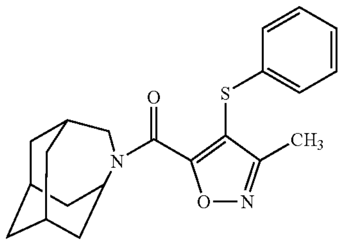 [SMILES: Cc1noc(C(=O)N2CC3CC4CC(C3)CC2C4)c1Sc1ccccc1] | 300 MHz (CDCl3); 1.42-2.06 (m, 10H), 2.36 (brs, 1H), 3.43 (d, J = 3.9 Hz, 1H), 3.73 (d, J = 3.6 Hz, 2H), 3.90 (t, J = 5.1 Hz, 1H), 4.98 (brs, 1H), 7.1-7.4 (m, 5H) |
| B-98 | 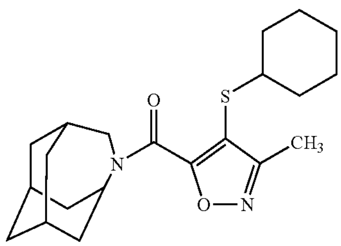 [SMILES: Cc1noc(C(=O)N2CC3CC4CC(C3)CC2C4)c1SC1CCCCC1] | 300 MHz (CDCl3); 1.20-1.38 (m, 4H), 1.46-1.8 (m, 8H), 1.86-2.05 (m, 1H), 2.20 (brs, 1H), 2.33 (s, 3H), 2.39 (brs, 1H), 2.96 (brs, 1H), 3.44 (d, J = 3.6 Hz, 1H), 3.75 (d, J = 3.6 Hz, 1H), 3.84 (t, J = 5.4 Hz, 1H), 5.02 (brs, 1H) |
| B-99 | 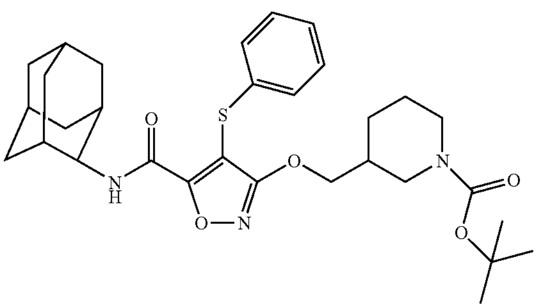 [SMILES: CC(C)(C)OC(=O)N1CCCC(COc2noc(C(=O)NC3C4CC5CC(C4)CC3C5)c2Sc2ccccc2)C1] | 400 MHz (d6-DMSO) 0.91-1.99 (m, 29H), 2.71-2.76 (m, 1H), 3.65-3.11 (m, 2H), 4.00-4.02 (m, 1H), 4.10 (d, J = 6.4 Hz, 1H), 7.23-7.55 (m, 5H), 8.52 (d, J = 9.2 Hz, 1H) |
| B-100 | 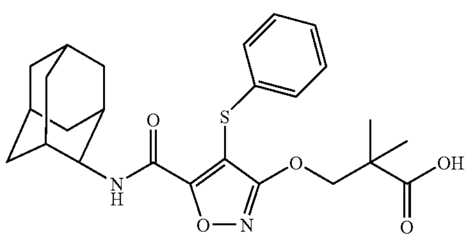 [SMILES: CC(C)(COc1noc(C(=O)NC2C3CC4CC(C3)CC2C4)c1Sc1ccccc1)C(=O)O] | 400 MHz (d6-DMSO) 1.02 (s, 6H), 1.51-1.97 (m, 14H), 4.01-4.02 (m, 1H), 4.21 (s, 3H), 7.23-7.34 (m, 5H), 8.51 (d, J = 7.2 Hz, 1H), 12.02-12.64 (brs, 1H) |
| B-101 | 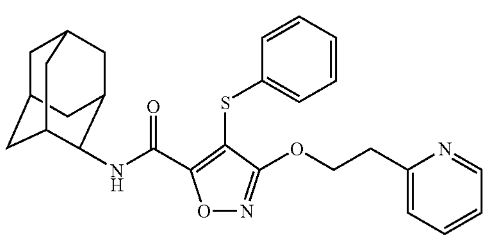 [SMILES: O=C(NC1C2CC3CC(C2)CC1C3)c1onc(OCCc2ccccn2)c1Sc1ccccc1] | 300 MHz (CDCl3) 1.60-2.00 (m, 14H), 3.20 (t, J = 6.6 Hz, 2H), 4.22 (m, 1H), 4.67 (t, J = 6.3 Hz, 2H), 7.02-7.30 (m, 7H), 7.49 (dd, J = 2.1, 7.8 Hz, 1H), 7.69 (d, J = 8.4 Hz, 1H), 8.49 (d, J = 4.2 Hz, 1H) |
| B-102 | 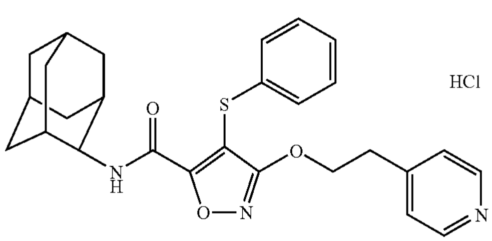 [SMILES: O=C(NC1C2CC3CC(C2)CC1C3)c1onc(OCCc2ccncc2)c1Sc1ccccc1 ; Cl] | 300 MHz (d6-DMSO) 1.44-1.58 (m, 2H), 1.68-1.95 (m, 14H), 3.28 (t, J = 5.7 Hz, 2H), 4.00 (d, J = 7.5 Hz, 1H), 4.63 (t, J = 6.0 Hz, 2H), 7.06-7.15 (m, 2H), 7.20-7.28 (m, 3H), 7.78 (d, J = 6.3 Hz, 1H), 8.52 (d, J = 7.2 Hz, 1H), 8.70 (d, J = 6.3 Hz, 2H) |

TABLE 23

| No. | Structure | NMR (CDCl3 or d6-DMSO), MS or m.p. |
|---|---|---|
| B-103 | 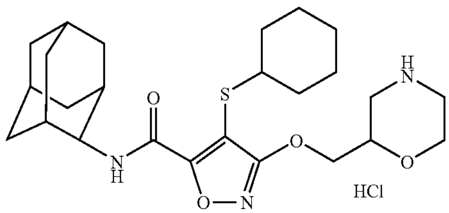 [SMILES: O=C(NC1C2CC3CC(C2)CC1C3)c1onc(OCC2CNCCO2)c1SC1CCCCC1 ; Cl] | 300 MHz (d6-DMSO) 1.15-1.21 (m, 2H), 1.46-1.56 (m, 2H), 1.67-1.98 (m, 10H), 2.65-2.73 (m, 1H), 2.81-2.90 (m, 1H), 3.10-3.20 (m, 2H), 3.65-3.73 (m, 1H), 3.92-4.05 (m, 3H), 4.27-4.38 (m, 2H), 7.26-7.36 (m, 5H), 8.53 (d, J = 6.6 Hz, 1H), 9.19 (br, 2H) |
| B-104 | 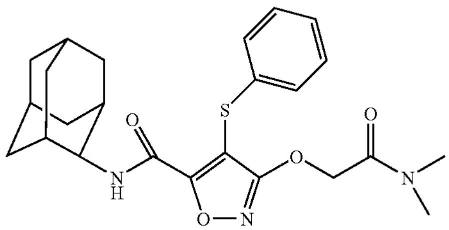 [SMILES: CN(C)C(=O)COc1noc(C(=O)NC2C3CC4CC(C3)CC2C4)c1Sc1ccccc1] | 400 MHz (d6-DMSO) 1.47-1.99 (m, 14H), 2.82 (s, 3H), 2.89 (s, 3H), 3.98-4.04 (m, 1H), 5.06 (s, 2H), 7.22-7.33 (m, 5H), 8.55 (d, J = 7.5 Hz, 1H) |
| B-105 | 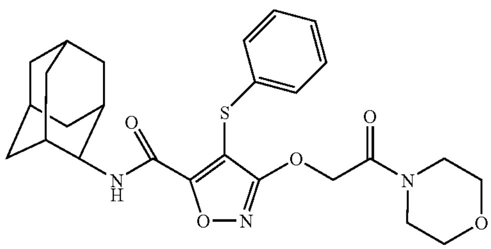 [SMILES: O=C(NC1C2CC3CC(C2)CC1C3)c1onc(OCC(=O)N2CCOCC2)c1Sc1ccccc1] | 400 MHz (d6-DMSO) 1.16-1.99 (m, 14H), 3.32-3.41 (m, 4H), 3.51-3.55 (m, 4H), 3.96-4.00 (m, 1H), 5.10 (s, 2H), 7.18-7.33 (m, 5H), 8.55 (d, J = 8.0 Hz, 1H) |
| B-106 | 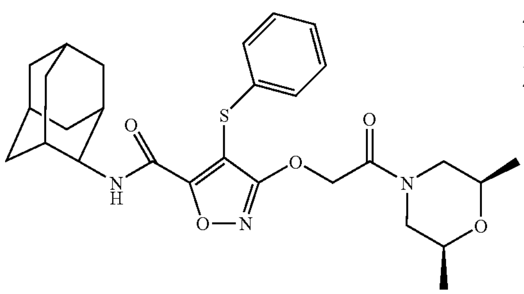 [SMILES: C[C@@H]1CN(C(=O)COc2noc(C(=O)NC3C4CC5CC(C4)CC3C5)c2Sc2ccccc2)C[C@H](C)O1] | 400 MHz (d6-DMSO) 0.93-1.99 (m, 20H), 2.23-2.31 (m, 1H), 2.50-2.67 (m, 1H), 3.42-3.60 (m, 3H), 3.98-4.06 (m, 1H), 4.13-4.16 (m, 1H), 5.02 (d, J = 14.8 Hz, 1H), 5.18 (d, J = 14.8 Hz, 1H), 7.20-7.33 (m, 5H), 8.55 (d, J = 6.8 Hz, 1H) |
| B-107 | 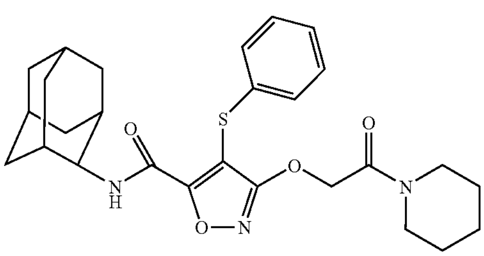 [SMILES: O=C(NC1C2CC3CC(C2)CC1C3)c1onc(OCC(=O)N2CCCCC2)c1Sc1ccccc1] | 400 MHz (d6-DMSO) 1.11-1.99 (m, 20H), 3.32-3.43 (m, 4H), 3.98-4.02 (m, 1H), 5.07 (s, 2H), 7.22-7.33 (m, 5H), 8.55 (d, J = 7.2 Hz, 1H) |
| B-108 | 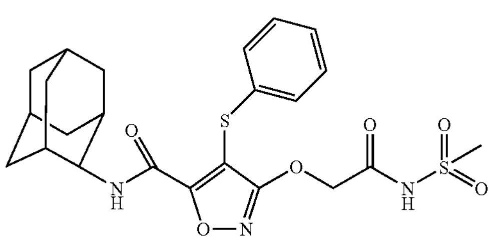 [SMILES: CS(=O)(=O)NC(=O)COc1noc(C(=O)NC2C3CC4CC(C3)CC2C4)c1Sc1ccccc1] | 400 MHz (d6-DMSO) 1.16-1.99 (m, 14H), 3.24 (s, 3H), 3.98-4.02 (m, 1H), 4.91 (s, 2H), 7.17-7.35 (m, 5H), 8.89 (d, J = 8.0 Hz, 1H) |

TABLE 24

| No. | Structure | NMR (CDCl3 or d6-DMSO), MS or m.p. |
|---|---|---|
| B-109 | 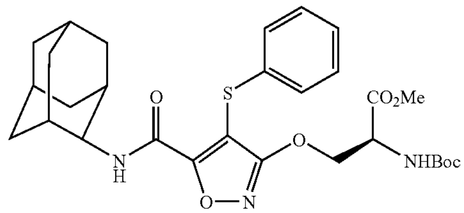 [SMILES: COC(=O)[C@@H](COc1noc(C(=O)NC2C3CC4CC(C3)CC2C4)c1Sc1ccccc1)NC(=O)OC(C)(C)C] | 300 MHz (CDCl3) 1.46 (s, 9H), 1.60-2.00 (m, 14H), 3.66 (s, 3H), 4.26 (d, J = 7.2 Hz, 1H), 4.43 (dd, J = 3.0, 10.8 Hz, 1H), 4.65-4.68 (m, 2H), 4.95 (d, J = 8.4 Hz, 1H), 7.30-7.40 (m, 5H), 7.61 (d, J = 7.5 Hz, 1H) |
| B-110 | 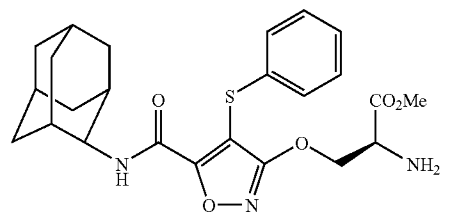 [SMILES: COC(=O)[C@H](N)COc1noc(C(=O)NC2C3CC4CC(C3)CC2C4)c1Sc1ccccc1] | 300 MHz (CDCl3) 1.60-2.00 (m, 14H), 3.67 (s, 3H), 3.89 (s, 1H), 4.13 (d, J = 7.5 Hz, 1H), 4.56 (d, J = 3.3 Hz, 2H), 7.30 (3, 5H), 7.64 (d, J = 8.4 Hz, 1H) |
| B-111 | 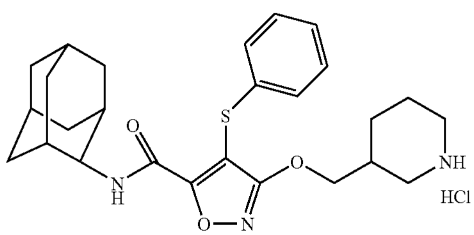 [SMILES: O=C(NC1C2CC3CC(C2)CC1C3)c1onc(OCC2CCCNC2)c1Sc1ccccc1 ; Cl] | 400 MHz (d6-DMSO) 1.5-1.99 (m, 20H), 2.13-2.16 (m, 1H), 3.02-3.19 (m, 2H), 3.96-4.03 (m, 1H), 4.14-4.17 (m, 2H), 7.22-7.38 (m, 5H), 8.50 (d, J = 6.4 Hz, 1H), 8.80-8.89 (brs, 1H) |
| B-112 | 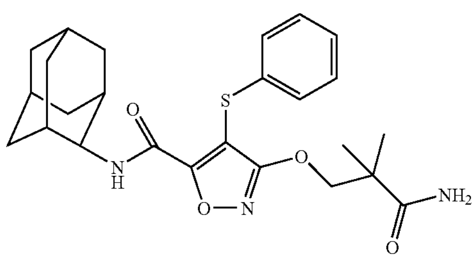 [SMILES: CC(C)(COc1noc(C(=O)NC2C3CC4CC(C3)CC2C4)c1Sc1ccccc1)C(N)=O] | 400 MHz (d6-DMSO) 0.99 (s, 6H), 1.50-1.99 (m, 14H), 4.00-4.02 (m, 1H), 4.18 (s, 2H), 6.91 (s, 1H), 7.12 (s, 1H), 7.23-7.35 (m, 5H), 8.50 (d, J = 6.8 Hz, 1H) |
| B-113 | 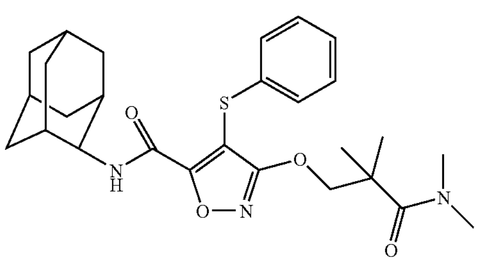 [SMILES: CN(C)C(=O)C(C)(C)COc1noc(C(=O)NC2C3CC4CC(C3)CC2C4)c1Sc1ccccc1] | 400 MHz (d6-DMSO) 1.09 (s, 6H), 1.50-1.99 (m, 14H), 2.88 (s, 6H), 4.00-4.04 (m, 1H), 4.22 (s, 2H), 7.24-7.34 (m, 5H), 8.51 (d, J = 6.8 Hz, 1H) |
| B-114 | 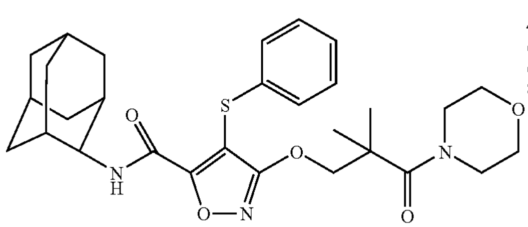 [SMILES: CC(C)(COc1noc(C(=O)NC2C3CC4CC(C3)CC2C4)c1Sc1ccccc1)C(=O)N1CCOCC1] | 400 MHz (d6-DMSO) 1.09 (s, 6H), 1.50-1.99 (m, 14H), 3.45-3.52 (m, 8H), 4.00-4.02 (m, 1H), 4.22 (s, 2H), 7.22-7.33 (m, 5H), 8.50 (d, J = 6.8 Hz, 1H) |

TABLE 25

| No. | Structure | NMR (CDCl3 or d6-DMSO), MS or m.p. |
|---|---|---|
| B-115 | 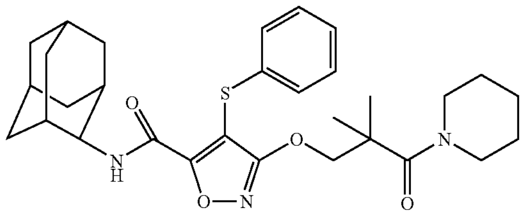 [SMILES: CC(C)(COc1noc(C(=O)NC2C3CC4CC(C3)CC2C4)c1Sc1ccccc1)C(=O)N1CCCCC1] | 400 MHz (d6-DMSO) 1.08 (s, 6H), 1.24-1.99 (m, 20H), 3.42-3.50 (m, 4H), 4.00-4.02 (m, 1H), 4.21 (s, 2H), 7.22-7.34 (m, 5H), 8.50 (d, J = 6.4 Hz, 1H) |
| B-116 | 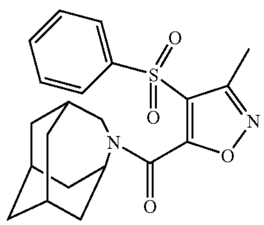 [SMILES: Cc1noc(C(=O)N2CC3CC4CC(C3)CC2C4)c1S(=O)(=O)c1ccccc1] | 400 MHz (d6-DMSO); 1.42-1.99 (m, 12H), 2.25 (brs, 1H), 2.33 (s, 3H), 3.37 (d, J = 3.6 Hz, 1H), 3.65 (d, J = 3.6 Hz, 1H), 3.75 (brs, 1H), 7.69-7.72 (m, 2H), 7.78-7.82 (m, 1H), 8.01-8.04 (m, 2H) |
| B-117 | 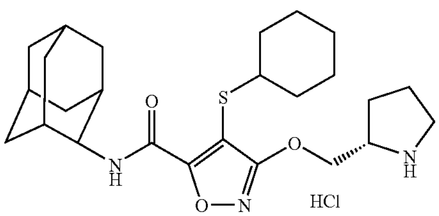 [SMILES: O=C(NC1C2CC3CC(C2)CC1C3)c1onc(OC[C@@H]2CCCN2)c1SC1CCCCC1 ; Cl] | 300 MHz (d6-DMSO) 1.44-2.04 (m, 14H), 2.96-3.05 (m, 1H), 3.09-3.17 (m, 1H), 3.82-3.94 (m, 1H), 3.96-4.04 (m, 1H), 4.40-4.53 (m, 2H), 7.24-7.38 (m, 5H), 8.54 (d, J = 7.2 Hz, 1H), 9.19 (br, 2H) |
| B-118 | 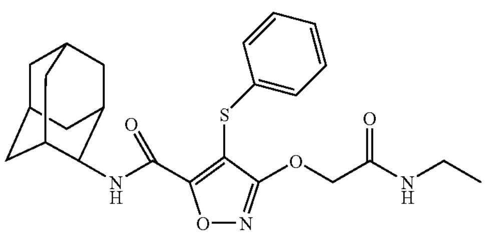 [SMILES: CCNC(=O)COc1noc(C(=O)NC2C3CC4CC(C3)CC2C4)c1Sc1ccccc1] | 400 MHz (d6-DMSO) 1.01 (t, J = 7.2 Hz, 3H), 1.48-1.99 (m, 14H), 3.04-3.13 (m, 2H), 3.98-4.00 (m, 1H), 4.70 (s, 2H), 7.21-7.34 (m, 5H), 8.53 (d, J = 6.4 Hz, 1H) |
| B-119 | 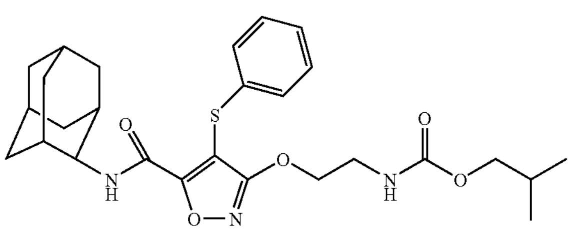 [SMILES: CC(C)COC(=O)NCCOc1noc(C(=O)NC2C3CC4CC(C3)CC2C4)c1Sc1ccccc1] | 400 MHz (d6-DMSO) 0.85 (d, J = 6.8 Hz, 6H), 1.48-1.90 (m, 15H), 3.30-3.34 (m, 2H), 3.70 (d, J = 6.8 Hz, 2H), 3.99-4.00 (m, 1H), 4.26 (t, J = 5.2 Hz, 2H), 7.14-7.34 (m, 6H), 8.48 (d, J = 6.8 Hz, 1H) |
| B-120 | 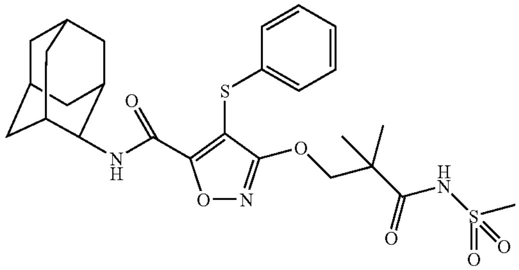 [SMILES: CC(C)(COc1noc(C(=O)NC2C3CC4CC(C3)CC2C4)c1Sc1ccccc1)C(=O)NS(C)(=O)=O] | 400 MHz (d6-DMSO) 1.06 (s, 6H), 1.50-1.95 (m, 14H), 3.12 (s, 3H), 3.98-4.04 (m, 1H), 4.32 (s, 2H), 7.23-7.35 (m, 5H), 8.51 (d, J = 7.8 Hz, 1H), 11.50 (brs, 1H) |

TABLE 26

| No. | Structure | NMR (CDCl3 or d6-DMSO), MS or m.p. |
|---|---|---|
| B-121 | 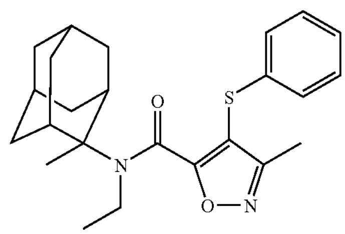 [SMILES: CCN(C(=O)c1onc(C)c1Sc1ccccc1)C1(C)C2CC3CC(C2)CC1C3] | 400 MHz (DMSO) 1.08 (t, J = 6.8 Hz, 3H), 1.37 (d, J = 12.0 Hz, 1H), 1.52-2.00 (m, 16H), 2.15 (s, 3H), 3.19 (br, 2H), 7.16-7.38 (m, 5H) |
| B-122 | 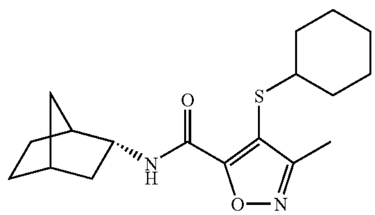 [SMILES: Cc1noc(C(=O)N[C@@H]2CC3CCC2C3)c1SC1CCCCC1] | 400 MHz (DMSO) 1.03-1.11 (m, 1H), 1.22-1.97 (m, 17H), 2.18 (br, 1H), 2.29 (s, 3H), 2.40 (br, 1H), 3.10 (br, 1H), 4.09 (bmr, 1H), 8.67 (d, J = 6.4 Hz, 1H) |

TABLE 27

| No. | Structure |
|---|---|
| B-123 | 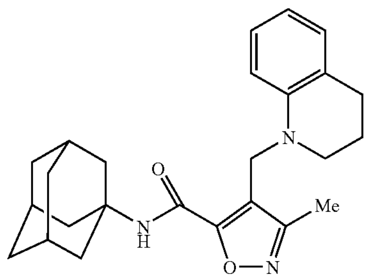 [SMILES: Cc1noc(C(=O)NC23CC4CC(CC(C4)C2)C3)c1CN1CCCc2ccccc21] |
| B-124 | 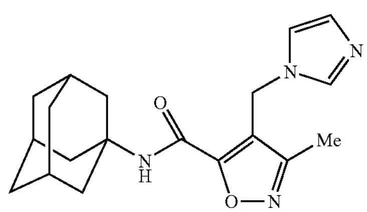 [SMILES: Cc1noc(C(=O)NC23CC4CC(CC(C4)C2)C3)c1Cn1ccnc1] |
| B-125 | 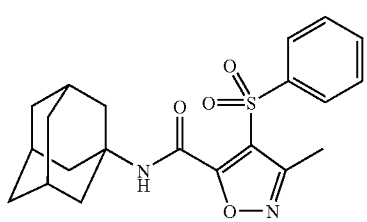 [SMILES: Cc1noc(C(=O)NC23CC4CC(CC(C4)C2)C3)c1S(=O)(=O)c1ccccc1] |
| B-126 | 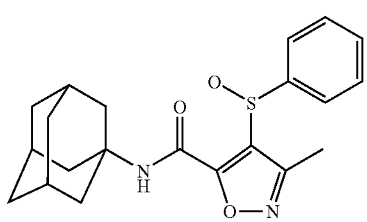 |

TABLE 27-continued

| No. | Structure |
|---|---|
| B-127 | 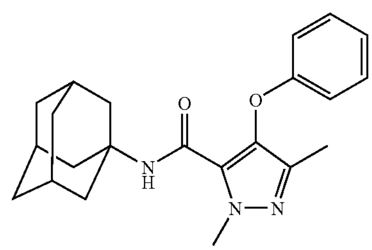 [SMILES: Cc1nn(C)c(C(=O)NC23CC4CC(CC(C4)C2)C3)c1Oc1ccccc1] |
| B-128 | 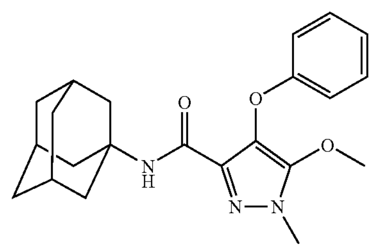 [SMILES: COc1c(Oc2ccccc2)c(C(=O)NC23CC4CC(CC(C4)C2)C3)nn1C] |

TABLE 28

| No. | Structure |
|---|---|
| B-129 | 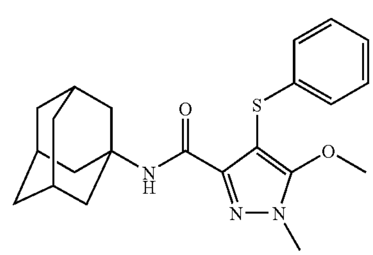 |

TABLE 28-continued

| No. | Structure |
|---|---|
| B-130 | 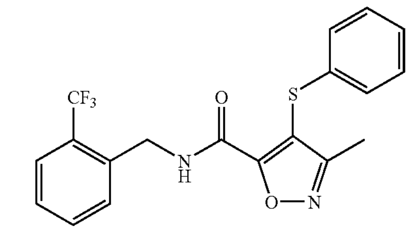 [SMILES: Cc1noc(C(=O)NCc2ccccc2C(F)(F)F)c1Sc1ccccc1] |
| B-131 | 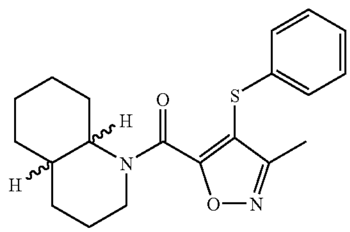 [SMILES: Cc1noc(C(=O)N2CCCC3CCCCC32)c1Sc1ccccc1] |
| B-132 | 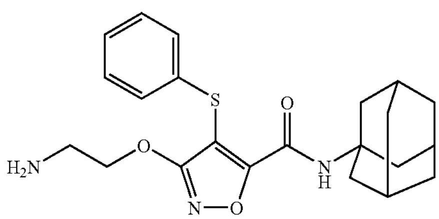 [SMILES: NCCOc1noc(C(=O)NC23CC4CC(CC(C4)C2)C3)c1Sc1ccccc1] |
| B-133 | 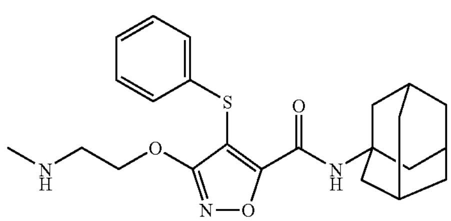 [SMILES: CNCCOc1noc(C(=O)NC23CC4CC(CC(C4)C2)C3)c1Sc1ccccc1] |
| B-134 | 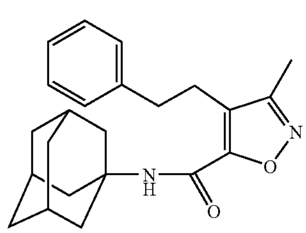 [SMILES: Cc1noc(C(=O)NC23CC4CC(CC(C4)C2)C3)c1CCc1ccccc1] |
| B-135 | 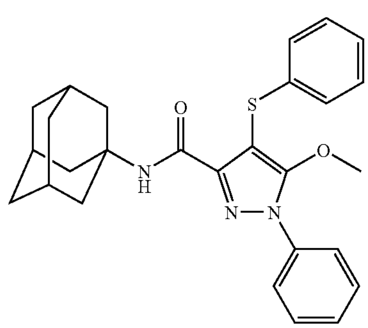 [SMILES: COc1c(Sc2ccccc2)c(C(=O)NC23CC4CC(CC(C4)C2)C3)nn1-c1ccccc1] |
| B-136 | |
| B-137 | |
| B-138 | |
| B-139 | |
| B-140 | |

TABLE 29
| No. | Structure |
|---|---|
| B-141 | 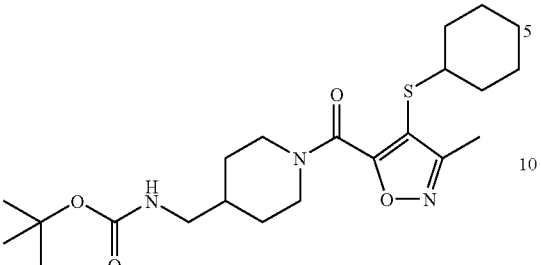 |
| B-142 | 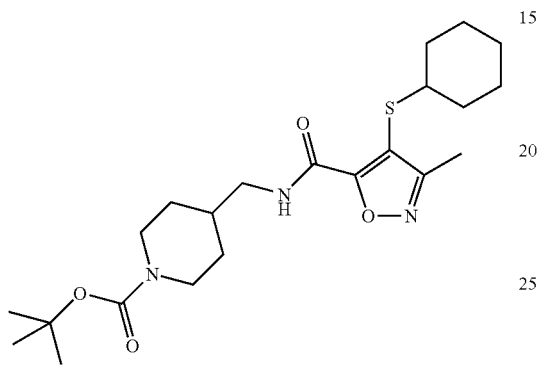 |
| B-143 | 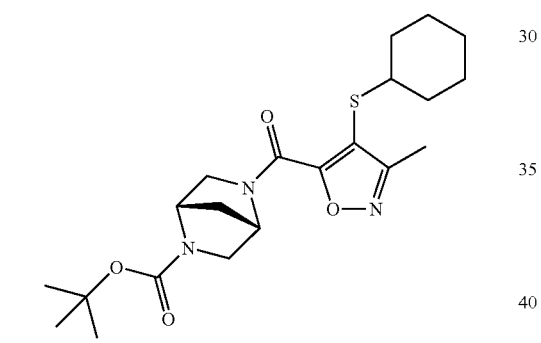 |
TABLE 29-continued
| No. | Structure |
|---|---|
| B-144 | 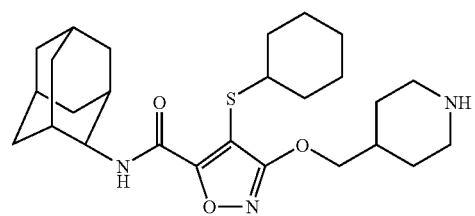 [SMILES: O=C(NC1C2CC3CC(C2)CC1C3)c1onc(OCC2CCNCC2)c1SC1CCCCC1] |
| B-145 | 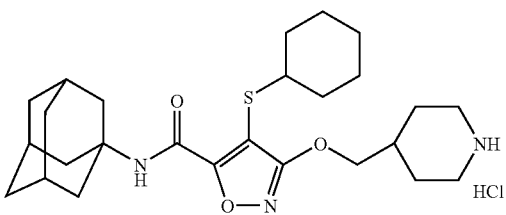 [SMILES: O=C(NC12CC3CC(CC(C3)C1)C2)c1onc(OCC2CCNCC2)c1SC1CCCCC1 ; Cl] |
| B-146 | 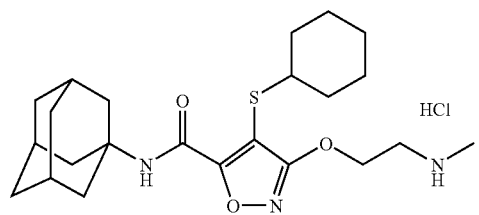 [SMILES: CNCCOc1noc(C(=O)NC23CC4CC(CC(C4)C2)C3)c1SC1CCCCC1 ; Cl] |
TABLE 30
| No. | Structure | NMR (CDCl3 or d6-DMSO) |
|---|---|---|
| C-1 | 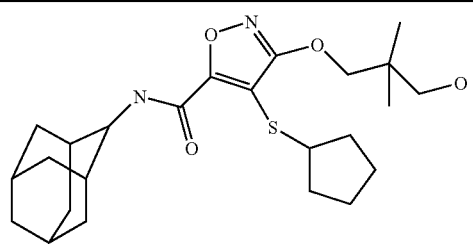 | (CDCl3); 1.03 (s, 6H), 1.59-2.01 (m, 22H), 3.47 (s, 2H), 3.60 (m, 1H), 4.20 (s, 2H), 4.30 (m, 1H), 4.33 (s, 2H), 8.10 (d, J = 8.1 Hz, 1H) |
| C-2 | 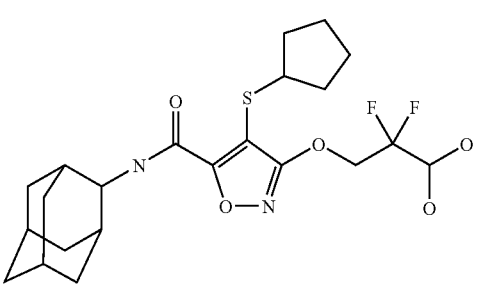 [SMILES: O=C(NC1C2CC3CC(C2)CC1C3)c1onc(OCC(F)(F)C(O)O)c1SC1CCCC1] | (DMSO-d6); 1.44-2.04 (m, 22H), 3.79 (m, 1H), 4.03 (m, 1H), 4.88 (t, J = 13.8 Hz, 2H), 8.47 (d, J = 7.5 Hz, 1H) |

TABLE 30-continued

| No. | Structure | NMR (CDCl3 or d6-DMSO) |
|---|---|---|
| C-3 | 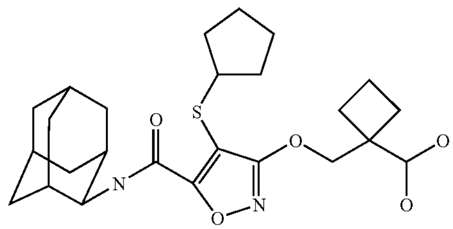 [SMILES: O=C(NC1C2CC3CC(C2)CC1C3)c1onc(OCC2(C(O)O)CCC2)c1SC1CCCC1] | (DMSO-d6); 1.44-2.04 (m, 22H), 3.81 (m, 1H), 4.03 (m, 1H), 4.33 (s, 2H), 8.44 (d, J = 6.9 Hz, 1H) |
| C-4 | 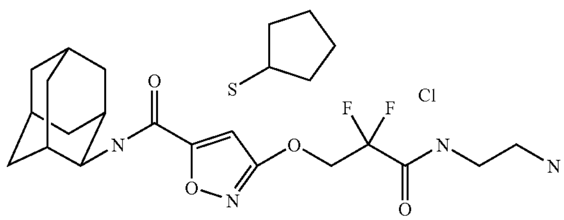 | (DMSO-d6); 1.44-2.04 (m, 22H), 2.73-2.95 (m, 2H), 3.40-4.05 (m, 2H), 4.03 (d, J = 6.9 Hz, 1H), 4.89 (t, J = 13.8 Hz, 2H), 8.11 (br s, 2H), 8.46 (d, J = 7.2 Hz, 1H), 9.26 (m, 1H) |
| C-5 | 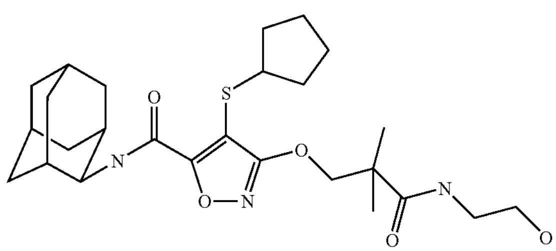 [SMILES: CC(C)(COc1noc(C(=O)NC2C3CC4CC(C3)CC2C4)c1SC1CCCC1)C(=O)NCCO] | (DMSO-d6); 1.20 (m, 6H), 1.39-1.99 (m, 26H), 3.09-3.16 (m, 2H), 3.36-3.56 (m, 2H), 3.55 (m, 1H), 4.03 (d, 1H, J = 9.0 Hz), 4.64 (t, J = 5.4 Hz, 1H), 7.65 (m, 1H), 8.40 (d, J = 7.2 Hz, 1H) |
| C-6 | 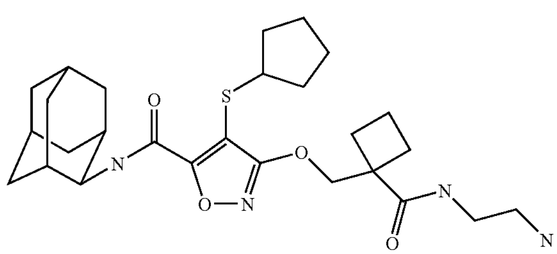 [SMILES: NCCNC(=O)C1(COc2noc(C(=O)NC3C4CC5CC(C4)CC3C5)c2SC2CCCC2)CCC1] | (DMSO-d6); 1.35-1.98 (m, 22H), 2.52-2.57 (m, 2H), 3.03-3.09 (m, 2H), 3.50-3.57 (m, 1H), 4.03 (d, J = 9.0 Hz, 1H), 4.52 (s, 2H), 7.73 (m, 1H), 8.40 (d, J = 7.2 Hz, 1H) |

TABLE 31

| No. | Structure | NMR (CDCl3 or d6-DMSO) |
|---|---|---|
| C-7 | 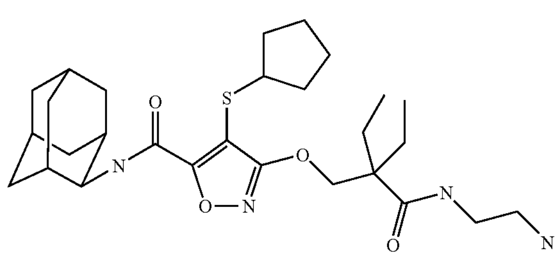 [SMILES: CCC(CC)(COc1noc(C(=O)NC2C3CC4CC(C3)CC2C4)c1SC1CCCC1)C(=O)NCCN] | (DMSO-d6); 0.73-0.79 (m, 6H), 1.39-1.99 (m, 26H), 2.52-2.57 (m, 2H), 3.06-3.09 (m, 2H), 3.53 (m, 1H), 4.03 (d, 1H, J = 9.0 Hz), 4.33 (s, 2H), 7.73 (m, 1H), 8.43 (d, J = 7.2 Hz, 1H) |

TABLE 31-continued

| No. | Structure | NMR (CDCl3 or d6-DMSO) |
|---|---|---|
| C-8 | 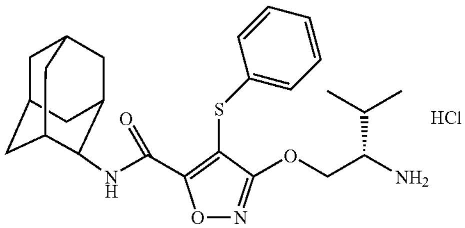 [SMILES: CC(C)[C@H](N)COc1noc(C(=O)NC2C3CC4CC(C3)CC2C4)c1Sc1ccccc1 ; Cl] | (DMSO-d6); 0.79 (d, J = 6.9 Hz, 3H), 0.88 (d, J = 6.9 Hz, 3H), 1.47-1.56 (m, 2H), 1.67-1.95 (m, 12H), 3.19-3.26 (m, 1H), 3.98-4.03 (m, 1H), 4.34-4.49 (m, 2H), 7.25-7.36 (m, 5H), 8.15-8.37 (br, 2H), 8.54 (d, J = 7.2 Hz, 1H) |
| C-9 | 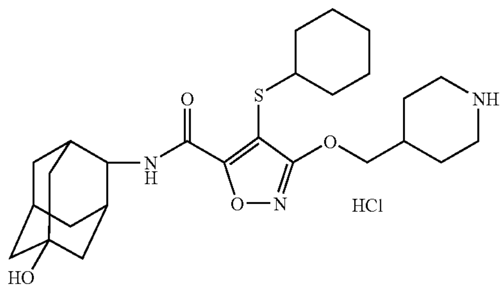 [SMILES: O=C(NC1C2CC3CC1CC(O)(C3)C2)c1onc(OCC2CCNCC2)c1SC1CCCCC1 ; Cl] | (DMSO-d6); 1.15-2.20 (m, 28H), 2.86-2.95 (m, 2H), 3.04-3.16 (m, 1H), 3.22-3.35 (m, 2H), 3.92-3.98 (m, 1H), 4.19 (d, J = 6.3 Hz, 2H), 4.50 (br. s, 1H), 8.39 (d, J = 7.2 Hz, 1H) |
| C-10 | 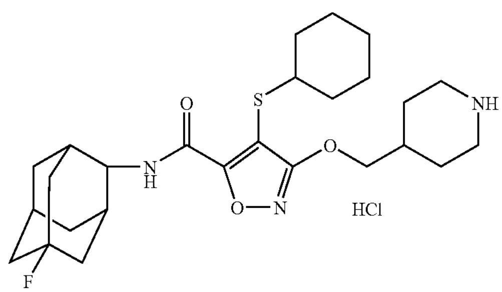 [SMILES: O=C(NC1C2CC3CC1CC(F)(C3)C2)c1onc(OCC2CCNCC2)c1SC1CCCCC1 ; Cl] | (DMSO-d6); 1.14-2.25 (m, 28H), 2.84-2.96 (m, 2H), 3.04-3.16 (m, 1H), 3.25-3.32 (m, 2H), 3.98-4.05 (m, 1H), 4.18 (d, J = 6.3 Hz, 2H), 8.44 (d, H = 7.2 Hz, 1H) |
| C-11 | 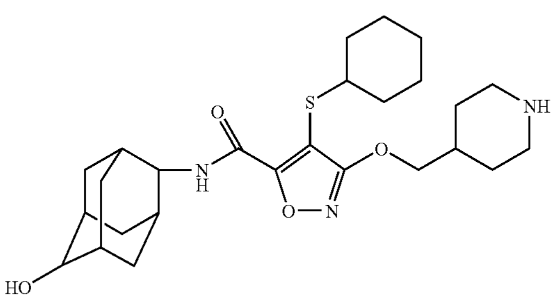 [SMILES: O=C(NC1C2CC3CC1CC(C2)C3O)c1onc(OCC2CCNCC2)c1SC1CCCCC1] | (DMSO-d6); 1.11-2.21 (m, 27H), 2.40-2.47 (m, 2H), 2.90-2.98 (m, 2H), 3.06-3.20 (m, 1H), 3.62-3.68 (m, 1H), 3.93-4.00 (m, 1H), 4.11 (d, J = 6.0 Hz, 2H), 4.64-4.68 (br, 1H), 8.43 (d, J = 7.2 Hz, 1H) |
| C-12 | 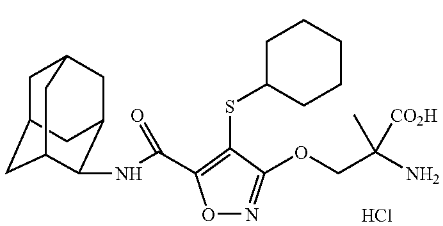 [SMILES: CC(N)(COc1noc(C(=O)NC2C3CC4CC(C3)CC2C4)c1SC1CCCCC1)C(=O)O ; Cl] | (DMSO-d6); 1.14-2.02 (m, 27H), 3.12-3.24 (m, 1H), 4.01-4.08 (m, 1H), 4.59 (s, 2H), 8.47 (d, J = 7.2 Hz, 1H) |

TABLE 32

| No. | Structure | NMR (CDCl3 or d6-DMSO) |
|---|---|---|
| C-13 | 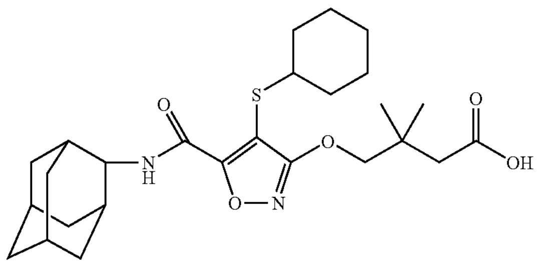 [SMILES: CC(C)(COc1noc(C(=O)NC2C3CC4CC(C3)CC2C4)c1SC1CCCCC1)CC(=O)O] | (CDCl3); 1.15-2.05 (m, 24H), 1.18 (s, 6H), 2.47 (s, 2H), 3.09-3.17 (m, 1H), 4.18 (s, 1H), 4.25-4.32 (m, 1H), 8.16 (d, J = 8.1 Hz, 1H) |
| C-14 | 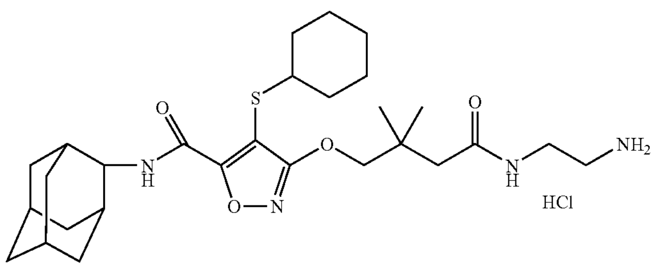 [SMILES: CC(C)(COc1noc(C(=O)NC2C3CC4CC(C3)CC2C4)c1SC1CCCCC1)CC(=O)NCCN ; Cl] | (DMSO-d6): 1.06 (s, 6H), 1.18-2.03 (m, 24H), 2.19 (s, 2H), 2.83 (t, J = 6.3 Hz, 2H), 3.08-3.20 (m, 1H), 3.25-3.32 (m, 2H), 4.01-4.07 (m, 1H), 4.15 (s, 2H), 7.82-7.94 (br, 2H), 8.19 (t, J = 5.4 Hz, 1H), 8.42 (d, J = 7.8 Hz, 1H) |
| C-15 | 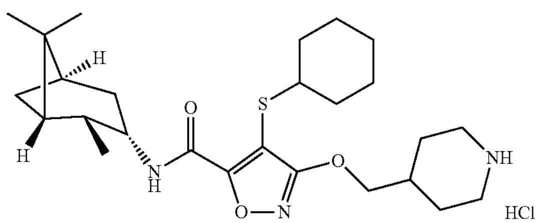 [SMILES: C[C@H]1[C@@H](NC(=O)c2onc(OCC3CCNCC3)c2SC2CCCCC2)C[C@H]2C[C@@H]1C2(C)C ; Cl] | (DMSO-d6); 1.03 (s, 3H), 1.04 (d, J = 7.2 Hz, 3H), 1.22 (s, 3H), 1.11-2.43 (m, 25H), 2.88-2.96 (m, 2H) 3.20 (m, 1H), 3.28 (bs, 1H), 4.18 (d, J = 6.6 Hz, 2H) 4.22-4.31 (m, 1H), 8.70 (bs, 1H), 8.79 (d, J = 8.4 Hz, 1H), 8.99 (bs, 1H) |
| C-16 | 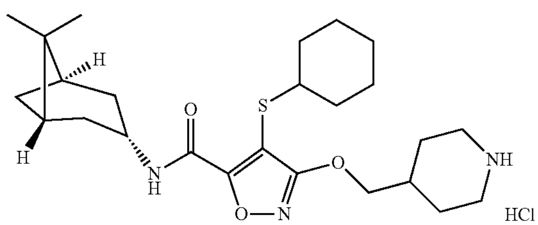 [SMILES: CC1(C)[C@@H]2C[C@@H](NC(=O)c3onc(OCC4CCNCC4)c3SC3CCCCC3)C[C@H]1C2 ; Cl] | (DMSO-d6); 1.03 (s, 3H), 1.04 (d, J = 7.2 Hz, 3H), 1.22 (s, 3H), 1.13-2.43 (m, 25H), 2.80-3.00 (m, 2H) 3.20 (m, 1H), 3.29 (bs, 1H), 4.18 (d, J = 6.3 Hz, 2H) 4.22-4.31 (m, 1H), 8.56 (bs, 1H), 8.79 (d, J = 8.4 Hz, 1H), 8.86 (bs, 1H) |
| C-17 | 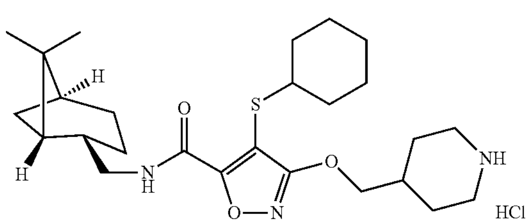 [SMILES: CC1(C)[C@H]2CC[C@H](CNC(=O)c3onc(OCC4CCNCC4)c3SC3CCCCC3)[C@@H]1C2 ; Cl] | (DMSO-d6); 1.04 (s, 3H), 1.17 (s, 3H), 1.19-2.36 (m, 25H), 2.82-3.00 (m, 2H) 3.19-3.39 (m, 4H), 4.18 (d, J = 6.3 Hz, 2H), 8.58 (bs, 1H), 8.72 (t, J = 6.0 Hz, 1H), 8.90 (bs, 1H) |
| C-18 | 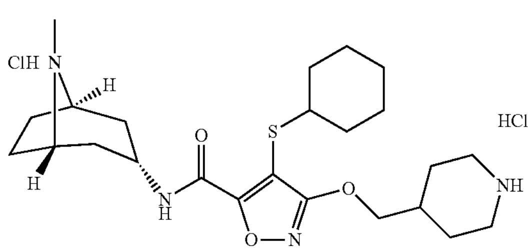 | (CDCl3); 1.74 (s, 3H), 1.19-3.96 (m, 30H) 4.24 (bs, 2H), 4.53 (m, 1H), 8.05 (d, J = 8.7 Hz, 1H), 9.54 (bs, 1H) 9.81 (bs, 1H), 12.15 (bs, 1H) |

TABLE 33

| No. | Structure | NMR (CDCl3 or d6-DMSO) |
| --- | --- | --- |
| C-19 | 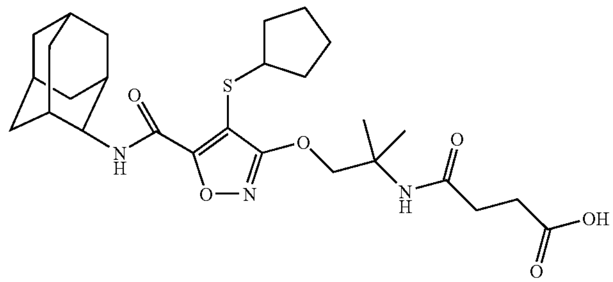 [SMILES: CC(C)(COc1noc(C(=O)NC2C3CC4CC(C3)CC2C4)c1SC1CCCC1)NC(=O)CCC(=O)O] | (CDCl3); 1.27 (s, 6H), 1.26-2.02 (m, 20H), 2.49 (m, 2H) 2.67 (m, 2H), 3.56-3.59 (m, 1H) 4.44 (s, 2H), 4.27 (d, J = 6.0 Hz, 1H), 5.98 (s, 1H), 8.09 (d, J = 9.0 Hz, 1H), |
| C-20 | 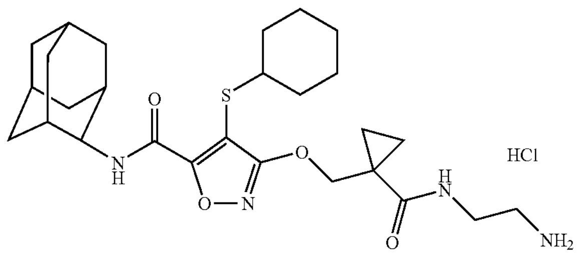 [SMILES: NCCNC(=O)C1(COc2noc(C(=O)NC3C4CC5CC(C4)CC3C5)c2SC2CCCCC2)CC1 ; Cl] | (DMSO-d6) 0.93-0.96 (m, 2H), 1.23-1.97 (m, 26H), 2.84 (s, 2H), 3.12 (m, 1H), 3.35 (d, J = 4.5 Hz, 2H), 4.04 (d, J = 7.5 Hz, 1H), 4.45 (s, 2H), 8.00 (t, J = 5.4 Hz, 1H), 8.11 (br, 3H), 8.40 (d, J = 7.5 Hz, 1H) |
| C-21 | 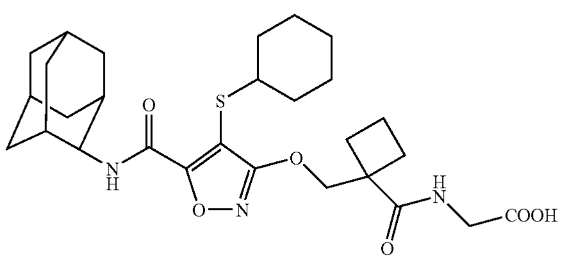 [SMILES: O=C(O)CNC(=O)C1(COc2noc(C(=O)NC3C4CC5CC(C4)CC3C5)c2SC2CCCCC2)CCC1] | (CDCl3) 1.19-1.35 (m, 4H), 1.62-2.10 (m, 24H), 2.52 (m, 2H), 3.09 (m, 1H), 4.10 (d, J = 4.5 Hz, 2H), 4.27 (d, J = 8.1 Hz, 1H), 4.60 (s, 2H), 6.60 (m, 1H), 8.18 (d, J = 8.1 Hz, 1H) |
| C-22 | 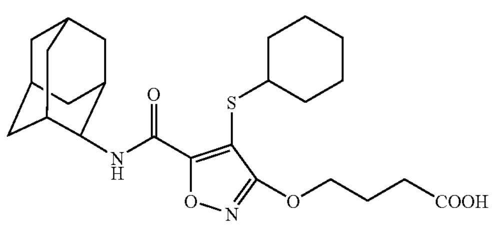 [SMILES: O=C(O)CCCOc1noc(C(=O)NC2C3CC4CC(C3)CC2C4)c1SC1CCCCC1] | (CDCl3) 1.19-2.02 (m, 24H), 2.14-2.23 (m, 2H), 2.57 (t, J = 7.5 Hz, 2H), 2.09-3.16 (m, 1H), 4.28 (d, J = 8.1 Hz, 1H), 4.41 (t, J = 6.0 Hz, 2H), 8.13 (d, J = 8.1 Hz, 1H) |
| C-23 | 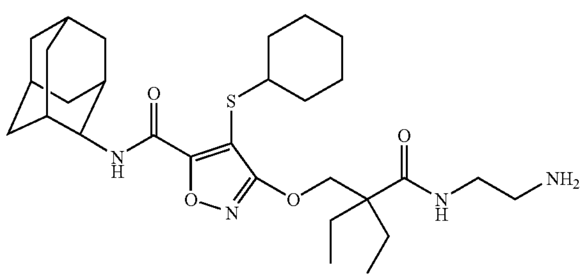 [SMILES: CCC(CC)(COc1noc(C(=O)NC2C3CC4CC(C3)CC2C4)c1SC1CCCCC1)C(=O)NCCN] | (CDCl3) 0.87-0.92 (m, 6H), 1.26-1.36 (m, 6H), 1.63-2.01 (m, 22H), 2.89 (m, 2H), 3.10 (m, 1H), 3.38 (m, 2H), 4.26 (m, 1H), 4.45 (s, 2H), 8.09 (d, J = 8.4 Hz, 1H) |
| C-24 | 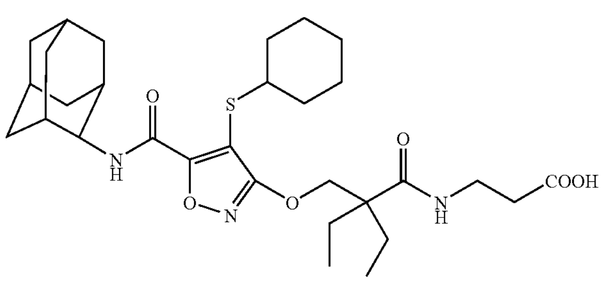 [SMILES: CCC(CC)(COc1noc(C(=O)NC2C3CC4CC(C3)CC2C4)c1SC1CCCCC1)C(=O)NCCC(=O)O] | (CDCl3) 0.88 (t, J = 7.2 Hz, 6H), 1.19-2.01 (m, 28H), 2.61 (t, J = 4.8 Hz, 2H), 3.08 (m, 1H), 3.56 (m, 2H), 4.27 (d, J = 7.8 Hz, 1H), 4.42 (s, 2H), 6.66 (m, 1H), 8.16 (d, J = 7.8 Hz, 1H) |

TABLE 34
| No. | Structure | NMR (CDCl3 or d6-DMSO) |
|---|---|---|
| C-25 | 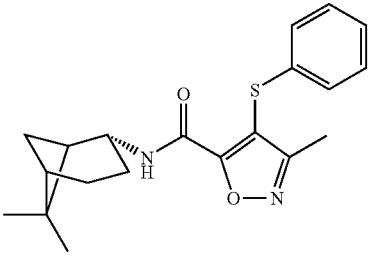 [SMILES: Cc1noc(C(=O)N[C@@H]2CCC3CC2C3(C)C)c1Sc1ccccc1] | (DMSO-d6); 0.97-1.02 (m, 4H), 1.12 (s, 3H), 1.68-1.80 (m, 2H), 1.87-1.93 (m, 2H), 2.09 (s, 4H), 2.18-2.31 (m, 2H), 4.30-4.35 (brm, 1H), 7.19-7.36 (m, 5H), 8.49 (d, J = 6.0 Hz, 1H) |
| C-26 | 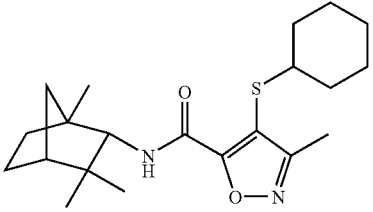 [SMILES: Cc1noc(C(=O)NC2C3(C)CCC(C3)C2(C)C)c1SC1CCCCC1] | (DMSO-d6); 0.81 (s, 3H), 1.03-1.85 (m, 23H), 2.31 (s, 3H), 3.03 (brs, 1H), 3.68 (d, J = 9.2 Hz, 1H), 8.11 (d, J = 9.6 Hz, 1H) |
| C-27 | 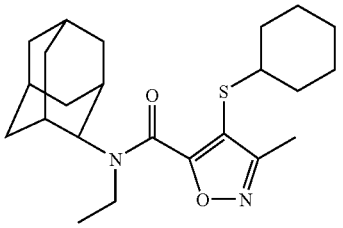 [SMILES: CCN(C(=O)c1onc(C)c1SC1CCCCC1)C1C2CC3CC(C2)CC1C3] | (DMSO-d6); 1.07-2.01 (m, 26H), 2.29 (brs 4H), 2.95 (brs, 1H), 3.40 (brs, 2H), 4.02 (brs, 1H) |
| C-28 | 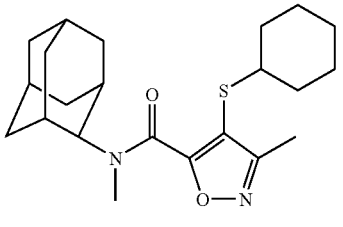 | (CDCl3); 1.21-2.09 (m, 23H), 2.28 (brs, 1H), 2.33 (s, 3H), 2.92-3.00 (m, 1H), 3.10 (brs, 2H), 4.38 (brs, 1H) |
| C-29 | 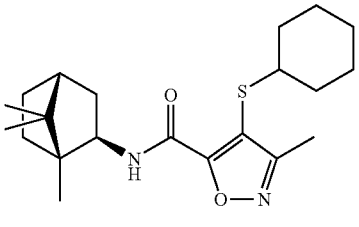 [SMILES: Cc1noc(C(=O)N[C@@H]2C[C@H]3CC[C@]2(C)C3(C)C)c1SC1CCCCC1] | (DMSO-d6); 0.82 (s, 3H), 0.86 (s, 3H), 0.97 (s, 3H), 1.10-1.26 (m, 7H), 1.50-1.60 (m, 2H), 1.63-1.82 (m, 8H), 2.29 (s, 3H), 3.05 (brs, 1H), 3.91-3.97 (m, 1H), 8.04 (d, J = 8.0 Hz, 1H) |
| C-30 | 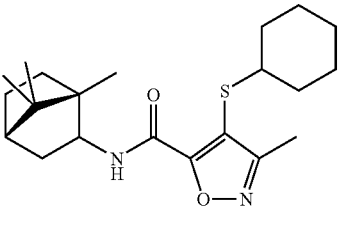 [SMILES: Cc1noc(C(=O)NC2C[C@@H]3CC[C@@]2(C)C3(C)C)c1SC1CCCCC1] | (DMSO-d6); 0.82 (s, 3H), 0.86 (s, 3H), 0.97 (s, 3H), 1.10-1.26 (m, 7H), 1.50-1.60 (m, 2H), 1.63-1.82 (m, 8H), 2.29 (s, 3H), 3.05 (brs, 1H), 3.91-3.97 (m, 1H), 8.04 (d, J = 8.0 Hz, 1H) |

TABLE 35
| No. | Structure | NMR (CDCl3 or d6-DMSO) |
|---|---|---|
| C-31 | 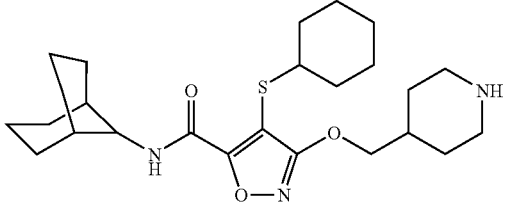 [SMILES: O=C(NC1C2CCCC1CCC2)c1onc(OCC2CCNCC2)c1SC1CCCCC1] | (DMSO-d6); 1.09-1.89 (m, 29H), 2.43-2.50 (m, 2H), 2.94 (d, J = 8.4 Hz, 2H), 3.13 (brm, 1H), 3.86 (d, J = 6.4 Hz, 1H), 4.12 (d, J = 6.4 Hz, 2H), 8.35 (d, J = 6.8 Hz, 1H) |
| C-32 | 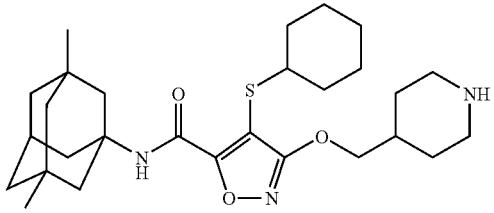 | (DMSO-d6), 0.84 (s, 6H), 1.14-2.12 (m, 28H), 2.12 (brs, 2H), 2.86-2.93 (m, 2H), 3.11 (brs, 1H), 3.27-3.32 (m, 2H), 4.16 (d, J = 6.4 Hz, 2H), 8.03 (s, 1H), 8.76 (brs, 1H), 9.06 (brs, 1H) |
| C-33 | 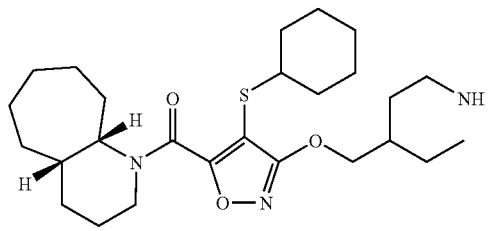 [SMILES: CCC(CCN)COc1noc(C(=O)N2CCC[C@@H]3CCCCC[C@@H]32)c1SC1CCCCC1] | (DMSO-d6); 1.10-2.00 (m, 30H), 2.43-2.50 (m, 2H), 2.68 (t, J = 12.0 Hz, 0.5H), 2.95 (d, J = 12.0 Hz, 2H), 3.00-3.03 (m, 1H), 3.22 (d, J = 14.0 Hz, 0.5H), 3.34-3.57 (m, 0.5H), 4.08-4.14 (m, 2.5H), 4.29 (d, J = 14.0 Hz, 0.5H), 4.53-4.58 (m, 0.5H) |
| C-34 | 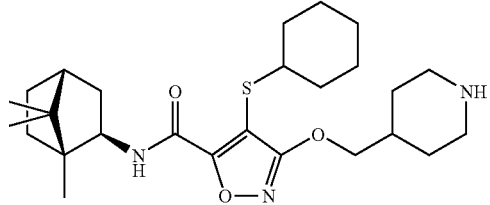 | (DMSO-d6); 0.81 (s, 3H), 0.85 (s, 3H), 0.97 (s, 3H), 1.17-1.39 (m, 8H), 1.48-1.88 (m, 14H), 2.15 (brs, 1H), 2.86-2.91 (m, 2H), 3.13 (brs, 1H), 3.89-3.94 (d, J = 6.4 Hz, 2H), 7.98 (d, J = 8.4 Hz, 1H), 8.95 (brs, 1H), 9.21 (brs, 1H) |
| C-35 | 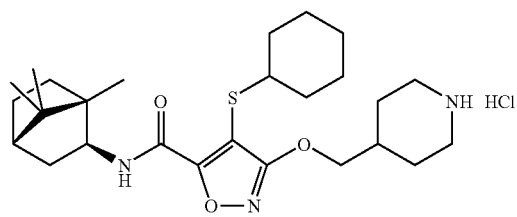 [SMILES: CC1(C)[C@H]2CC[C@]1(C)[C@@H](NC(=O)c1onc(OCC3CCNCC3)c1SC1CCCCC1)C2 ; Cl] | (DMSO-d6); 0.81 (s, 3H), 0.85 (s, 3H), 0.97 (s, 3H), 1.17-1.39 (m, 8H), 1.48-1.88 (m, 14H), 2.15 (brs, 1H), 2.86-2.91 (m, 2H), 3.13 (brs, 1H), 3.89-3.94 (d, J = 6.4 Hz, 2H), 7.98 (d, J = 8.4 Hz, 1H), 8.95 (brs, 1H), 9.21 (brs, 1H) |
| C-36 | 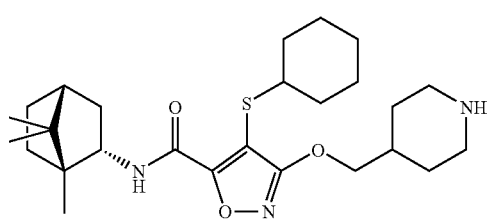 | (DMSO-d6); 0.78 (s, 3H), 0.86 (s, 3H), 0.93 (s, 3H), 1.10-1.89 (m, 20H), 2.12-2.21 (brm, 2H), 2.86-2.93 (brm, 2H), 3.12 (brm, 1H), 3.27-3.32 (m, 2H), 4.18 (d, J = 6.4 Hz, 2H), 4.25 (brs, 1H), 8.52 (d, J = 8.8 Hz, 1H), 8.84 (brs, 1H), 9.13 (brs, 1H) |

TABLE 36

| No. | Structure | NMR (CDCl3 or d6-DMSO) |
|---|---|---|
| C-37 | 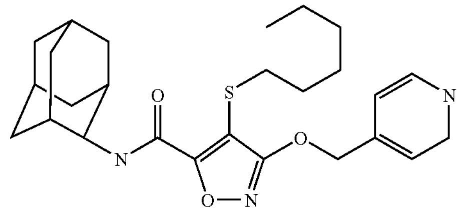 [SMILES: CCCCCCSc1c(OCC2=CCNC=C2)noc1C(=O)NC1C2CC3CC(C2)CC1C3] | (DMSO-d6); 1.11-1.34 (m, 5H), 1.50-2.00 (m, 19H), 3.14 (brs, 1H), 4.03 (brs, 1H), 5.44 (s, 2H), 7.45 (d, J = 5.2 Hz, 2H), 8.45 (d, J = 6.8 Hz, 1H), 8.62 (d, J = 4.8 Hz, 2H) |
| C-38 | 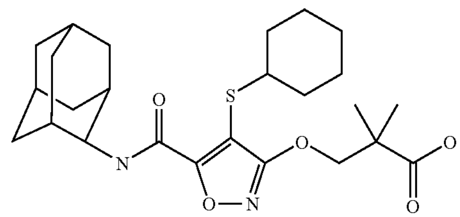 [SMILES: CC(C)(COc1noc(C(=O)NC2C3CC4CC(C3)CC2C4)c1SC1CCCCC1)C(=O)O] | (DMSO-d6); 1.23 (brs, 11H), 1.50-1.99 (m, 19H), 3.12 (brs, 1H), 4.04 (brs, 1H), 4.28 (s, 2H), 8.39 (d, J = 6.8 Hz, 1H), 12.50 (s, 1H) |
| C-39 | 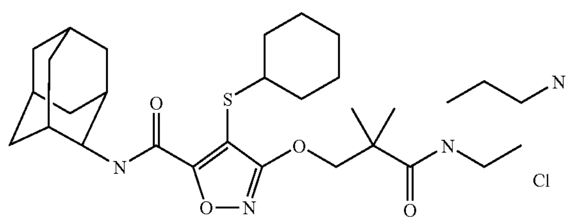 | (DMSO-d6); 1.15-1.99 (m, 34H), 2.89 (t, J = 12.4 Hz, 2H), 3.11 (brs, 1H), 3.34 (brs, 1H), 4.03 (brs, 1H), 4.30 (s, 4H), 8.23 (brs, 3H), 8.40 (d, J = 7.6 Hz, 1H) |
| C-40 | 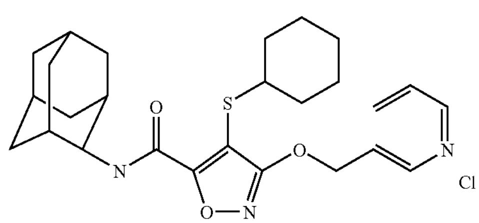 [SMILES: C=C/C=N\C=C\COc1noc(C(=O)NC2C3CC4CC(C3)CC2C4)c1SC1CCCCC1 ; Cl] | (DMSO-d6); 1.18-1.26 (m, 5H), 1.49-2.00 (m, 19H), 3.11 (brs, 1H), 4.03 (brs, 1H), 5.57 (s, 2H), 8.01 (dd, J = 5.6, 7.8 Hz, 1H), 8.45 (d, J = 6.8 Hz, 1H), 8.52 (d, J = 7.8 Hz, 1H), 8.88 (d, J = 5.2 Hz, 1H), 8.99 (s, 1H) |
| C-41 | 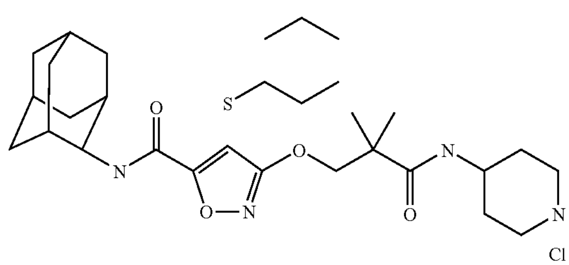 | (DMSO-d6); 1.21-1.27 (m, 11H), 1.51-1.99 (m, 23H), 2.89-2.96 (brm, 2H), 3.10 (brs, 1H), 3.25 (d, J = 12.4 Hz, 2H), 3.85 (brs, 1H), 4.03 (brs, 1H), 4.30 (s, 2H), 7.72 (d, J = 7.6 Hz, 1H), 8.39 (d, J = 7.2 Hz, 1H), 8.88 (brs, 2H) |
| C-42 | 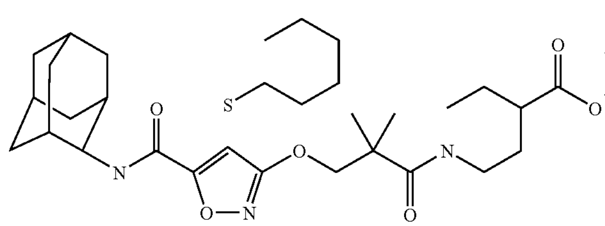 | (DMSO-d6); 1.15-1.99 (m, 34H), 2.95 (t, J = 11.7 Hz, 2H), 3.10 (brs, 1H), 4.03 (d, J = 7.2 Hz, 1H), 4.16 (d, J = 13.8 Hz, 2H), 4.30 (s, 2H), 8.40 (d, J = 7.2 Hz, 1H) |

TABLE 37

| No. | Structure | NMR (CDCl3 or d6-DMSO) |
|---|---|---|
| C-43 | 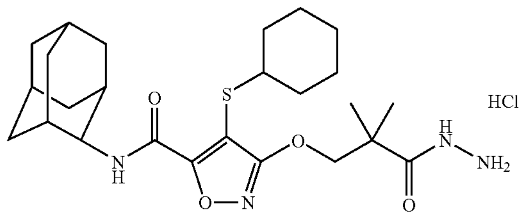 [SMILES: CC(C)(COc1noc(C(=O)NC2C3CC4CC(C3)CC2C4)c1SC1CCCCC1)C(=O)NN ; Cl] | (DMSO-d6); 1.20-1.30 (m, 11H), 1.52-2.00 (m, 19H), 3.10 (brs, 1H), 4.03 (d, J = 6.9 Hz, 1H), 4.35 (s, 2H), 8.41 (d, J = 7.2 Hz, 1H), 10.10 (brs, 3H), 11.00 (s, 1H) |
| C-44 | 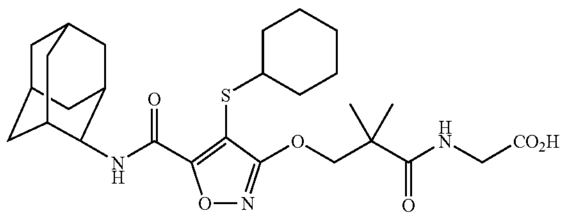 [SMILES: CC(C)(COc1noc(C(=O)NC2C3CC4CC(C3)CC2C4)c1SC1CCCCC1)C(=O)NCC(=O)O] | (DMSO-d6); 1.24 (brs, 11H), 1.46-1.99 (m, 19H), 3.10 (brs, 1H), 3.73 (d, J = 5.2 Hz, 2H), 4.03 (brs, 1H), 4.28 (s, 2H), 8.03 (t, J = 5.2 Hz, 1H), 8.38 (d, J = 7.2 Hz, 1H), 12.51 (brs, 1H) |
| C-45 | 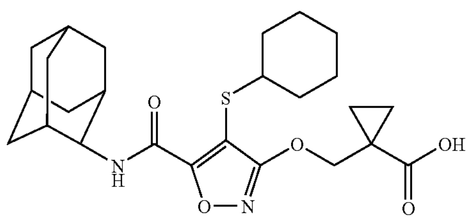 [SMILES: O=C(NC1C2CC3CC(C2)CC1C3)c1onc(OCC2(C(=O)O)CC2)c1SC1CCCCC1] | (DMSO-d6); 1.07-1.10 (m, 2H), 1.14-1.31 (m, 5H), 1.50-1.99 (m, 21H), 3.14 (brs, 1H), 4.04 (d, J = 6.0 Hz, 1H), 4.37 (s, 2H), 8.39 (d, J = 7.2 Hz, 1H), 12.48 (s, 1H) |
| C-46 | 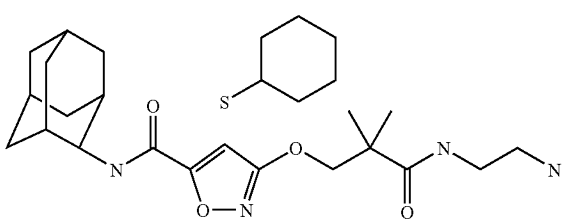 | (DMSO-d6); 1.11-1.27 (m, 11H), 1.50-1.99 (m, 19H), 2.56 (t, J = 6.4 Hz, 2H), 3.04-3.09 (m, 3H), 4.03 (brs, 1H), 4.27 (s, 2H), 7.63 (brs, 1H), 8.39 (d, J = 7.2 Hz, 1H) |
| C-47 | 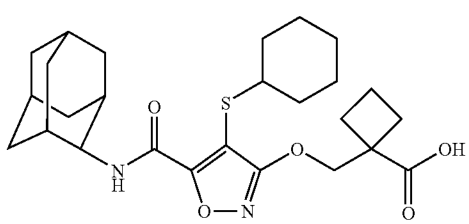 [SMILES: O=C(NC1C2CC3CC(C2)CC1C3)c1onc(OCC2(C(=O)O)CCC2)c1SC1CCCCC1] | (DMSO-d6); 1.08-1.28 (m, 5H), 1.50-2.09 (m, 23H), 2.37-2.43 (m, 2H), 3.10 (brs, 1H), 4.04 (d, J = 6.8 Hz, 1H), 4.52 (s, 2H), 8.38 (s, J = 7.2 Hz, 1H), 12.55 (s, 1H) |
| C-48 | 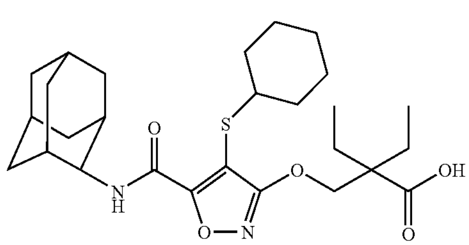 [SMILES: CCC(CC)(COc1noc(C(=O)NC2C3CC4CC(C3)CC2C4)c1SC1CCCCC1)C(=O)O] | (DMSO-d6); 0.82 (t, J = 7.2 Hz, 6H), 1.11-1.27 (m, 5H), 1.51-2.00 (m, 23H), 3.08 (brs, 1H), 4.04 (d, J = 7.2 Hz, 1H), 4.33 (s, 2H), 8.40 (d, J = 7.2 Hz, 1H), 12.66 (s, 1H) |

TABLE 38
| No. | Structure | NMR (CDCl3 or d6-DMSO) |
|---|---|---|
| C-49 | 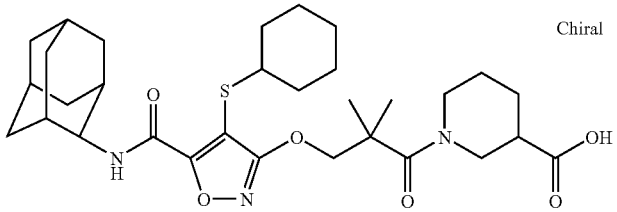 [SMILES: CC(C)(COc1noc(C(=O)NC2C3CC4CC(C3)CC2C4)c1SC1CCCCC1)C(=O)N1CCCC(C(=O)O)C1] Chiral | (DMSO-d6); 1.16-1.99 (m, 34H), 2.27-2.33 (m, 1H), 2.83-2.89 (m, 2H), 3.12 (brs, 1H), 4.02-4.05 (brm, 1H), 4.16 (d, J = 12.8 Hz, 1H), 4.31 (s, 2H), 4.37 (d, J = 12.8 Hz, 1H), 8.38 (d, J = 7.2 Hz, 1H), 12.39 (s, 1H) |
| C-50 | 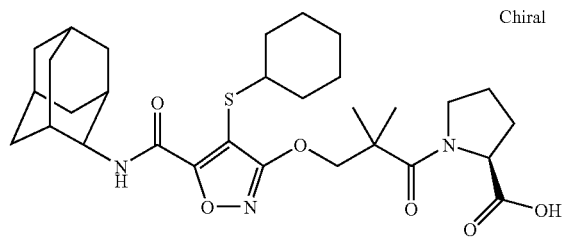 [SMILES: CC(C)(COc1noc(C(=O)NC2C3CC4CC(C3)CC2C4)c1SC1CCCCC1)C(=O)N1CCC[C@H]1C(=O)O] Chiral | (DMSO-d6); 1.16- 2.04 (m, 34H), 3.11 (brs, 1H), 3.67 (brs, 1H), 3.74 (brs, 1 H), 4.02-4.04 (m, 1H), 4.27 (d, J = 8.8 Hz, 2H), 4.36 (d, J = 10.0 Hz, 1H), 8.40 (d, J = 7.8 Hz, 1H), 12.25 (s, 1H) |
| C-51 | 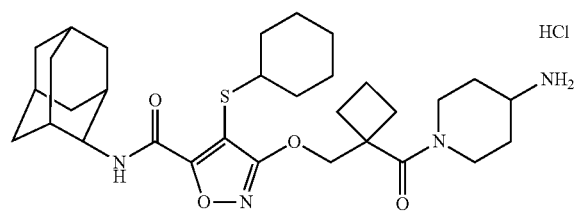 [SMILES: NC1CCN(C(=O)C2(COc3noc(C(=O)NC4C5CC6CC(C5)CC4C6)c3SC3CCCCC3)CCC2)CC1 ; Cl] HCl | (DMSO-d6); 1.21-2.06 (m, 32H), 2.14 (brs, 2H), 2.42-2.47 (m, 2H), 2.62 (brs, 1H), 3.13 (brs, 2H), 3.24 (brs, 1H), 3.70 (brs, 1H), 4.03 (brs, 1H), 4.34 (brs, 1H), 4.50 (brs, 1H), 8.25 (brs, 3H), 8.42 (d, J = 7.2 Hz, 1H) |
| C-52 | 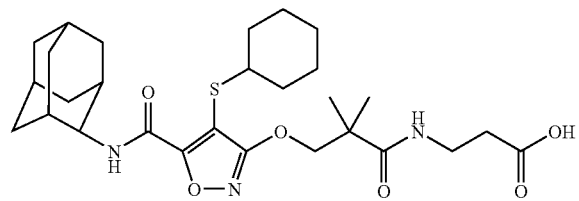 [SMILES: CC(C)(COc1noc(C(=O)NC2C3CC4CC(C3)CC2C4)c1SC1CCCCC1)C(=O)NCCC(=O)O] | (DMSO-d6); 1.19-1.27 (m, 11H), 1.50-1.99 (m, 19H), 2.39 (t, J = 7.2 Hz, 2H), 3.10 (brs, 2H), 3.25-3.30 (m, 2H), 4.03 (brs, 1H), 4.25 (s, 2H), 7.77 (t, J = 5.6 Hz, 1H), 8.39 (d, J = 7.2 Hz, 1H), 12.17 (s, 1H) |
| C-53 | 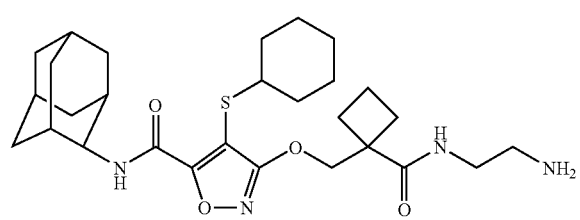 [SMILES: NCCNC(=O)C1(COc2noc(C(=O)NC3C4CC5CC(C4)CC3C5)c2SC2CCCCC2)CCC1] | (DMSO-d6); 1.11-2.03 (m, 28H), 2.33-2.40 (m, 2H), 2.58 (t, J = 6.4 Hz, 2H), 3.07-3.12 (m, 3H), 4.03 (brs, 1H), 4.51 (s, 2H), 7.73 (t, J = 5.6 Hz, 1H), 8.40 (d, J = 7.2 Hz, 1H) |
| C-54 | 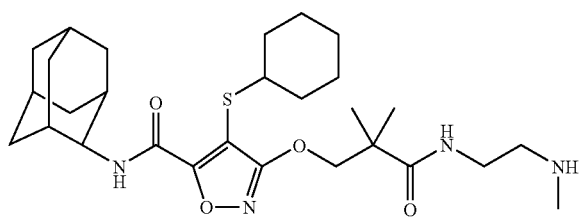 [SMILES: CNCCNC(=O)C(C)(C)COc1noc(C(=O)NC2C3CC4CC(C3)CC2C4)c1SC1CCCCC1] | (DMSO-d6); 1.20-1.30 (m, 11H), 1.44-1.99 (19H), 2.25 (s, 3H), 2.50 (m, 2H), 3.05-3.14 (m, 3H), 4.03 (s, 1H), 4.26 (s, 2H), 7.62 (brs, 1H), 8.39 (d, J = 7.2 Hz, 1H) |

TABLE 39

| No. | Structure | NMR (CDCl3 or d6-DMSO) |
|---|---|---|
| C-55 | Chiral | (DMSO-d6); 1.16-2.04 (m, 34H), 3.11 (brs, 1H), 3.67 (brs, 1H), 3.74 (brs, 1H), 4.02-4.04 (m, 1H), 4.27 (d, J = 8.8 Hz, 2H), 4.36 (d, J = 10.0 Hz, 1H), 8.40 (d, J = 7.8 Hz, 1H), 12.25 (s, 1H) |
| C-56 | Chiral | (DMSO-d6); 1.19-1.99 (m, 32H), 2.53-2.57 (m, 1H), 2.65-2.72 (m, 1H), 2.85-2.93 (m, 1H), 3.11 (s, 1H), 4.03 (brs, 1H), 4.13 (brs, 1H), 4.28 (s, 2H), 7.57 (d, J = 6.4 Hz, 1H), 8.38 (d, J = 6.8 Hz, 1H) |
| C-57 | Chiral | (DMSO-d6); 1.20-2.00 (m, 32H), 3.10 (brs, 1H), 3.28-3.70 (brm, 5H), 4.03-4.05 (brm, 1H), 4.32 (s, 2H), 8.40 (d, J = 7.2 Hz, 1H) |
| C-58 | Chiral | (DMSO-d6); 1.20-1.99 (m, 34H), 2.68-2.82 (m, 2H), 2.99-3.12 (m, 3H), 4.03 (brs, 1H), 4.27 (s, 2H), 7.65 (t, J = 5.6 Hz, 1H), 8.38 (d, J = 7.2 Hz, 1H) |
| C-59 | 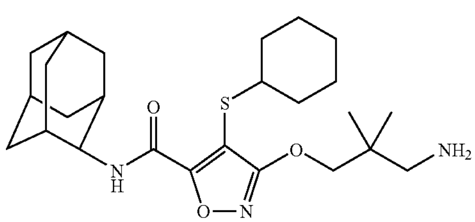 [SMILES: CC(C)(CN)COc1noc(C(=O)NC2C3CC4CC(C3)CC2C4)c1SC1CCCCC1] | (DMSO-d6); 0.96 (s, 6H), 1.21-1.99 (m, 24H), 2.49 (s, 2H), 3.13 (brs, 1H), 4.05 (s, 3H), 8.38 (d, J = 7.2 Hz, 1H) |
| C-60 | 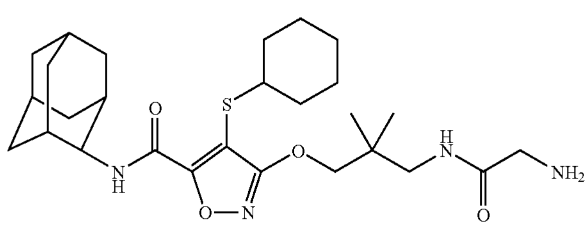 [SMILES: CC(C)(CNC(=O)CN)COc1noc(C(=O)NC2C3CC4CC(C3)CC2C4)c1SC1CCCCC1] | (DMSO-d6); 0.96 (s, 6H), 1.19-1.99 (m, 24H), 3.10-3.20 (brm, 5H), 4.00 (s, 2H), 4.04 (s, 1H), 7.82 (brs, 1H), 8.41 (d, J = 7.2 Hz, 1H) |

TABLE 40

| No. | Structure | NMR (CDCl3 or d6-DMSO) |
|---|---|---|
| C-61 | 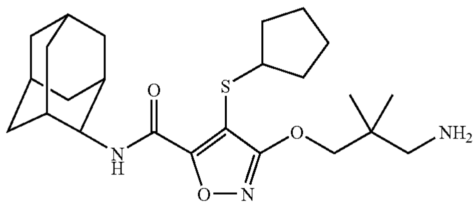 [SMILES: CC(C)(CN)COc1noc(C(=O)NC2C3CC4CC(C3)CC2C4)c1SC1CCCC1] | (DMSO-d6); 0.92 (s, 6H), 1.45-1.99 (m, 22H), 2.49 (s, 2H), 3.55-3.61 (m, 1H), 4.05 (s, 3H), 8.39 (d, J = 7.2 Hz, 1H) |
| C-62 | 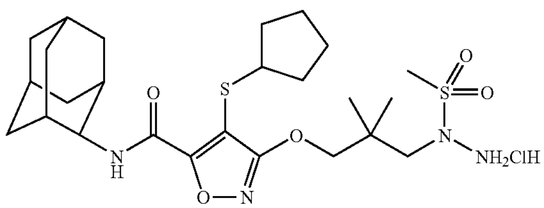 | (DMSO-d6); 1.05 (s, 6H), 1.45-1.99 (m, 22H), 3.00 (s, 3H), 3.08 (brs, 2H), 3.17 (s, 2H), 3.44 (t, = 7.6 Hz, 2H), 3.60-3.65 (m, 1H), 4.07 (s, 3H), 8.14 (brs, 3H), 8.41 d, J = 6.8 Hz, 1H) |
| C-63 | 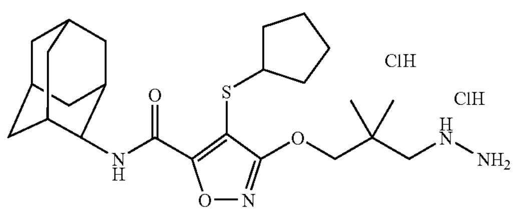 [SMILES: CC(C)(CNN)COc1noc(C(=O)NC2C3CC4CC(C3)CC2C4)c1SC1CCCC1 ; Cl ; Cl] | (DMSO-d6); 1.18 (s, 6H), 1.47-1.99 (m, 22H), 3.01 (brs, 2H), 3.26 (brs, 2H), 3.30 (brs, 2H), 3.60 (t, J = 6.0 Hz, 1H), 4.04 (brs, 1H), 4.20 (s, 2H), 8.43 (d, J = 7.2 Hz, 1H), 8.50 (brs, 3H), 9.32 (brs, 2H) |
| C-64 | 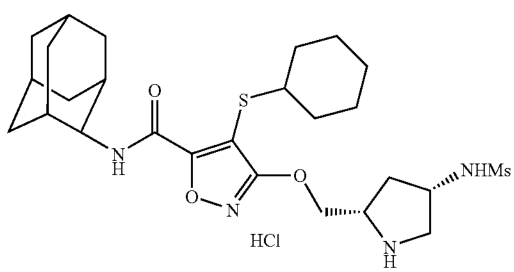 | (DMSO-d6) 1.08-2.03 (m, 26H), 3.01 (s, 3H), 3.08-3.52 (m, 2H), 3.97-4.13 (m, 3H), 4.48-4.66 (m, 2H), 7.50-7.71 (m, 4H), 8.46 (d, J = 7.2 Hz, 1H) |
| C-65 | 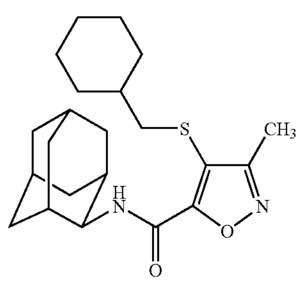 [SMILES: Cc1noc(C(=O)NC2C3CC4CC(C3)CC2C4)c1SCC1CCCCC1] | (DMSO-d6); 0.93 (m, 2H), 1.11 (m, 3H), 1.30 (m, 1H), 1.5-2.1 (m, 20H), 2.31 (s, 3H), 2.67 (d, J = 5.1 Hz, 2H), 4.03 (m, 1H), 8.49 (d, J = 5.1 Hz, 1H) |
| C-66 | 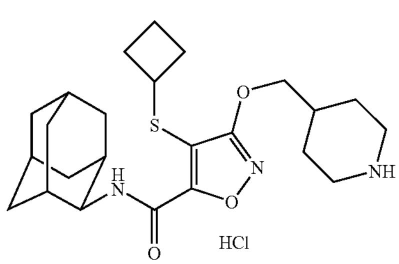 [SMILES: O=C(NC1C2CC3CC(C2)CC1C3)c1onc(OCC2CCNCC2)c1SC1CCC1 ; Cl] | (DMSO-d6); 1.50 (m, 1H), 1.97 (m, 1H), 1.47-2.04 (m, 18H), 2.13 (brs, 2H, 2.22 (m, 2H), 2.90 (m, 2H), 3.28 (d, J = 10.2 Hz, 2H), 4.03 (brs, 1H), 4.19 (d, J = 4.2 Hz, 2H), 8.40 (m, 1H), 8.84 (m, 1H), 9.14 (m, 1H) |

TABLE 41

| No. | Structure | NMR (CDCl3 or d6-DMSO) |
|---|---|---|
| C-67 | 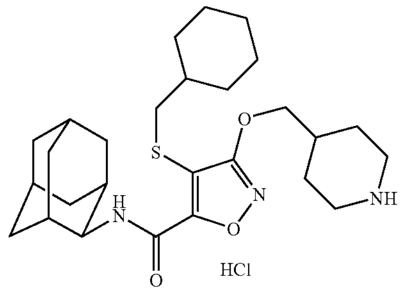 [SMILES: O=C(NC1C2CC3CC(C2)CC1C3)c1onc(OCC2CCNCC2)c1SCC1CCCCC1 ; Cl] | (DMSO-d6); 0.92 (m, 2H), 1.22 (m, 3H), 1.31 (m, 1H, 1.42-2.04 (m, 18H), 2.14 (brs, 1H), 2.72 (d, J = 5.4 Hz, 2H), 2.90 (m, 2H), 3.29 (d, J = 8.7 Hz, 2H), 4.02 (brs, 1H), 4.19 (d = 4.5 Hz, 2H) 8.38 (d, J = 5.1 Hz, 1H), 8.73 (m, 1H), 9.05 (m, 1H) |
| C-68 | 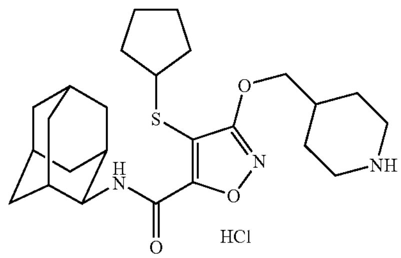 [SMILES: O=C(NC1C2CC3CC(C2)CC1C3)c1onc(OCC2CCNCC2)c1SC1CCCC1 ; Cl] | (DMSO-d6); 0.92 (m, 2H), 1.12 (m, 3H), 1.32 (m, 1H), 1.5-2.04 (m, 23H), 2.15 (brs, 1H), 2.12 (d, J = 5.1 Hz, 2H), 2.90 (m, 2H), 4.02 (brs, 1H), 4.19 (d, J = 4.8 Hz, 2H), 8.39 (d, J = 5.4 Hz, 1H), 8.74 (brs, 1H), 9.03 (brs, 1H) |
| C-69 | 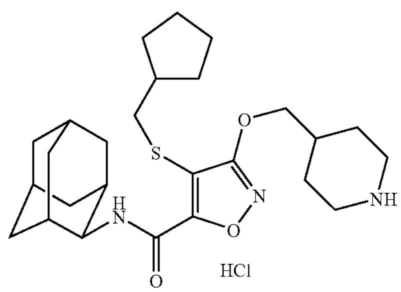 [SMILES: O=C(NC1C2CC3CC(C2)CC1C3)c1onc(OCC2CCNCC2)c1SCC1CCCC1 ; Cl] | (DMSO-d6); 1.41-2.04 (m, 23H), 2.16 (brs, 1H), 2.90 (m, 2H), 3.28 (d, J = 8.7 Hz, 2H), 3.58 (m, 1H), 4.03 (brs, 1H), 4.19 (d, J = 4.5 Hz, 2H), 8.41 (d, J = 5.7 Hz, 1H), 8.83 (brs, 1H), 9.11 (brs, 1H) |
| C-70 | 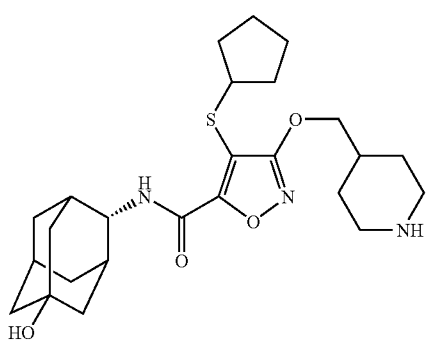 | (DMSO-d6); 1.17 (m, 2H), 1.35-2.1 (m, 18H), 2.46 (t, J = 7.5 Hz, 2H), 2.95 (d, J = 8.7 Hz, 2H), 3.56 (m, 1H), 3.94 (brs, 1H), 4.11 (d, J = 4.8 Hz, 2H), 4.47 (brs, 1H), 8.36 (d, J = 5.1 Hz, 1H) |
| C-71 | 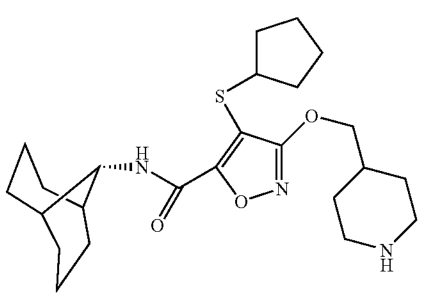 | (DMSO-d6); 1.4-1.9 (m, 32H), 2.11 (brs, 1H), 2.86 (brt, J = 8.4 Hz, 2H) 3.2-3.4 (m, 8H) 3.75 (m, 1H), 3.86 (m, 1H), 4.19 (d, J = 4.5 Hz, 2H), 8.36 (d, J = 5.1 Hz, 1H) |

TABLE 41-continued

| No. | Structure | NMR (CDCl3 or d6-DMSO) |
|---|---|---|
| C-72 | 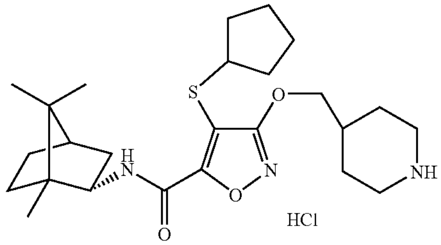 [SMILES: CC1(C)C2CCC1(C)[C@@H](NC(=O)c1onc(OCC3CCNCC3)c1SC1CCCC1)C2 ; Cl] | (DMSO-d6); 0.79 (m, 1H), 0.81 (s, 3H), 0.84 (s, 3H), 0.96 (s, 5H), 1.90 (m, 2H), 1.4-1.95 (m, 14H), 2.15 (brs, 1H), 2.89 (m, 2H), 3.30 (d, J = 10 Hz, 2H), 3.91 (m, 1H), 4.18 (d, J = 4.5 Hz, 2H), 7.97 (d, J = 6.0 Hz, 1H), 8.82 (brs, 1H), 9.09 (brs, 1H) |

TABLE 42

| No. | Structure | NMR (CDCl3 or d6-DMSO) |
|---|---|---|
| C-73 | 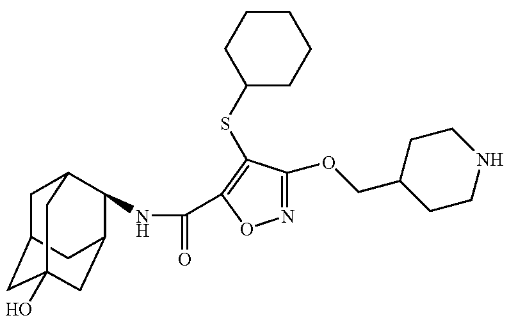 | (DMSO-d6); 1.16 (m, 2H), 1.4-2.05 (m, 11H), 2.12 (brs, 2H), 2.47 (t, J = 9.0 Hz, 2H), 2.95 (d, J = 9.0 Hz, 2H), 3.56 (m, 1H), 3.87 (m, 1H), 4.11 (d, J = 4.8 Hz, 2H), 4.45 (brs, 1H), 8.37 (d, J = 5.1 Hz, 1H) |
| C-74 | 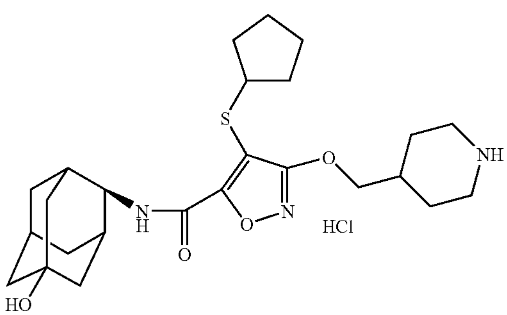 | (DMSO-d6); 1.07-2.3 (m, 25H), 2.87 (brs, 2H), 3.10 (brs, 2H), 3.85 (m, 1H), 4.15 (m, 2H), 4.46 (brs, 1H), 8.35 (brs, 1H), 8.94 (m, 1H), 9.19 (m, 1H) |
| C-75 | 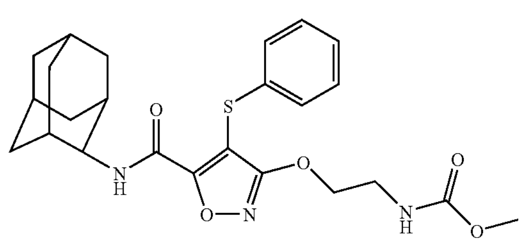 [SMILES: COC(=O)NCCOc1noc(C(=O)NC2C3CC4CC(C3)CC2C4)c1Sc1ccccc1] | (DMSO-d6); 1.48-1.89 (m, 14H), 3.02-3.13 (m, 1H), 3.51 (s, 3H), 4.00-4.04 (m, 1H), 4.21-4.30 (m, 2H), 4.62-4.78 (m, 1H), 7.20-7.35 (m, 6H), 8.49 (d, J = 7.2 Hz, 1H) |
| C-76 | 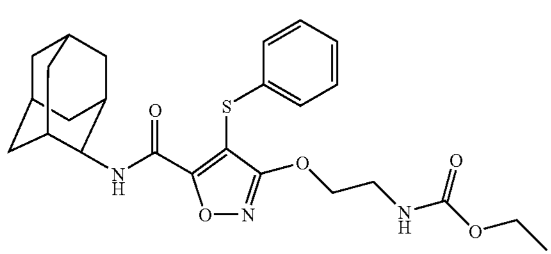 [SMILES: CCOC(=O)NCCOc1noc(C(=O)NC2C3CC4CC(C3)CC2C4)c1Sc1ccccc1] | (DMSO-d6); 1.11-1.16 (m, 3H), 1.48-1.89 (m, 14H), 3.93-4.06 (m, 4H), 4.24-4.27 (m, 2H), 4.77-4.82 (m, 1H), 7.14-7.34 (m, 6H), 8.49 (d, J = 6.4 Hz, 1H) |

TABLE 42-continued

| No. | Structure | NMR (CDCl3 or d6-DMSO) |
|---|---|---|
| C-77 | 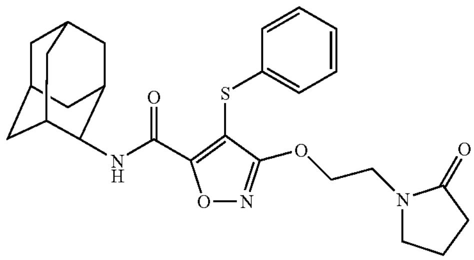 [SMILES: O=C(NC1C2CC3CC(C2)CC1C3)c1onc(OCCN2CCCC2=O)c1Sc1ccccc1] | (DMSO-d6); 1.48-2.12 (m, 18H), 3.10 (t, J = 7.2 Hz, 2H), 3.46-3.50 (m, 2H), 3.97-4.02 (m, 2H), 4.32-4.37 (m, 2H), 7.21-7.35 (m, 5H), 8.52 (d, J = 6.0 Hz, 1H) |
| C-78 | 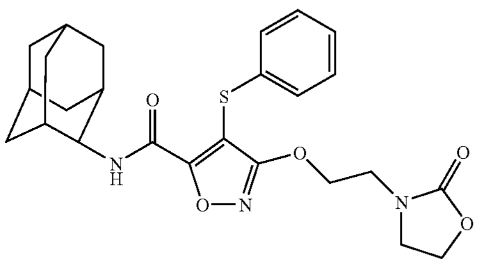 [SMILES: O=C(NC1C2CC3CC(C2)CC1C3)c1onc(OCCN2CCOC2=O)c1Sc1ccccc1] | (DMSO-d6); 1.24-2.01 (m, 14H), 3.16-3.41 (m, 2H), 3.44-3.50 (m, 3H), 3.93-4.08 (m, 2H), 4.25-4.38 (m, 2H), 7.23-7.32 (m, 5H), 8.48-8.53 (m, 1H) |

TABLE 43

| No. | Structure | NMR (CDCl3 or d6-DMSO) |
|---|---|---|
| C-79 | 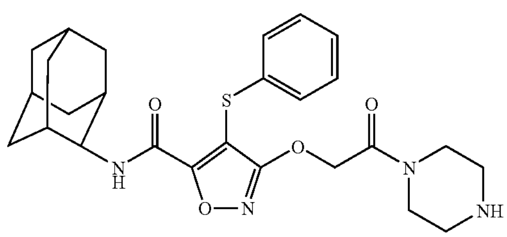 | (DMSO-d6); 1.48-1.89 (m, 14H), 3.05-3.10 (m, 4H), 3.59-3.65 (m, 4H), 3.97-3.98 (m. 1H), 5.16 (s, 2H), 7.21-7.34 (m, 5H), 8.55 (d, J = 8.0 Hz, 1H), 9.10-9.22 (m, 1H) |
| C-80 | 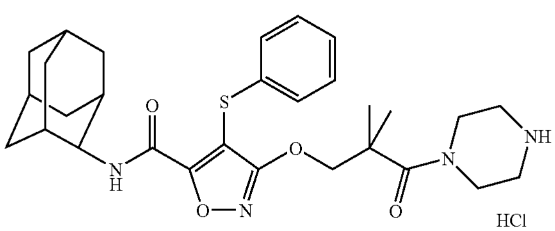 [SMILES: CC(C)(COc1noc(C(=O)NC2C3CC4CC(C3)CC2C4)c1Sc1ccccc1)C(=O)N1CCNCC1 ; Cl] | (DMSO-d6); 1.10 (s, 6H), 1.50-1.97 (m, 14H), 2.98-3.05 (m, 4H), 3.69-3.74 (m, 4H), 4.00-4.02 (m. 1H), 4.23 (s, 2H), 7.25-7.34 (m, 5H), 8.52 (d, J = 7.2 Hz, 1H), 9.27-9.32 (m, 1H) |
| C-81 | 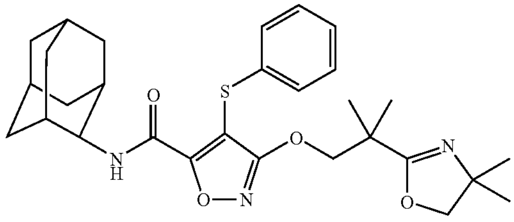 [SMILES: CC1(C)COC(C(C)(C)COc2noc(C(=O)NC3C4CC5CC(C4)CC3C5)c2Sc2ccccc2)=N1] | (DMSO-d6); 1.04 (s, 6H), 1.08 (s, 6H), 1.50-1.99 (m, 14H), 3.77 (s, 2H), 4.00-4.06 (m, 1H), 4.18 (s, 2H), 7.23-7.32 (m, 5H), 8.46-8.50 (m, 1H) |

TABLE 43-continued

| No. | Structure | NMR (CDCl3 or d6-DMSO) |
|---|---|---|
| C-82 | 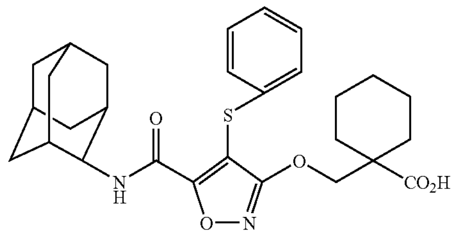 [SMILES: O=C(NC1C2CC3CC(C2)CC1C3)c1onc(OCC2(C(=O)O)CCCCC2)c1Sc1ccccc1] | (DMSO-d6); 1.15-1.92 (m, 24H), 3.98-4.02 (m, 1H), 4.23 (s. 2H), 7.25-7.32 (m, 5H), 8.51 (d, J = 6.4 HZ, 1H) |
| C-83 | 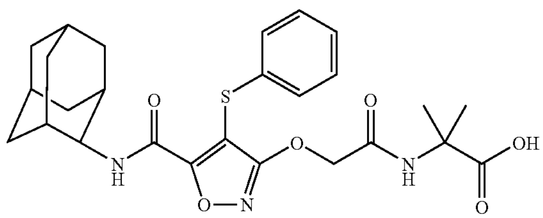 [SMILES: CC(C)(NC(=O)COc1noc(C(=O)NC2C3CC4CC(C3)CC2C4)c1Sc1ccccc1)C(=O)O] | (DMSO-d6); 1.35 (s, 6H), 1.48-1.99 (m, 14H), 3.92-4.00 (m, 1H), 4.72 (s. 2H), 7.21-7.33 (m, 5H), 8.14 (s, 1H), 8.53-8.55 (m, 1H), 12.34 (brs, 1H) |
| C-84 | 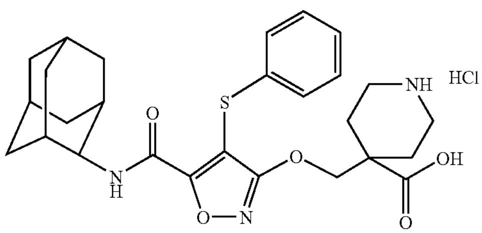 [SMILES: O=C(NC1C2CC3CC(C2)CC1C3)c1onc(OCC2(C(=O)O)CCNCC2)c1Sc1ccccc1 ; Cl] | (DMSO-d6); 0.79-2.00 (m, 20H), 2.80-2.86 (m, 1H), 3.06-3.14 (m, 1H), 4.01-4.33 (m, 3H), 7.25-7.46 (m, 5H), 8.52-8.60 (m, 1H), 9.40-9.52 (m, 1H) |

TABLE 44

| No. | Structure | NMR (CDCl3 or d6-DMSO) |
|---|---|---|
| C-85 | 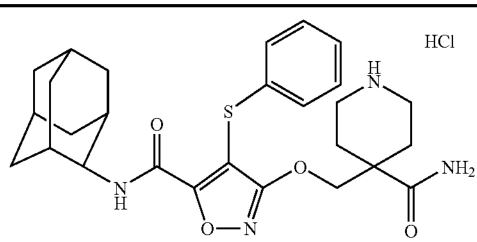 | (DMSO-d6); 0.82-2.06 (m, 20H), 2.82-2.90 (m, 1H), 3.10-3.17 (m, 1H), 4.00-4.05 (m, 1H), 4.33 (s, 2H), 7.25-7.36 (m, 5H), 7.51 (brs, 1H), 8.48-8.68 (m, 2H) |
| C-86 | 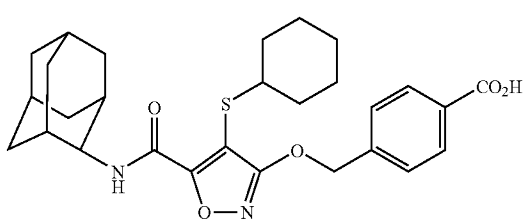 [SMILES: O=C(O)c1ccc(COc2noc(C(=O)NC3C4CC5CC(C4)CC3C5)c2SC2CCCCC2)cc1] | (DMSO-d6); 1.18-1.30 (m, 5H), 1.50-1.99 (m, 19H), 3.06-3.14 (m, 1H), 4.02-4.05 (m, 1H), 5.45 (s. 2H), 7.59 (d, J = 8.0 Hz, 2H), 7.98 (d, J = 8.0 Hz, 2H), 8.44 (d, J = 6.8 HZ, 1H), 12.97 (brs, 1H) |
| C-87 | 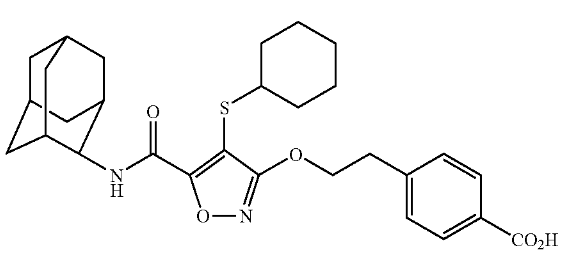 [SMILES: O=C(O)c1ccc(CCOc2noc(C(=O)NC3C4CC5CC(C4)CC3C5)c2SC2CCCCC2)cc1] | (DMSO-d6); 1.03-1.08 (m, 5H), 1.43-1.99 (m, 19H), 2.78-2.82 (m, 1H), 3.18 (t, J = 6.0 Hz, 2H), 4.00-4.04 (m, 1H), 4.57 (t, J = 6.0 Hz, 2H), 7.45 (d, J = 8.0 Hz, 2H), 7.89 (d, J = 8.0 Hz, 2H), 8.37 (d, J = 7.6 HZ, 1H), 12.88 (brs, 1H) |

TABLE 44-continued

| No. | Structure | NMR (CDCl3 or d6-DMSO) |
|---|---|---|
| C-88 | 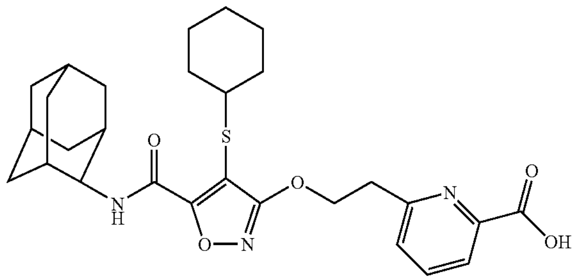 [SMILES: O=C(O)c1cccc(CCOc2noc(C(=O)NC3C4CC5CC(C4)CC3C5)c2SC2CCCCC2)n1] | (DMSO-d6); 0.96-1.10 (m, 5H), 1.41-1.98 (m, 19H), 2.75-2.82 (m, 1H), 3.33 (t, J = 6.0 Hz, 2H), 4.00-4.04 (m, 1H), 4.74 (t, J = 6.0 Hz, 2H), 7.61-7.63 (m, 1H), 7.90-7.95 (m, 2H), 8.37 (d, J = 7.6 HZ, 1H) |
| C-89 | 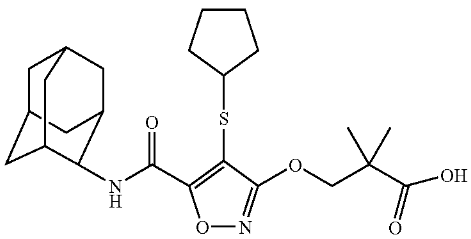 [SMILES: CC(C)(COc1noc(C(=O)NC2C3CC4CC(C3)CC2C4)c1SC1CCCC1)C(=O)O] | (DMSO-d6); 1.23 (s, 6H), 1.38-1.99 (m, 22H), 3.54-3.59 (m, 1H), 4.02-4.04 (m, 1H), 4.28 (s, 2H), 8.40 (d, J = 6.8 HZ, 1H), 12.55 (brs, 1H) |
| C-90 | 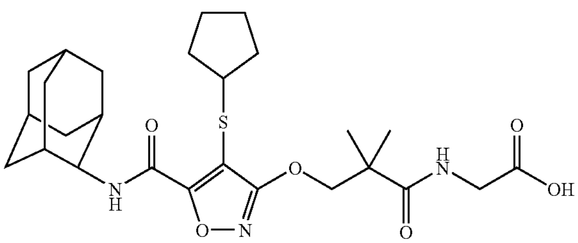 [SMILES: CC(C)(COc1noc(C(=O)NC2C3CC4CC(C3)CC2C4)c1SC1CCCC1)C(=O)NCC(=O)O] | (DMSO-d6); 1.24 (s, 6H), 1.42-1.98 (m, 22H), 3.52-3.59 (m, 1H), 3.71-3.72 (m, 2H), 4.02-4.04 (m, 1H), 4.28 (s, 2H), 8.00-8.06 (m, 1H), 8.37-8.39 (m, 1H), 12.41 (brs, 1H) |

TABLE 45

| No. | Structure | NMR (CDCl3 or d6-DMSO) |
|---|---|---|
| C-91 | 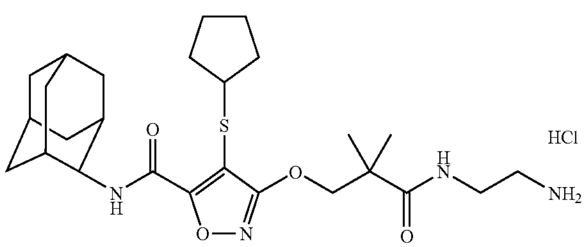 [SMILES: CC(C)(COc1noc(C(=O)NC2C3CC4CC(C3)CC2C4)c1SC1CCCC1)C(=O)NCCN ; Cl] | (DMSO-d6); 1.23 (s, 6H), 1.44-1.98 (m, 22H), 2.73-2.76 (m, 2H), 3.52-3.58 (m, 2H), 4.02-4.04 (m, 1H), 4.28 (s, 2H), 7.92-7.95 (m, 1H), 8.39 (d, J = 6.8 Hz, 1H) |
| C-92 | 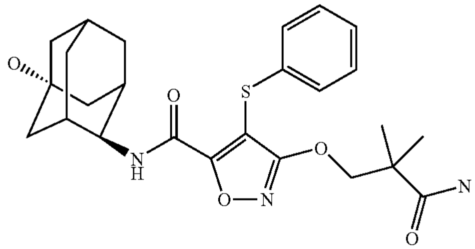 [SMILES: CC(C)(COc1noc(C(=O)N[C@H]2C3CC4CC2C[C@](O)(C4)C3)c1Sc1ccccc1)C(N)=O] | (DMSO-d6); 0.99 (s, 6H), 1.33-2.06 (m, 13H), 3.90-3.94 (m, 1H), 4.18 (s, 2H), 4.45 (brs, 1H), 6.91 (brs, 1H), 7.11 (brs, 1H), 7.26-7.33 (m, 5H), 8.47 (d, J = 6.0 Hz, 1H) |

TABLE 45-continued

| No. | Structure | NMR (CDCl3 or d6-DMSO) |
|---|---|---|
| C-93 | 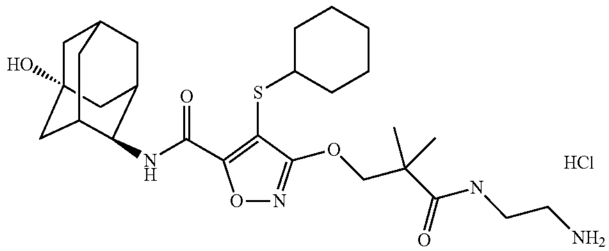 [SMILES: CC(C)(COc1noc(C(=O)N[C@H]2C3CC4CC2C[C@](O)(C4)C3)c1SC1CCCCC1)C(=O)NCCN ; Cl] | (DMSO-d6); 1.22-2.06 (m, 29H), 2.70-2.76 (m, 2H), 3.02-3.10 (m, 1H), 3.20-3.40 (m, 2H), 3.90-3.98 (m, 1H), 4.27 (s, 2H), 4.47 (brs, 1H), 7.78-7.84 (m, 1H), 8.30-8.38 (m, 1H) |
| C-94 | 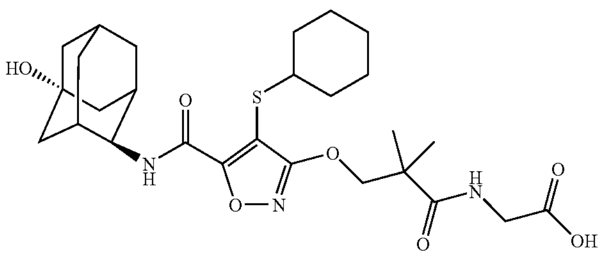 [SMILES: CC(C)(COc1noc(C(=O)N[C@H]2C3CC4CC2C[C@](O)(C4)C3)c1SC1CCCCC1)C(=O)NCC(=O)O] | (DMSO-d6); 1.22-2.06 (m, 29H), 3.06-3.14 (m, 1H), 3.20-3.40 (m, 2H), 3.70-3.74 (m, 2H), 3.90-3.98 (m, 1H), 4.27 (s, 2H), 8.00-8.06 (m, 1H), 8.30-8.38 (m, 1H) |
| C-95 | 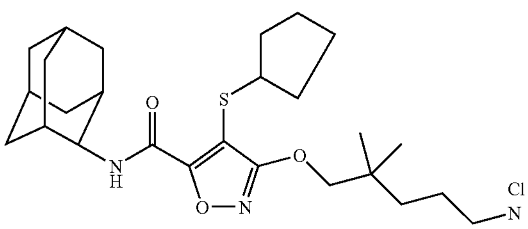 [SMILES: CC(C)(CCCN)COc1noc(C(=O)NC2C3CC4CC(C3)CC2C4)c1SC1CCCC1 ; Cl] | (DMSO-d6); 0.89 (t, J = 7.2 Hz, 3H), 1.44-2.83 (m, 33H), 3.98-4.06 (m, 1H), 4.52 (s, 2H), 7.96-8.00 (m, 2H), 8.34-8.39 (m, 1H) |

TABLE 46

| No. | Structure | LC-MS |
|---|---|---|
| C-96 | 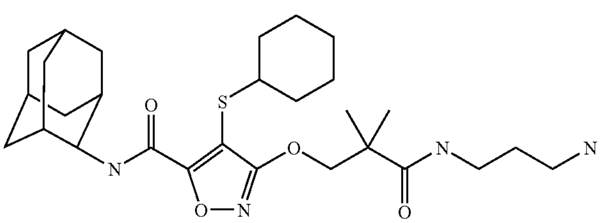 [SMILES: CC(C)(COc1noc(C(=O)NC2C3CC4CC(C3)CC2C4)c1SC1CCCCC1)C(=O)NCCCN] | Rt = 1.53 min m/z 532.4 (MH+) |
| C-97 | 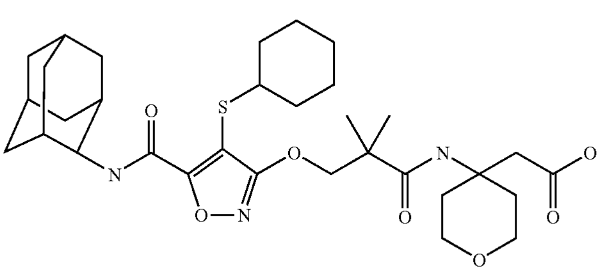 [SMILES: CC(C)(COc1noc(C(=O)NC2C3CC4CC(C3)CC2C4)c1SC1CCCCC1)C(=O)NC1(CC(=O)O)CCOCC1] | Rt = 2.66 min m/z 617.8 (MH+) |

TABLE 46-continued

| No. | Structure | LC-MS |
|---|---|---|
| C-98 | 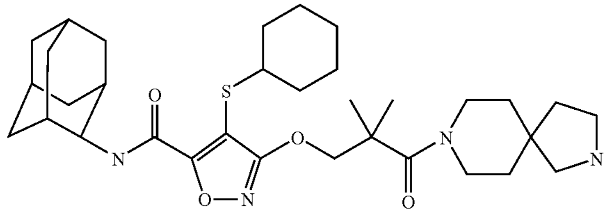 [SMILES: CC(C)(COc1noc(C(=O)NC2C3CC4CC(C3)CC2C4)c1SC1CCCCC1)C(=O)N1CCC2(CCNC2)CC1] | Rt = 1.66 min m/z 599.8 (MH+) |
| C-99 | 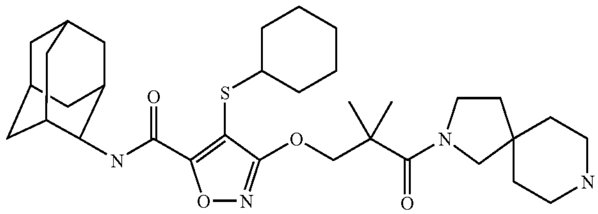 [SMILES: CC(C)(COc1noc(C(=O)NC2C3CC4CC(C3)CC2C4)c1SC1CCCCC1)C(=O)N1CCC2(CCNCC2)C1] | Rt = 1.62 min m/z 598.4 (MH+) |
| C-100 | 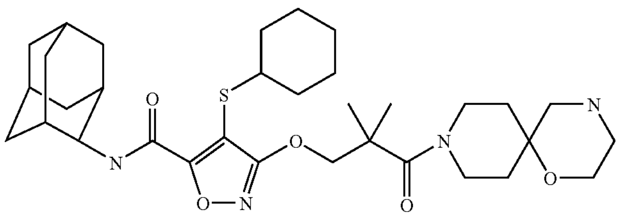 [SMILES: CC(C)(COc1noc(C(=O)NC2C3CC4CC(C3)CC2C4)c1SC1CCCCC1)C(=O)N1CCC2(CC1)CNCCO2] | Rt = 1.68 min m/z 614.4 (MH+) |
| C-101 | 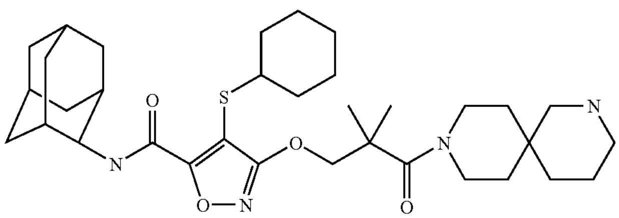 | Rt = 1.7 min m/z 613.1 (MH+) |

TABLE 47

| No. | Structure | LC-MS |
|---|---|---|
| C-102 | 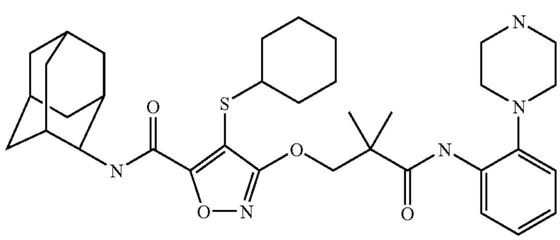 [SMILES: CC(C)(COc1noc(C(=O)NC2C3CC4CC(C3)CC2C4)c1SC1CCCCC1)C(=O)Nc1ccccc1N1CCNCC1] | Rt = 1.71 min m/z 635.2 (MH+) |
| C-103 | 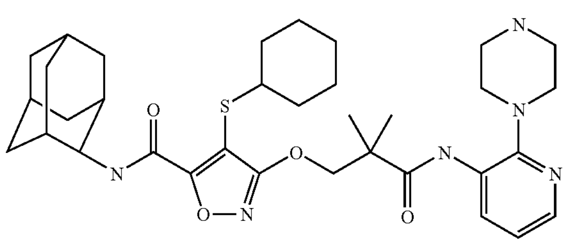 [SMILES: CC(C)(COc1noc(C(=O)NC2C3CC4CC(C3)CC2C4)c1SC1CCCCC1)C(=O)Nc1cccnc1N1CCNCC1] | Rt = 1.64 min m/z 636.2 (MH+) |

TABLE 47-continued

| No. | Structure | LC-MS |
|---|---|---|
| C-104 | 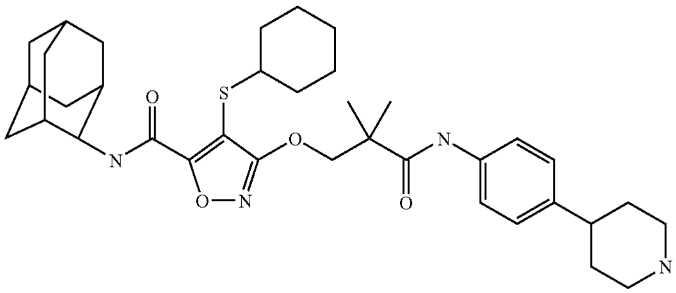 [SMILES: CC(C)(COc1noc(C(=O)NC2C3CC4CC(C3)CC2C4)c1SC1CCCCC1)C(=O)Nc1ccc(C2CCNCC2)cc1] | Rt = 1.71 min m/z 634.2 (MH+) |
| C-105 | 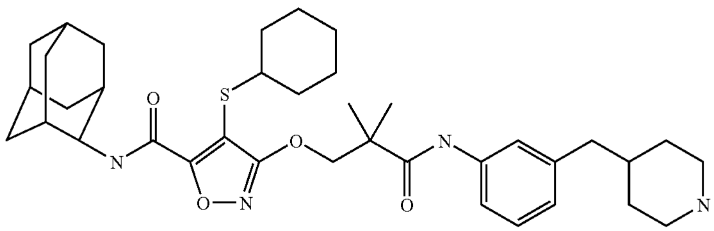 [SMILES: CC(C)(COc1noc(C(=O)NC2C3CC4CC(C3)CC2C4)c1SC1CCCCC1)C(=O)Nc1cccc(CC2CCNCC2)c1] | Rt = 1.78 min m/z 648.3 (MH+) |
| C-106 | Chiral | Rt = 1.61 min m/z 558.4 (MH+) |
| C-107 | 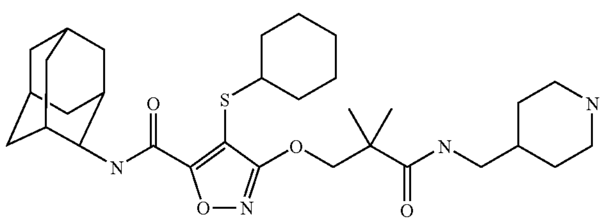 [SMILES: CC(C)(COc1noc(C(=O)NC2C3CC4CC(C3)CC2C4)c1SC1CCCCC1)C(=O)NCC1CCNCC1] | Rt = 1.57 min m/z 572.4 (MH+) |

TABLE 48

| No. | Structure | LC-MS |
|---|---|---|
| C-108 | 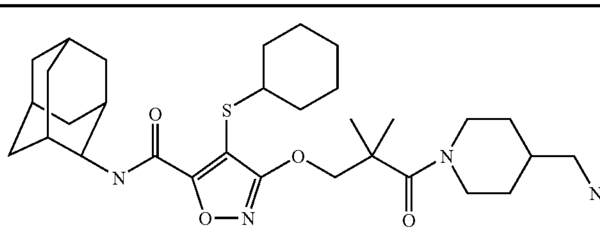 | Rt = 1.65 min m/z 572.4 (MH+) |
| C-109 | 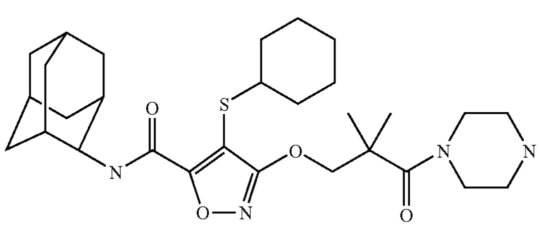 [SMILES: CC(C)(COc1noc(C(=O)NC2C3CC4CC(C3)CC2C4)c1SC1CCCCC1)C(=O)N1CCNCC1] | Rt = 1.6 min m/z 544.5 (MH+) |

TABLE 48-continued

| No. | Structure | LC-MS |
|-----|-----------|-------|
| C-110 | 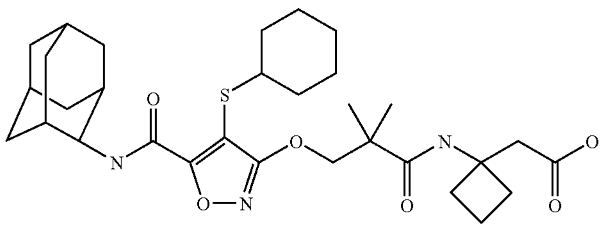 [SMILES: CC(C)(COc1noc(C(=O)NC2C3CC4CC(C3)CC2C4)c1SC1CCCCC1)C(=O)NC1(CC(=O)O)CCC1] | Rt = 2.85 min m/z 588.1 (MH+) |
| C-111 | Chiral | Rt = 2.85 min m/z 575.4 (MH+) |
| C-112 | 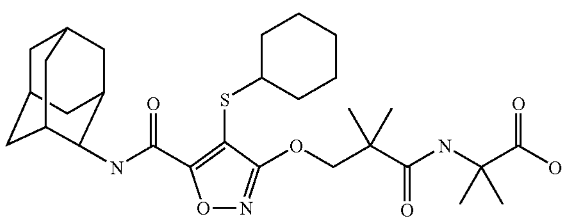 [SMILES: CC(C)(COc1noc(C(=O)NC2C3CC4CC(C3)CC2C4)c1SC1CCCCC1)C(=O)NC(C)(C)C(=O)O] | Rt = 2.77 min m/z 562.1 (MH+) |
| C-113 | 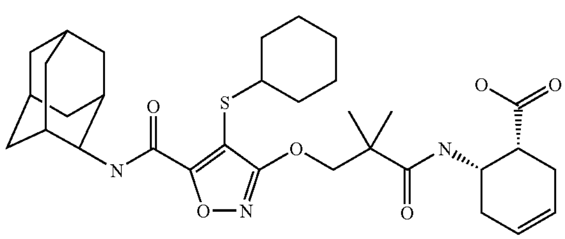 [SMILES: CC(C)(COc1noc(C(=O)NC2C3CC4CC(C3)CC2C4)c1SC1CCCCC1)C(=O)N[C@H]1CC=CC[C@H]1C(=O)O] | Rt = 2.84 min m/z 600.7 (MH+) |

TABLE 49

| No. | Structure | LC-MS |
|-----|-----------|-------|
| C-114 | 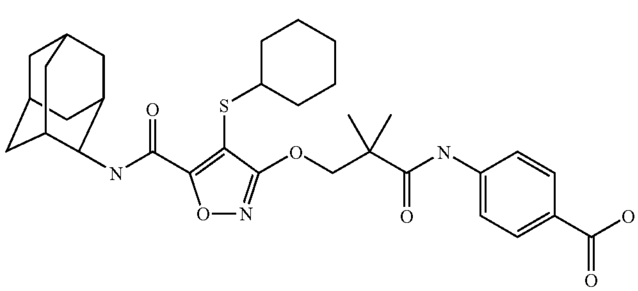 [SMILES: CC(C)(COc1noc(C(=O)NC2C3CC4CC(C3)CC2C4)c1SC1CCCCC1)C(=O)Nc1ccc(C(=O)O)cc1] | Rt = 2.73 min m/z 596.6 (MH+) |

TABLE 49-continued

| No. | Structure | LC-MS |
|---|---|---|
| C-115 | 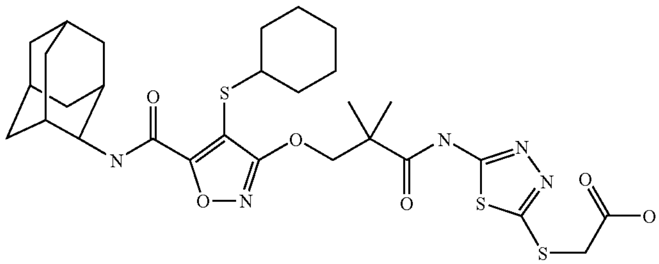 [SMILES: CC(C)(COc1noc(C(=O)NC2C3CC4CC(C3)CC2C4)c1SC1CCCCC1)C(=O)Nc1nnc(SCC(=O)O)s1] | Rt = 2.73 min m/z 650 (MH+) |
| C-116 | 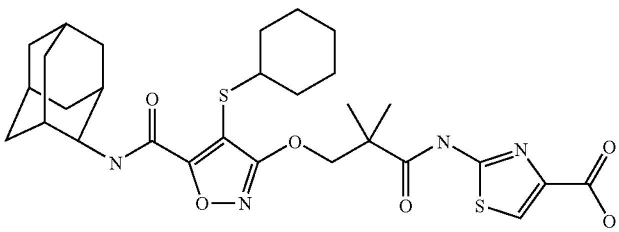 [SMILES: CC(C)(COc1noc(C(=O)NC2C3CC4CC(C3)CC2C4)c1SC1CCCCC1)C(=O)Nc1nc(C(=O)O)cs1] | Rt = 2.71 min m/z 603 (MH+) |
| C-117 | 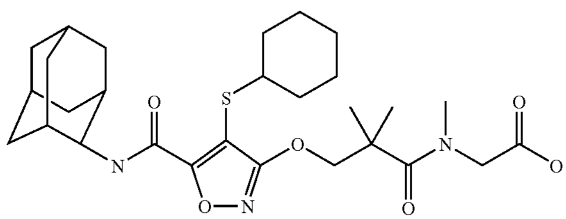 [SMILES: CN(CC(=O)O)C(=O)C(C)(C)COc1noc(C(=O)NC2C3CC4CC(C3)CC2C4)c1SC1CCCCC1] | Rt = 2.75 min m/z 548.6 (MH+) |
| C-118 | 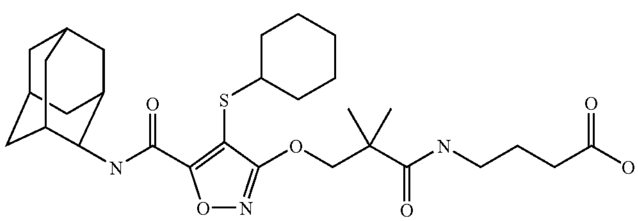 [SMILES: CC(C)(COc1noc(C(=O)NC2C3CC4CC(C3)CC2C4)c1SC1CCCCC1)C(=O)NCCCC(=O)O] | Rt = 2.56 min m/z 562.6 (MH+) |
| C-119 | Chiral | Rt = 2.68 min m/z 548.5 (MH+) |
| C-120 | Chiral | Rt = 2.66 min m/z 548.1 (MH+) |

Experimental Example 1

Evaluation of 11β-HSD1 Inhibitors (Enzyme Activity Assay on Human 11β-HSD1)

Enzymatic activity for human 11β-HSD1 was determined in a 10 μl final volume of assay mixture containing 50 mM sodium phosphate buffer (pH 7.6), 1 mg/ml bovine serum albumin, 0.42 mg/ml NADPH, 1.26 mg/ml glucose-6-phosphate, glucose-6-phosphate dehydrogenase, test compound, recombinant human 11β-HSD1, and 5 μM cortisone as substrate. The reaction was started with the addition of cortisone. After incubation for 2 hours at 37° C., 5 μl of europium cryptate-labelled anti-cortisol antibody and 5 μl of XL665- labeled cortisol were added. After further incubation for 2 hours at room temperature, the homogeneous time-resolved fluorescence (HTRF) signal was measured. The cortisol production was quantitated by a standard curve generated with several known concentrations of cortisol in each assay.

The amount of cortisol production without compounds was served as control, and the percent inhibition by test compound at each concentration was calculated. The IC50 value of the compound for 11β-HSD1 was obtained using the inhibition curve generated by plotting the percent inhibition versus the concentration of text compound.

Experimental Example 2

Evaluation of 11δ-HSD1 Inhibitors (Enzyme Activity Assay on Mouse 11β-HSD1)

Enzymatic activity for mouse 11β-HSD1 activity was determined in a 10 μl final volume of assay mixture containing 50 mM sodium phosphate buffer (pH 7.6), 1 mg/ml bovine serum albumin, 0.042 mg/ml NADPH, 1.26 mg/ml glucose-6-phosphate, glucose-6-phosphate dehydrogenase, test compound, recombinant mouse 11β-HSD1, and 2 M 11-dehydrocorticosterone as substrate. The reaction was started with the addition of 11-dehydrocorticosterone. After incubation for 2 hours at 37° C., 5 μl of europium cryptate-labelled anti-cortisol antibody and 5 μl of XL665-labeled cortisol were added. After further incubation for 2 hours at room temperature, the HTFR signal was measured. The corticosterone production was quantitated by a standard curve generated with several known concentrations of corticosterone in each assay.

Corticosterone production without compounds was served as control, and the percent inhibition by compound at each concentration was calculated. The IC50 value of the compound for 11β-HSD1 was obtained using the inhibition curve generated by plotting the percent inhibition versus the concentration of test compound.

The results of experimental example 1 and 2 are shown in the following table.

TABLE 50

| No. | human IC50(uM) | mouse IC50(uM) |
|---|---|---|
| A-1 | 0.084 | 21 |
| A-12 | 0.080 | 6.0 |
| A-15 | 0.016 | 11.6 |
| A-20 | 0.093 | 5.9 |
| A-21 | 0.015 | 21 |

Experimental Example 3

Materials and Methods in Oral Absorption of 11β-HSD1 Inhibitor (1) Animals

Male C57BL/6J Jcl mice were purchased from CLEA Japan at the age of 6 weeks. After 1-week preliminary rearing, the mice were used for this study at the age of 7 weeks (2) Rearing Conditions The mice were placed at an animal room, where was set at room temperature of 23±2° C. and humidity of 55±10%, and lighting cycle time was 12 hours [light (8:00-20:00)/dark (20:00-8:00)]. The mice were allowed free access to solid laboratory food (CE-2, CLEA Japan) and sterile tap water through the preliminary rearing and experimental periods.

(3) Identification of Animals and Cages

The mice were identified by tail marking with an oil marker pen. Labels identifying the study director, purchased date, strain, sex and supplier were placed on each cage. The mice were housed by 20 mice/cage in the preliminary rearing period, and 3 mice/cage in the experimental period.

(4) Group Composition

Oral administration: 20 mg/kg (n=3)

Intravenous administration: 5 mg/kg (n=3)

(5) Preparation of Dosing Formulation

Dosing suspension for oral administration was prepared using 0.5% methyl cellulose (1500 cP) aqueous solution. Dosing solution for intravenous administration was prepared using N-dimethylacetamide/polyethyleneglycol 400 (½).

(6) Dosing Method

As to oral administration, the dosing suspension at 10 mL/kg was administered into the stomach using a feeding tube. As to intravenous administration, the dosing solution at 2.5 mL/kg was administered into the caudal vein using a glass syringe.

(7) Evaluation Items

The blood samples were collected from the heart at each sampling point. The drug concentration in plasma was measured using HPLC or LC/MS/MS.

(8) Statistical Analysis

The area under the plasma concentration-time curve (AUC) was calculated by WinNonlin®, and the bioavailability was calculated by the AUC values after oral and intravenous administration.

Formulation Example 1

Hard gelatin capsules are prepared with the following ingredients:

| | Dose (mg/capsule) |
|---|---|
| Active ingredient | 250 |
| Starch (dried) | 200 |
| Magnesium stearate | 10 |
| Total | 460 mg |

Formulation Example 2

Tablets are prepared with the following ingredients:

| | Dose (mg/tablet) |
|---|---|
| Active ingredient | 250 |
| Cellulose (microcrystal) | 400 |
| Silicon dioxide, fumed | 10 |
| Stearic acid | 5 |
| Total | 665 mg |

The ingredients are blended and compressed to form tablets each weighing 665 mg.

Formulation Example 3

An aerosol solution is prepared containing the following ingredients:

|  | Weight |
| --- | --- |
| Active ingredient | 0.25 |
| Ethanol | 25.75 |
| Propellant 22 (chlorodifluoromethane) | 74.00 |
| Total | 100.00 |

The active ingredient is mixed with ethanol and the admixture is added to a portion of the propellant 22, cooled to −30° C. and transferred to a filling device. Then the required amount is provided in a stainless steel container and diluted with the reminder of the propellant. The valve units are then attached to the container.

Formulation Example 4

Tablets, each containing 60 mg of active ingredient, are made as follows.

| Active ingredient | 60 mg |
| --- | --- |
| Starch | 45 mg |
| Microcrystals cellulose | 35 mg |
| Polyvinyipyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the obtained powder, and then the admixture is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are added to the granules, mixed, and then compressed on a tablet machine to yield tablets each weighing 150 mg.

Formulation Example 5

Capsules, each containing 80 mg of active ingredient, are made as follows:

| Active ingredient | 80 mg |
| --- | --- |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppositories, each containing 225 mg of active ingredient, are made as follows:

| Active ingredient | 225 mg |
| --- | --- |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient, are made as follows:

| Active ingredient | 50 mg |
| --- | --- |
| Sodium carboxymethyl cellulose | 50 mg |
| Syrup | 1.25 mL |
| Benzole acid solution | 0.10 mL |
| Flavor | q.v. |
| Color | q.v. |
| Purified water to total | 5 mL |

The active ingredient is passed through a No. 45 U.S. sieve, and mixed with the sodium carboxymethyl cellulose and syrup to form a smooth paste. The benzoic acid solution and flavor are diluted with a portion of the water, added and stirred. Then sufficient water is added to produce the required volume.

Formulation Example 8

An intravenous formulation may be prepared as follows:

| Active ingredient | 100 mg |
| --- | --- |
| Saturated fatty acid glycerides | 1000 mL |

The solution of the above ingredients is generally administered intravenously to a patient at a rate of 1 mL per minute.

The invention claimed is:

1. A compound having inhibitory activity to 11β hydroxysteroid dehydrogenase type I having formula (I):

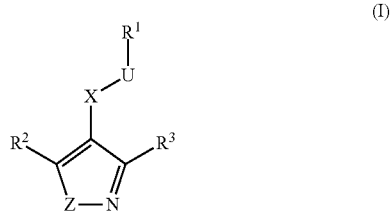

or a pharmaceutically acceptable salt thereof,
wherein
$R^1$ is optionally substituted cycloalkyl, optionally substituted cycloalkenyl, optionally substituted aryl, optionally substituted heteroaryl or optionally substituted heterocycle,
$R^2$ is a group of the formula: —C(=O)—Y—$R^4$,
wherein Y is —$NR^9$—, —C(=O)—, —$CH_2$—, a bond or —$NR^9$—W—, $R^4$ is optionally substituted cycloalkyl, optionally substituted cycloalkenyl, optionally substituted aryl, optionally substituted heteroaryl or optionally substituted heterocycle, $R^9$ is hydrogen or optionally substituted alkyl, and W is optionally substituted alkylene, $R^3$ is a group of the formula: —V—$R^5$, V is —O—, $R^6$ is hydrogen or optionally substituted alkyl, $R^5$ is hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle, X is a bond, —S—, —SO—, —SO$_2$—, —O—, —C≡C—, —C(=O)—, C(=O)—NR$^7$—, —NR$^7$—C(=O)—, —SO$_2$—NR$^7$—, —CH=CH— or —NR$^7$—SO$_2$—, U is a bond or optionally substituted alkylene, $R^7$ is hydrogen or optionally substituted alkyl, and Z is —O—.

2. The compound according to claim 1, or a pharmaceutically acceptable salt thereof, wherein Y is —NR$^9$— or a bond.

3. The compound according to claim 2, or a pharmaceutically acceptable salt thereof, wherein $R^9$ is hydrogen.

4. The compound according to claim 1, or a pharmaceutically acceptable salt thereof, wherein $R^5$ is optionally substituted alkyl.

5. The compound according to claim 1, or a pharmaceutically acceptable salt thereof, wherein $R^5$ is a group of the formula: —CH$_2$—C($R^{10}R^{11}$)—C(=O)—NR$^{12}R^{13}$ wherein $R^{10}$ and $R^{11}$ are each independently hydrogen, optionally substituted alkyl or halogen; or $R^{10}$ and $R^{11}$ taken together with the carbon atom to which they are attached may form an optionally substituted ring, $R^{12}$ and $R^{13}$ are each independently hydrogen, optionally substituted amino, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle; or $R^{12}$ and $R^{13}$ taken together with the nitrogen atom to which they are attached may form an optionally substituted ring.

6. The compound according to claim 1, or a pharmaceutically acceptable salt thereof, wherein $R^5$ is methyl.

7. The compound according to claim 1, or a pharmaceutically acceptable salt thereof, wherein $R^1$ is optionally substituted cycloalkyl or optionally substituted aryl.

8. The compound according to claim 7, or a pharmaceutically acceptable salt thereof, wherein $R^1$ is cyclohexyl or phenyl.

9. The compound according to claim 1, or a pharmaceutically acceptable salt thereof, wherein U is a bond.

10. The compound according to claim 1, or a pharmaceutically acceptable salt thereof, wherein X is —S—.

11. The compound according to claim 1, or a pharmaceutically acceptable salt thereof, wherein $R^4$ is optionally substituted cycloalkyl.

12. The compound according to claim 1, or a pharmaceutically acceptable salt thereof, wherein $R^4$ is optionally substituted phenyl or optionally substituted adamantyl.

13. A pharmaceutical composition which comprises the compound according to claim 1, or a pharmaceutically acceptable salt thereof as an active ingredient.

14. The pharmaceutical composition according to claim 13 for treating Type 2 diabetes.

\* \* \* \* \*